(12) United States Patent
Fogh et al.

(10) Patent No.: US 8,536,315 B2
(45) Date of Patent: Sep. 17, 2013

(54) PRODUCTION AND PURIFICATION OF RECOMBINANT ARYLSULFTASE

(75) Inventors: Jens Fogh, Lynge (DK); Claes Andersson, Taby (SE); Cecilia Weigelt, Stockholm (SE); Christer Moller, Tullinge (SE); Pia Hyden, Stocksund (SE)

(73) Assignee: Shire Pharmaceuticals Ireland Limited, Dublin (IE)

( * ) Notice: Subject to any disclaimer, the term of this patent is extended or adjusted under 35 U.S.C. 154(b) by 13 days.

(21) Appl. No.: 10/588,082

(22) PCT Filed: Jan. 30, 2005

(86) PCT No.: PCT/DK2005/000068
§ 371 (c)(1),
(2), (4) Date: Jun. 20, 2007

(87) PCT Pub. No.: WO2005/073367
PCT Pub. Date: Aug. 11, 2005

(65) Prior Publication Data
US 2008/0003211 A1    Jan. 3, 2008

Related U.S. Application Data

(60) Provisional application No. 60/540,061, filed on Jan. 30, 2004.

(30) Foreign Application Priority Data

Jan. 30, 2004 (DK) .......................... PA 2004 00144

(51) Int. Cl.
| | | |
|---|---|---|
| A23J 1/00 | (2006.01) |
| C12N 9/16 | (2006.01) |
| C12N 15/00 | (2006.01) |
| C12N 1/20 | (2006.01) |
| C12P 21/06 | (2006.01) |
| C12P 21/04 | (2006.01) |
| C07H 21/04 | (2006.01) |

(52) U.S. Cl.
USPC ........... 530/412; 530/414; 530/416; 530/417; 435/196; 435/252.3; 435/320.1; 435/440; 435/69.1; 435/71.1; 536/23.2

(58) Field of Classification Search
None
See application file for complete search history.

(56) References Cited

U.S. PATENT DOCUMENTS

| 6,197,507 | B1 | 3/2001 | Berg et al. |
| 6,812,339 | B1 | 11/2004 | Venter et al. |
| 7,232,670 | B2 | 6/2007 | D'Azzo et al. |
| 2003/0199073 | A1 | 10/2003 | Fogh et al. |
| 2004/0126370 | A1 | 7/2004 | D'Azzo et al. |

FOREIGN PATENT DOCUMENTS

| JP | 2002-517516 A | 6/2002 |
| WO | 99/37325 | 7/1999 |
| WO | 99/64462 | 12/1999 |
| WO | 0067789 | 11/2000 |
| WO | 01/07065 A2 | 2/2001 |
| WO | WO 02/40686 | 5/2002 |
| WO | 02/099092 A2 | 12/2002 |
| WO | WO 02/098455 | 12/2002 |
| WO | 03/002731 A1 | 1/2003 |
| WO | 03/057179 A2 | 7/2003 |
| WO | 03/066669 A2 | 8/2003 |
| WO | 2005/073367 A1 | 8/2005 |
| WO | 2005/094874 A1 | 10/2005 |

OTHER PUBLICATIONS

Branden et al. Introduction to Protein Structure, Garland Publishing Inc., New York, p. 247, 1991.*
Current Protocols in Protein Sciences. John Wiley & Sons, Inc. Unit 5.10. 1998.*
Protein Purification Handbook. GE Healthcare. Oct. 2001.*
Wang et al. Erythropoietin production from CHO cells grown by continuous culture in a fluidized-bed bioreactor. Biotechnol Bioeng. Jan. 20, 2002;77(2):194-203.*
Sofer et al. Preparative chromatographic separations in pharmaceutical, diagnostic, and biotechnology industries: current and future trends. J Chromatogr A. Jul. 14, 1995;707(1):23-8.*
Millipore. Millipore Corporation, Billerica, MA 01821. USA. 2003.*
Baum, et al., "The assay of arylsulphatases A and B in human urine", *Clin. Chim. Acta*, vol. 4, pp. 453-455, 1959.
Coenen, et al. "Morphological alterations in the inner ear of the arylsulfatase A-deficient mouse" *Acta. Neuropathol*, vol. 101, pp. 491-498, 2001.
Demeule, et al. "High transcytosis of melanotransferrin (P97) across the blood-brain barrier", *Journal of Neurochemistry*, vol. 83, pp. 924-933, 2002.
D'Hooge et al., "Hyperactivity, neuromotor defects, and impaired learning and memory in a mouse model for metachromatic leukodystrophy", *Brain Research*, vol. 907 pp. 35-43, 2001.

(Continued)

*Primary Examiner* — Yong Pak
(74) *Attorney, Agent, or Firm* — Lando & Anastasi LLP

(57) ABSTRACT

The present invention pertains to a process for production of recombinant arylsulfatase A in a cell culture system, the process comprising culturing a mammalian cell capable of producing rASA in liquid medium in a system comprising one or more bio-reactors; and concentrating, purifying and formulating the rASA by a purification process comprising one or more steps of chromatography. Other aspects of the invention provides a pharmaceutical composition comprising rASA, which is efficiently endocytosed via the mannose-6-phosphate receptor pathway in vivo as well as a rhASA a medicament and use of a rhASA for the manufacture of a medicament for reducing the galactosyl sulphatide levels within target cells in the peripheral nervous system and/or within the central nervous system in a subject. A final aspect of the invention provides a method of treating a subject in need thereof, said method comprising administering to said subject a pharmaceutical composition comprising a rhASA and thereby obtaining a reduction in the galactosyl sulphatide levels in target cells within said subject.

35 Claims, 17 Drawing Sheets

(56) References Cited

OTHER PUBLICATIONS

Figure 1:
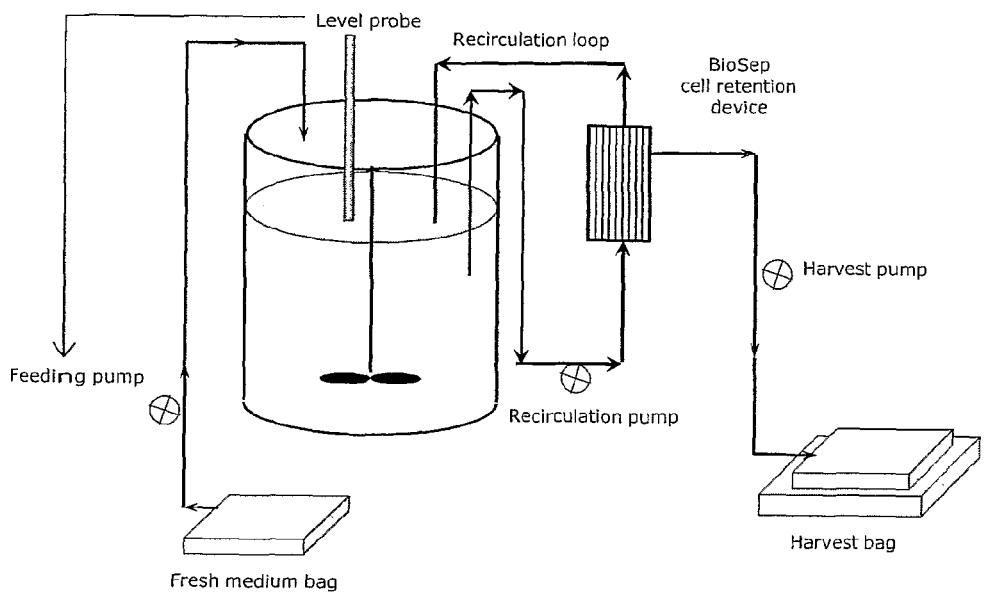
Figure 1:
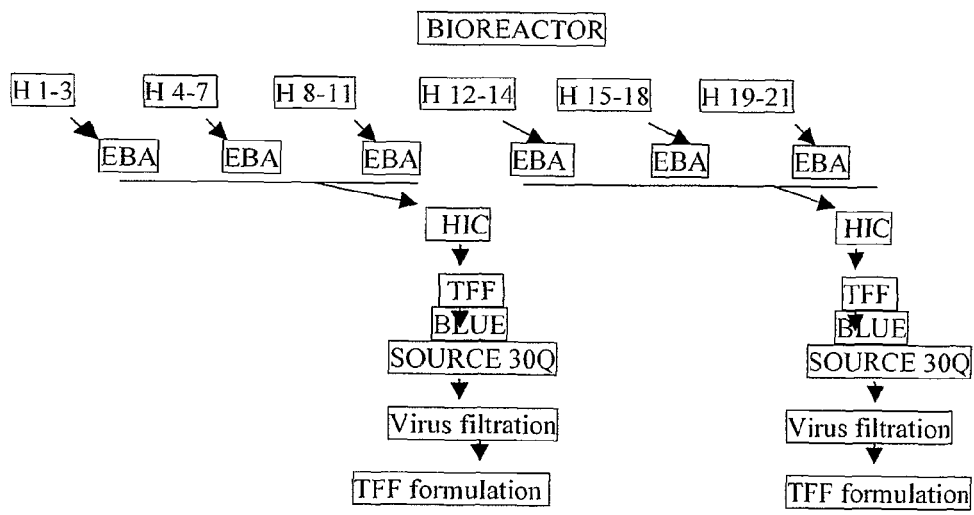

Dierks et al., "Conversion of cysteine to formylglycine: A protein modification in the endoplasmic reticulum", *Proc. Natl. Acad. Sci. USA*, vol. 94, pp. 11963-11968, Oct. 1997.

Dunican, et al., "Designing Cell-Permeant Phosphopeptides to Modulate Intracellular Signaling Pathways", *Biopolymers (Peptide Science)*, vol. 60 pp. 45-60, 2001.

Gieselmann, et al., "Metachromatic leukodystrophy: Molecular genetics and an animal model", *J. Inher. Metab. Dis.*, vol. 21, pp. 564-574, 1998.

Gieselmann, et al., Metachromatic leukodystrophy: consequences of sulphatide accumulation, *Acta Paediatr Suppl.*, vol. 443, pp. 74-79, 2003.

V. Gieselmann, et al., "In Vitro Mutagenesis of Potentioal N-Glycosylation Sites of Arylsulfatase A", *Journal of Biological Chemistry*, vol. 267, No. 19, pp. 13262-13266, Jul. 5, 1992.

Hess, et al., "Phenotype of arylsufatase A-deficient mice: Relationship to human metachromatic leukodystrophy", *Proc. Natl. Acad. Sci. USA*, vol. 93, pp. 14821-14826, Dec. 1996.

Ho, et al., "Synthetic Protein Transduction Domains: Enhanced Transduction Potential in Vitro and in Vivo[1]", *Cancer Research*, vol. 61, pp. 474-477, Jan. 15, 2001.

Kudoh, et al., "Diagnosis of Metachromatic Leukodystrophy, Krabbe Disease, and Farber Disease after Uptake of Fatty Acid-labeled Cerebroside Sulfate into Cultured Skin Fibroblasts", *J. Clin. Invest.*, vol. 70, pp. 89-97, Jul. 1982.

Lindgren, et al., "Cell-penetrating peptides", *TIPS*, vol. 21, pp. 99-103, Mar. 2000.

Lukatela, et al., "Crystal Structure of Human Arylsufatase A: The Aldehyde Function and the Metal Ion at the Active Site Suggest a Novel Mechanism for Sulfate Ester Hydrolysis", *Biochemistry*, vol. 37, pp. 3654-3664, 1998.

Lüllmann-Rauch, et al., "Lysosomal sulfoglycolipid storage in the kidneys of mice deficient for arysulfatase A (ASA) and of double-knockout mice deficient for ASA and galactosylceramide synthase", *Histochem Cell Biol*, vol. 116, pp. 161-169, 2001.

Matsushima, et al. "Absence of MHC Class II Molecules Reduces CNS Demyelination, Microglial/Macrophage Infiltration, and Twitching in Murine Globoid Cell Leukodystrophy", *Cell*, vol. 78, pp. 645-656, Aug. 26, 1994.

Matzner, et al., "Long-term expression and transfer of arylsulfatase A into brain of arylsulfatase A-deficient mice transplanted with bone marrow expressing the arylsulfatase A cDNA from a retroviral vector", *Gene Therapy*, vol. 7, pp. 1250-1257, 2000.

Matzner et al., "Retrovirally expressed human arylsufatase A corrects the metabolic defect of arylsulfatase A-deficient mouse cells", *Gene Therapy*, vol. 7, pp. 805-812, 2000.

Muschol, et al., "Secretion of phosphomannosyl-deficient arylsulphatase A and cathepsin D from isolated human macrophages", *Biochem J.*, vol. 368, pp. 845-853, 2002.

Pan et al., "TNF α Transport across the Blood-Brain Barrier is Abolished in Receptor Knockout Mice", *Experimental Neurology*, vol. 174, pp. 193-200, 2002.

Pan et al., "Upregulation of the Transport System for TNF α at the Blood-Brain Barrier", *Archives of Physiology and Biochemistry*, vol. 109, No. 4, pp. 350-353, 2001.

Rodman, et al., Circulating natural IgM antibodies and their corresponding human cord blood cell-derived Mabs specifically combat the Tat protein of HIV, Experimental Hematology, vol. 29, pp. 1004-1009, 2001.

Rothenberger, et al., "Coincident expression and distribution of melanotransferrin and transferring receptor in human brain capillary endothelium", *Brain Research*, vol. 712, pp. 117-121, 1996.

Sandhoff, et al., "Kidney Sulfatides in Mouse Models of Inherited Glycosphingolipid Disorders", *The Journal of Biological Chemistry*, vol. 277, No. 23, pp. 20386-20398, 2002.

Schmidt, et al., "A Novel Amino Acid Modification in Sulfatases That is Defective in Multiple Sulfatase Deficiency", *Cell*, vol. 82, pp. 271-278, Jul. 28, 1995.

Schwarze, et al., Protein transduction: unrestricted delivery into all cells?, *trends in Cell Biology*, vol. 10, pp. 290-295, Jul. 2000.

Scott, et al., "Differential Staining of Acid Glycosaminoglycans (Mucopolysaccharides) by Alcian Blue in Salt Solutions", *Histochemie*, vol. 5, pp. 221-233, 1965.

Selmer, et al., "The evolutionary conversation of a novel protein modification, the conversion of cysteine to serinesemialdehyde in arylsufatase from Volvox carteri", *Eur. J. Biochem.*, vol. 238, pp. 341-345, 1996.

Sommerlade, et al., "Four monoclonal antibodies inhibit the recognition of arylsulphatase A by the lysosomal enzyme phosphotransferase", *Biochem J.*, vol. 297, pp. 123-130, 1994.

Wada, et al., "Microglial activation precedes acute neurodegeneration in Sandhoff disease and is suppressed by bone marrow transplantation", *Proc. Nat. Acad. Sci. (USA)*, vol. 97, No. 20, pp. 10954-10959, Sep. 26, 2000.

Wittke, et al., "Lysosomal sulfatide storage in the brain of arylsulfatase A-deficient mice: cellular alterations and topographic distribution", *Acta Neuropathol*, vol. 108, pp. 261-271, 2004.

Wu, et al., "Neuroprotection with noninvasive neurotrophin delivery to the brain", *Proc. Natl. Acad. Sci. USA*, vol. 96, pp. 254-259, Jan. 1999.

Yao, et al., "Microanalysis of Complex Tissue Lipids by High-Performance Thin-Layer Chromatography", *Analytical Biochemistry*, vol. 150, pp. 111-116, 1985.

Zielasek, et al., "Functional Abnormalities in $P_0$-Deficient Mice Resemble Human Hereditary Neuropathies Linked to $P_0$ Gene Mutations", *Muscle & Nerve*, vol. 19, pp. 946-952, 1996.

Bond, et al., "Structure of a human lysosomal sulfatase", *Structure*, vol. 5, No. 2, pp. 277-289, 1997.

Franco, et al., "A Cluster of Sulfatase Genes on Xp22.3: Mutations in Chondrodysplasia Punctata (CDPX) and Implications for Warfarin Embryopathy", *Cell*, vol. 81, pp. 15-25, Apr. 7, 1995.

Gieselmann, et al., "Arylsulfatase A pseudodeficiency: Loss of a polyadenylylation signal and N-glycosylation site", *Proc. Natl. Acad. Sci. USA*, vol. 86, pp. 9436-9440, Dec. 1999.

Hallmann, et al., "An inducible arylsulfatase of *Volvox carteri* with properties suitable for a reporter-gene system", *Eur. J. Biochem.*, vol. 221, pp. 143-150, 1994.

James, Gordon T., "Essential Arginine Residues in Human Liver Arylsulfatase A", *Archives of Biochemistry and Biophysics*, vol. 197, No. 1, pp. 57-62, 1979.

Lee, et al., "Evidence for an Essential Histidine Residue in Rabbit Liver Aryl Sulfatase A", *Archives of Biochemistry and Biophysics*, vol. 171, pp. 424-434, 1975.

Perusi, et al., "A novel mutation which represents the fifth non-pathogenic polymorphism in the coding sequence of the Arylsulfatase A gene", *Molecular and Cellular Probes*, vol. 11, pp. 449-451, 1997.

Peters, et al., "Phylogenetic Conservation of Arylsulfatases", *The Journal of Biological Chemistry*, vol. 265, No. 6, pp. 3374-3381, Feb. 25, 1990.

Rafi, et al., "Disease-causing mutations in *cis* with the common arylsulfatase A pseudodeficiency allele compound the difficulties in accurately identifying patients and carriers of metachromatic leukodystrophy", *Molecular Genetics and Metabolism*, vol. 79, pp. 83-90, 2003.

Ricketts, et al., "The R496H Mutation of Arylsulfatase A Does Not Cause Metachromatic Leukodystrophy", *Human Mutation*, vol. 12, pp. 238-239, 1998.

Schuchman, et al., "Human Arylsulfatase B: MOPAC Cloning, Nucleotide Sequence of a Full-Length cDNA, and Regions of Amino Acid Identity with Arylsulfatases A and C", *Genomics*, vol. 6, pp. 149-158, 1990.

Steven J. Shire et al., "Challenges in the Development of High Protein Concentration Formulations", Journal of Pharmaceutical Sciences, vol. 93, No. 6, Jun. 2004, pp. 1390-1402.

Thomas Pohl, "(7) Concentration of Proteins and Removal of Solutes", Methods in Enzymology, vol. 182, 1990, pp. 68-83.

Caroline Sevin et al., "Intracerebral adeno-associated virus-mediated gene transfer in rapidly progressive forms of metachromatic leukodystrophy", Human Molecular Genetics, 2006, vol. 15, No. 1, pp. 53-64.

William R. Pearson et al., "Improved tools for biological sequence comparison", Proc Natl Acad Sci USA, vol. 85, pp. 2444-2448, Apr. 1988.

William R. Pearson, "(5) Rapid and Sensitive Sequence Comparison with FASTP and FASTA", Methods of Enzymology, vol. 183, 1990, pp. 63-98.

Julie D. Thompson et al., Ciustai W: improving the sensitivy of progressive multiple sequence alignment through sequence weighting, position-specific gap penalties and weight matrix choice, Nucleic Acids Research, 1994, vol. 22, No. 22, 4673-4680.

Aryan I. Fluharty et al., "[58] Arylsulfatases A and B from Human liver", Meth. Enzymol. 50:537-547, 1978.

Abdul Waheed et al., "Phosphorylation and sulfation of arylsulfatase A accompanies biosynthesis of the enzyme in normal and carcinoma cell lines", Biochimica et Biophysica Acta 847 (1985) 53-61.

Thomas Braulke et al., "Sulfated Oligosaccharides in Human Lysosomal Enzymes", Biochemical and Biophysical Research Communications, vol. 143, No. 1, 1987, pp. 178-185.

Thomas Braulke et al., "Insulin-like Growth Factors I and II Stimulate Endocytosis but Do Not Affect Sorting of Lysosomal Enzymes in Human Fibroblasts", The Journal of Biological Chemistry, vol. 265, No. 12, Issue of Apr. 25, 1990,pp. 6650-6655.

Bernadette M. Kelly et al., "Presence of a lysosomal enzyme, arylsulfatase-A, in the prelysosome-endosome compartments of human cultured fibroblasts", European Journal of Cell Biology, 48, 71-78, 1989.

Nathan N. Aronson, Jr et al., "Lysosomal degradation of Asn-linked glycoprotein", The FASEB Journal, vol. 3, Dec. 1989, pp. 2615-2622.

Oivind Nilssen et al., "a-Mannosidosis: functional cloning of the lysosomal a-mannosidase cDNA and identification of a mutation in two affected siblings", Human Molecular Genetics, 1997, vol. 6 No. 5, pp. 717-726.

Yasufumi Kaneda et al., "Regional assignment of five genes on human chromosome 19", Chromosoma (BerJ) (1987) 95:8-12.

Hilde Monica Frostad Riise et al., Genomic Strucutre of the Human Lysosomal a-Mannosidase Gene (MANB) Genomics 42, 200-207 (1997).

Yung-Feng Liao et al., "Cloning, Expression, Purification and Characterization of the Human Broad Specificity Lysosomal Acid a-Mannosidase", The Journal of Biological Chemistry, vol. 271, No. 45, Issue of Nov. 8, 1996, pp. 28348-28358.

Vicki L. Nebes et al., "Human Lysosomal Alpha-Mannosidase: Isolation and Nucleotide Sequence of the Full-Length cDNA", Biochemical and Biophysical Research Communications, vol. 200, No. 1, 1994, pp. 239-245.

P. N. Meissner et al., "Protoporphyrinogen oxidase and porphobilinogen deaminase in variegate porphyria", European Journal of Clinical Investigation (1986) 16 257-261.

Richard J. Hift et al., "Variegate porphyria in South Africa, 1688-1996—new developments in an old disease", S. Afr. Med. J., vol. 87, No. 6, Jun. 1997, pp. 722-731.

Peter Meissner et al., "Allosteric Inhibition of Human Lymphoblast and Purified Porphobilinogen Deaminase by Protoporphyrinogen and Coproporphyrinogen", J. Clin. Invest., 1993, vol. 91,1436-1444.

James Austin et al., "Abnormal Sulphatase Activities in Two Human Diseases (Metachromatic Leucodystrophy and Gargoylism)", Biochem. J. (1964),93, 15c-17c.

U.S. Appl. No. 12/295,848, filed Apr. 4, 2007, Published.

Bostick, et al., "Separation and Analysis of Arylsulfatase Isoenzymes in Body Fluids of Man", Clinical Chemistry, American Association for Clinical Chemistry, vol. 24, No. 8, pp. 1305-1316, 1978.

Kakkis, et al.,Abstract only, Abstract No. 281-0, "A Method to Reduce the Immune Response to Enzyme Replacement Therapy:Studies of Criteria for Success", J. Inherit. Metab. Dis., vol. 26, Suppl. 2, 2003.

Kakkis, et al., Abstract only, Abstract No. 282-0, "Effective Reduction of Lysosomal Storage in Brain and Meninges Following Intrathecal Administration of Iduronidase in Canine Mucopolysaccharidosis I (MPS I)"; J. Inherit. Metab. Dis., 2003.

Matzner, et al., "Bone marrow stem cell-based gene transfer in a mouse model for metachromatic leukodystrophy: effects on visceral and nervous system disease manifestations", Gene Therapy, vol. 9, pp. 53-63, 2002.

Sangalli, et al., "Transduced Fibroblasts and Metachromatic Leukodystrophy Lymphocytes Transfer Arylsulfatase A to Myelinating Glia and Deficient Cells In Vitro", Human Gene Therapy, vol. 9, pp. 2111-2119, Sep. 20, 1998.

Sarafian, et al., "Studies on the Charge Isomers of Arylsulfatase $A^{1}$", Biochemical Medicine, vol. 33, pp. 372-380, 1985.

Stein, et al., "Cloning and Expression of Human Arylsulfatase A", The Journal of Biological Chemistry, vol. 264, No. 2, pp. 1252-1259, Jan. 15, 1989.

Stevens, et al., "Purification and Properties of Arylsulfatase A from Human Urine", The Journal of Biological Chemistry, vol. 250, No. 7, pp. 2495-2501, Apr. 10, 1975.

Ben-Yoseph et al., "The Interrelations between High- and Low-Molecular-Weight Forms of Normal and Mutant (Krabbe-Disease) Galactocerebrosidase", J. Biochem., vol. 189, pp. 9-15 (1980).

Sakai et al., "Purification and Chracterization of Galactocerebrosidase from Human Lymphocytes", J. Biochem., vol. 116, No. 3, pp. 615-620 (1994).

Treuheit et al., "Inverse Relationship of Protein Concentration and Aggregation", Pharmaceutical Research, vol. 19, No. 4, pp. 511-516 (2002).

Berg et al., "Purification and characterization of Recombinant Human Lysosomal a-mannosidase" Molecular Genetics and Metabolism, 73, pp. 18-29 (2001).

Jordan et al., "Purification, crystallization and properties of porphobilinogen deaminase from a recombinant strain of Escherichia coli K12", Biochem., vol. 254, pp. 427-435 (1988).

Matzner et al., "Enzyme replacement improves nervous system pathology and function in a mouse model for metachromatic leukodystrophy", Human Molecular Genetics, vol. 14, pp. 1139-1152 (2005).

Tollersrud, et al., "Purification of bovine lysosomal a-mannosidase, characterization of its gene and dtermination of two mutations that cause a-mannosidosis", Eur. J. Biochem. 246, pp. 410-419, (1997).

* cited by examiner

A

B

SEQUENCE LISTING

```
<160> NUMBER OF SEQ ID NOS: 4

<210> SEQ ID NO 1
<211> LENGTH: 1524
<212> TYPE: DNA
<213> ORGANISM: Homo Sapiens

<400> SEQUENCE: 1
atgggggcac cgcggtccct cctcctggcc ctggctgctg gcctggccgt tgcacgtccg       60
cccaacatcg tgctgatctt tgccgacgac ctcggctatg gggacctggg ctgctatggg      120 cacccccagct ctaccactcc caacctggac cagctggcgg cgggagggct gcggttcaca      180
gacttctacg tgcctgtgtc tctgtgcaca ccctctaggg ccgccctcct gaccggccgg      240
ctcccggttc ggatgggcat gtaccctggc gtcctggtgc ccagctcccg gggggggcctg      300 ccctggagg aggtgaccgt ggccgaagtc ctggctgccc gaggctacct cacaggaatg       360
gccggcaagt ggcaccttgg ggtggggcct gagggggcct tcctgccccc ccatcagggc      420
ttccatcgat ttctaggcat cccgtactcc cacgaccagg gcccctgcca gaacctgacc      480
tgcttcccgc cggccactcc ttgcgacggt ggctgtgacc agggcctggt cccccatccca     540 ctgttggcca acctgtccgt ggaggcgcag ccccccctggc tgcccggact agaggcccgc      600
tacatggctt tcgcccatga cctcatggcc gacgcccagc gccaggatcg ccccttcttc      660
ctgtactatg cctctcacca cacccactac cctcagttca gtgggcagag cttgcagag      720 cgttcaggcc gcgggccatt tggggactcc ctgatggagc tggatgcagc tgtggggacc      780
ctgatgacag ccatagggga cctggggctg cttgaagaga cgctggtcat cttcactgca      840
gacaatggac ctgagaccat gcgtatgtcc cgaggcggct gctccggtct cttgcggtgt      900
ggaaagggaa cgacctacga gggcggtgtc cgagagcctg ccttggcctt ctggccaggt      960
catatcgctc ccggcgtgac ccacgagctg gccagctccc tggacctgct gcctaccctg     1020
gcagccctgg ctggggcccc actgcccaat gtcaccttgg atggctttga cctcagcccc     1080
ctgctgctgg gcacaggcaa gagccctcgg cagtctctct tcttctaccc gtcctaccca     1140
gacgaggtcc gtggggtttt tgctgtgcgg actggaaagt acaaggctca cttcttcacc     1200
cagggctctg cccacagtga taccactgca gaccctgcct gccacgcctc cagctctctg     1260
actgctcatg agccccgct gctctatgac ctgtccaagg accctggtga gaactacaac     1320
ctgctggggg gtgtggccgg ggccacccca gaggtgctgc aagccctgaa acagcttcag     1380
ctgctcaagg cccagttaga cgcagctgtg accttcggcc ccagccaggt ggcccggggc     1440
gaggaccccg ccctgcagat ctgctgtcat cctggctgca ccccccgccc agcttgctgc     1500
cattgcccag atccccatgc ctga                                             1524

<210> SEQ ID NO 2
<211> LENGTH: 507
<212> TYPE: PRT
<213> ORGANISM: Homo Sapiens
```

<400> SEQUENCE: 2

```
Met Gly Ala Pro Arg Ser Leu Leu Ala Leu Ala Ala Gly Leu Ala
  1               5                  10                  15

Val Ala Arg Pro Pro Asn Ile Val Leu Ile Phe Ala Asp Asp Leu Gly
             20                  25                  30

Tyr Gly Asp Leu Gly Cys Tyr Gly His Pro Ser Ser Thr Thr Pro Asn
             35                  40                  45

Leu Asp Gln Leu Ala Ala Gly Gly Leu Arg Phe Thr Asp Phe Tyr Val
 50                  55                  60

Pro Val Ser Leu Cys Thr Pro Ser Arg Ala Ala Leu Leu Thr Gly Arg
 65                  70                  75                  80

Leu Pro Val Arg Met Gly Met Tyr Pro Gly Val Leu Val Pro Ser Ser
                 85                  90                  95

Arg Gly Gly Leu Pro Leu Glu Glu Val Thr Val Ala Glu Val Leu Ala
                100                 105                 110

Ala Arg Gly Tyr Leu Thr Gly Met Ala Gly Lys Trp His Leu Gly Val
            115                 120                 125

Gly Pro Glu Gly Ala Phe Leu Pro Pro His Gln Gly Phe His Arg Phe
130                 135                 140

Leu Gly Ile Pro Tyr Ser His Asp Gln Gly Pro Cys Gln Asn Leu Thr
145                 150                 155                 160

Cys Phe Pro Pro Ala Thr Pro Cys Asp Gly Gly Cys Asp Gln Gly Leu
                165                 170                 175

Val Pro Ile Pro Leu Leu Ala Asn Leu Ser Val Glu Ala Gln Pro Pro
                180                 185                 190

Trp Leu Pro Gly Leu Glu Ala Arg Tyr Met Ala Phe Ala His Asp Leu
                195                 200                 205

Met Ala Asp Ala Gln Arg Gln Asp Arg Pro Phe Phe Leu Tyr Tyr Ala
210                 215                 220

Ser His His Thr His Tyr Pro Gln Phe Ser Gly Gln Ser Phe Ala Glu
225                 230                 235                 240

Arg Ser Gly Arg Gly Pro Phe Gly Asp Ser Leu Met Glu Leu Asp Ala
                245                 250                 255

Ala Val Gly Thr Leu Met Thr Ala Ile Gly Asp Leu Gly Leu Leu Glu
                260                 265                 270

Glu Thr Leu Val Ile Phe Thr Ala Asp Asn Gly Pro Glu Thr Met Arg
            275                 280                 285

Met Ser Arg Gly Gly Cys Ser Gly Leu Leu Arg Cys Gly Lys Gly Thr
290                 295                 300

Thr Tyr Glu Gly Gly Val Arg Glu Pro Ala Leu Ala Phe Trp Pro Gly
305                 310                 315                 320

His Ile Ala Pro Gly Val Thr His Glu Leu Ala Ser Ser Leu Asp Leu
                325                 330                 335

Leu Pro Thr Leu Ala Ala Leu Ala Gly Ala Pro Leu Pro Asn Val Thr
                340                 345                 350

Leu Asp Gly Phe Asp Leu Ser Pro Leu Leu Gly Thr Gly Lys Ser
                355                 360                 365

Pro Arg Gln Ser Leu Phe Phe Tyr Pro Ser Tyr Pro Asp Glu Val Arg
            370                 375                 380

Gly Val Phe Ala Val Arg Thr Gly Lys Tyr Lys Ala His Phe Phe Thr
385                 390                 395                 400

Gln Gly Ser Ala His Ser Asp Thr Thr Ala Asp Pro Ala Cys His Ala
                405                 410                 415
```

```
Ser Ser Ser Leu Thr Ala His Glu Pro Pro Leu Leu Tyr Asp Leu Ser
            420                 425                 430

Lys Asp Pro Gly Glu Asn Tyr Asn Leu Leu Gly Gly Val Ala Gly Ala
            435                 440                 445

Thr Pro Glu Val Leu Gln Ala Leu Lys Gln Leu Gln Leu Leu Lys Ala
            450                 455                 460

Gln Leu Asp Ala Ala Val Thr Phe Gly Pro Ser Gln Val Ala Arg Gly
465                 470                 475                 480

Glu Asp Pro Ala Leu Gln Ile Cys Cys His Pro Gly Cys Thr Pro Arg
                    485                 490                 495

Pro Ala Cys Cys His Cys Pro Asp Pro His Ala
            500                 505

<210> SEQ ID NO 3
<211> LENGTH: 489
<212> TYPE: PRT
<213> ORGANISM: Homo Sapiens
<220> FEATURE:
<221> NAME/KEY: FORMYLATION
<222> LOCATION: 51
<223> OTHER INFORMATION: C-alpha Formylglycine

<400> SEQUENCE: 3

Arg Pro Pro Asn Ile Val Leu Ile Phe Ala Asp Asp Leu Gly Tyr Gly
 1               5                  10                  15

Asp Leu Gly Cys Tyr Gly His Pro Ser Ser Thr Thr Pro Asn Leu Asp
                20                  25                  30

Gln Leu Ala Ala Gly Gly Leu Arg Phe Thr Asp Phe Tyr Val Pro Val
            35                  40                  45

Ser Leu Xaa Thr Pro Ser Arg Ala Ala Leu Leu Thr Gly Arg Leu Pro
50                  55                  60

Val Arg Met Gly Met Tyr Pro Gly Val Leu Val Pro Ser Ser Arg Gly
65                  70                  75                  80

Gly Leu Pro Leu Glu Glu Val Thr Val Ala Glu Val Leu Ala Ala Arg
                85                  90                  95

Gly Tyr Leu Thr Gly Met Ala Gly Lys Trp His Leu Gly Val Gly Pro
            100                 105                 110

Glu Gly Ala Phe Leu Pro Pro His Gln Gly Phe His Arg Phe Leu Gly
            115                 120                 125

Ile Pro Tyr Ser His Asp Gln Gly Pro Cys Gln Asn Leu Thr Cys Phe
            130                 135                 140

Pro Pro Ala Thr Pro Cys Asp Gly Gly Cys Asp Gln Gly Leu Val Pro
145                 150                 155                 160

Ile Pro Leu Leu Ala Asn Leu Ser Val Glu Ala Gln Pro Pro Trp Leu
                165                 170                 175

Pro Gly Leu Glu Ala Arg Tyr Met Ala Phe Ala His Asp Leu Met Ala
            180                 185                 190

Asp Ala Gln Arg Gln Asp Arg Pro Phe Phe Leu Tyr Tyr Ala Ser His
            195                 200                 205

His Thr His Tyr Pro Gln Phe Ser Gly Gln Ser Phe Ala Glu Arg Ser
            210                 215                 220

Gly Arg Gly Pro Phe Gly Asp Ser Leu Met Glu Leu Asp Ala Ala Val
225                 230                 235                 240

Gly Thr Leu Met Thr Ala Ile Gly Asp Leu Gly Leu Leu Glu Glu Thr
                245                 250                 255

Leu Val Ile Phe Thr Ala Asp Asn Gly Pro Glu Thr Met Arg Met Ser
            260                 265                 270
```

```
Arg Gly Gly Cys Ser Gly Leu Leu Arg Cys Gly Lys Gly Thr Thr Tyr
            275                 280                 285

Glu Gly Gly Val Arg Glu Pro Ala Leu Ala Phe Trp Pro Gly His Ile
        290                 295                 300

Ala Pro Gly Val Thr His Glu Leu Ala Ser Ser Leu Asp Leu Pro
305                 310                 315                 320

Thr Leu Ala Ala Leu Ala Gly Ala Pro Leu Pro Asn Val Thr Leu Asp
                325                 330                 335

Gly Phe Asp Leu Ser Pro Leu Leu Gly Thr Gly Lys Ser Pro Arg
            340                 345                 350

Gln Ser Leu Phe Phe Tyr Pro Ser Tyr Pro Asp Glu Val Arg Gly Val
        355                 360                 365

Phe Ala Val Arg Thr Gly Lys Tyr Lys Ala His Phe Phe Thr Gln Gly
    370                 375                 380

Ser Ala His Ser Asp Thr Thr Ala Asp Pro Ala Cys His Ala Ser Ser
385                 390                 395                 400

Ser Leu Thr Ala His Glu Pro Pro Leu Leu Tyr Asp Leu Ser Lys Asp
            405                 410                 415

Pro Gly Glu Asn Tyr Asn Leu Leu Gly Val Ala Gly Ala Thr Pro
        420                 425                 430

Glu Val Leu Gln Ala Leu Lys Gln Leu Gln Leu Lys Ala Gln Leu
            435                 440                 445

Asp Ala Ala Val Thr Phe Gly Pro Ser Gln Val Ala Arg Gly Glu Asp
    450                 455                 460

Pro Ala Leu Gln Ile Cys Cys His Pro Gly Cys Thr Pro Arg Pro Ala
465                 470                 475                 480

Cys Cys His Cys Pro Asp Pro His Ala
            485

<210> SEQ ID NO 4
<211> LENGTH: 489
<212> TYPE: PRT
<213> ORGANISM: Homo Sapiens

<400> SEQUENCE: 4

Arg Pro Pro Asn Ile Val Leu Ile Phe Ala Asp Asp Leu Gly Tyr Gly
1               5                   10                  15

Asp Leu Gly Cys Tyr Gly His Pro Ser Ser Thr Thr Pro Asn Leu Asp
            20                  25                  30

Gln Leu Ala Ala Gly Gly Leu Arg Phe Thr Asp Phe Tyr Val Pro Val
        35                  40                  45

Ser Leu Cys Thr Pro Ser Arg Ala Ala Leu Leu Thr Gly Arg Leu Pro
    50                  55                  60

Val Arg Met Gly Met Tyr Pro Gly Val Leu Val Pro Ser Ser Arg Gly
65                  70                  75                  80

Gly Leu Pro Leu Glu Glu Val Thr Val Ala Glu Val Leu Ala Ala Arg
                85                  90                  95

Gly Tyr Leu Thr Gly Met Ala Gly Lys Trp His Leu Gly Val Gly Pro
            100                 105                 110

Glu Gly Ala Phe Leu Pro Pro His Gln Gly Phe His Arg Phe Leu Gly
        115                 120                 125

Ile Pro Tyr Ser His Asp Gln Gly Pro Cys Gln Asn Leu Thr Cys Phe
    130                 135                 140

Pro Pro Ala Thr Pro Cys Asp Gly Gly Cys Asp Gln Gly Leu Val Pro
145                 150                 155                 160
```

```
Ile Pro Leu Leu Ala Asn Leu Ser Val Glu Ala Gln Pro Trp Leu
            165                 170                 175
Pro Gly Leu Glu Ala Arg Tyr Met Ala Phe Ala His Asp Leu Met Ala
            180                 185                 190
Asp Ala Gln Arg Gln Asp Arg Pro Phe Phe Leu Tyr Tyr Ala Ser His
            195                 200                 205
His Thr His Tyr Pro Gln Phe Ser Gly Gln Ser Phe Ala Glu Arg Ser
    210                 215                 220
Gly Arg Gly Pro Phe Gly Asp Ser Leu Met Glu Leu Asp Ala Ala Val
225                 230                 235                 240
Gly Thr Leu Met Thr Ala Ile Gly Asp Leu Gly Leu Leu Glu Glu Thr
                245                 250                 255
Leu Val Ile Phe Thr Ala Asp Asn Gly Pro Glu Thr Met Arg Met Ser
            260                 265                 270
Arg Gly Gly Cys Ser Gly Leu Leu Arg Cys Gly Lys Gly Thr Thr Tyr
            275                 280                 285
Glu Gly Gly Val Arg Glu Pro Ala Leu Ala Phe Trp Pro Gly His Ile
    290                 295                 300
Ala Pro Gly Val Thr His Glu Leu Ala Ser Ser Leu Asp Leu Leu Pro
305                 310                 315                 320
Thr Leu Ala Ala Leu Ala Gly Ala Pro Leu Pro Asn Val Thr Leu Asp
                325                 330                 335
Gly Phe Asp Leu Ser Pro Leu Leu Leu Gly Thr Gly Lys Ser Pro Arg
            340                 345                 350
Gln Ser Leu Phe Phe Tyr Pro Ser Tyr Pro Asp Glu Val Arg Gly Val
            355                 360                 365
Phe Ala Val Arg Thr Gly Lys Tyr Lys Ala His Phe Phe Thr Gln Gly
        370                 375                 380
Ser Ala His Ser Asp Thr Thr Ala Asp Pro Ala Cys His Ala Ser Ser
385                 390                 395                 400
Ser Leu Thr Ala His Glu Pro Pro Leu Leu Tyr Asp Leu Ser Lys Asp
                405                 410                 415
Pro Gly Glu Asn Tyr Asn Leu Leu Gly Gly Val Ala Gly Ala Thr Pro
            420                 425                 430
Glu Val Leu Gln Ala Leu Lys Gln Leu Gln Leu Leu Lys Ala Gln Leu
            435                 440                 445
Asp Ala Ala Val Thr Phe Gly Pro Ser Gln Val Ala Arg Gly Glu Asp
    450                 455                 460
Pro Ala Leu Gln Ile Cys Cys His Pro Gly Cys Thr Pro Arg Pro Ala
465                 470                 475                 480
Cys Cys His Cys Pro Asp Pro His Ala
                485
```

PRODUCTION AND PURIFICATION OF RECOMBINANT ARYLSULFTASE

CROSS REFERENCE TO RELATED APPLICATIONS

This application is the U.S. National Phase Application under 35 U.S.C. §371 of International Application No. PCT/DK2005/000068, filed on Jan. 30, 2005, which claims the benefit of priority to U.S. Provisional Application Ser. No. 60/540,061, filed on Jan. 30, 2004, and Danish Application No. PA 2004 00144, filed on Jan. 30, 2004.

FIELD OF INVENTION

The present invention relates to a process for production and purification of recombinant aryl sulfatase A (rASA) enzyme and the use of rASA obtained by this process for preventing or alleviating the symptoms related to Metachromatic leukodystrophy.

BACKGROUND OF THE INVENTION

Myelin Metabolism and Metachromatic Leukodystrophy

Metachromatic leukodystrophy (MLD) is caused by an autosomal recessive genetic defect in the lysosomal enzyme Arylsulfatase A (ASA), resulting in a progressive breakdown of membranes of the myelin sheath (demyelination) and accumulation of galactosyl sulphatide (cerebroside sulphate) in the white matter of both the central nervous system (CNS) and the peripheral nervous system. In histologic preparations, galactosyl sulphatide forms spherical granular masses that stain metachromatically. Galactosyl sulphatide also accumulates within the kidney, gallbladder, and certain other visceral organs and is excreted in excessive amounts in the urine.

Multiple sulfatase deficiency (MSD) is a rare form of MLD that also includes features of mucopolysaccharidosis (MPS). MSD is characterised by a decreased activity of all known sulfatases. The clinical phenotype of MSD combines features of MLD with that of MPS as a result of the impaired lysosomal catabolism of sulphated glycolipids and glycosaminoglycans.

Galactosyl sulfatide is normally metabolised by the hydrolysis of 3-O-sulphate linkage to form galactocerebroside through the combined action of the lysosomal enzyme arylsulfatase A (EC 3.1.6.8) (Austin et al. Biochem J. 1964, 93, 15C-17C) and a sphingolipid activator protein called saposin B. A profound deficiency of arylsulfatase A occurs in all tissues from patients with the late infantile, juvenile, and adult forms of MLD (see below). In the following, the arylsulfatase A protein will be termed "ASA" and the saposin B will be termed "Sap-B". A profound deficiency of ASA occurs in all tissues from patients with MLD.

ASA has been purified from a variety of sources including human liver, placenta, and urine. It is an acidic glucoprotein with a low isoelectric point. Above pH 6.5, the enzyme exists as a monomer with a molecular weight of approximately 100 kDa. ASA undergoes a pH-dependent polymerisation forming a dimer at pH 4.5. In human urine, the enzyme consists of two nonidentical subunits of 63 and 54 kDa. ASA purified from human liver, placenta, and fibroblasts also consist of two subunits of slightly different sizes varying between 55 and 64 kDa. As in the case of other lysosomal enzymes, ASA is synthesised on membrane-bound ribosomes as a glycosylated precursor. It then passes through the endoplasmic reticulum and Golgi, where its N-linked oligosaccharides are processed with the formation of phosphorylated and sulfated oligosaccharide of the complex type (Waheed A et al. Biochim Biophys Acta. 1985, 847, 53-61, Braulke T et al. Biochem Biophys Res Commun. 1987, 143, 178-185). In normal cultured fibroblasts, a precursor polypeptide of 62 kDa is produced, which translocates via mannose-6-phosphate receptor binding (Braulke T et al. J Biol Chem. 1990, 265, 6650-6655) to an acidic prelysosomal endosome (Kelly B M et al. Eur J Cell Biol. 1989, 48, 71-78).

The length (18 amino acids) of the human ASA signal peptide is based on the consensus sequence and a specific processing site for a signal sequence. Hence, from the deduced human ASA cDNA (EMBL GenBank accession numbers J04593 and X521151, see below) the cleavage of the signal peptide should be done in all cells after residue number 18 (Ala), resulting in the mature form of the human ASA. In the following, recombinant arylsulfatase A will be abbreviated rASA. the mature form of arylsulfatase A including the mature form of human ASA will be termed "mASA" and the mature recombinant human ASA will be termed "mrhASA".

A protein modification has been identified in two eukaryotic sulfatases (ASA and arylsulfatase B (ASB)) and for one from the green alga Volvox carteri (Schmidt B et al. Cell. 1995, 82, 271-278, Selmer T et al. Eur J Biochem. 1996, 238, 341-345). This modification leads to the conversion of a cysteine residue, which is conserved among the known sulfatases, into a 2-amino-3-oxopropionic acid residue (Schmidt B et al. Cell. 1995, 82, 271-278). The novel amino acid derivative is also recognised as $C_\alpha$-formylglycin (FGly). In ASA and ASB derived from MSD cells, the Cys-69 residue is retained. Consequently, it is proposed that the conversion of the Cys-69 to FGly-69 is required for generating catalytically active ASA and ASB, and that deficiency of this protein modification is the cause of MSD. Cys-69 is referred to the precursor ASA which has an 18 residue signal peptide. In the mASA the mentioned cysteine residue is Cys-51. Further investigations have shown that a linear sequence of 16 residues surrounding the Cys-51 in the mASA is sufficient to direct the conversion and that the protein modification occurs after or at a late stage of co-translational protein translocation into the endoplasmic reticulum when the polypeptide is not yet folded to its native structure (Dierks T et al. Proc Natl Acad Sci. 1997, 94, 11963-1196, Wittke, D. et al. (2004), *Acta Neuropathol. (Berl.)*, 108, 261-271).

Multiple forms of ASA have been demonstrated on electrophoresis and isoelectric focusing of enzyme preparations from human urine, leukocytes, platelets, cultured fibroblasts and liver. Treatment with endoglycosidase H, sialidase, and alkaline phosphatase reduces the molecular size and complexity of the electrophoretic pattern, which suggests that much of the charge heterogeneity of ASA is due to variations in the carbohydrate content of the enzyme.

Clinical Manifestations of MLD

The central nervous system consists of the brain and the spinal cord, and can be divided into white and grey matter. The white matter consists of nerve cells, and in MLD the damage occurs primary in the nerve cells. When the nerve cells are damaged, they can no longer conduct nerve impulses to muscles, skin and internal organs.

In cases of MLD, there is a defect in ASA activity affecting myelin metabolism. Lack of this enzyme in patients with MLD leads the degradation of myelin and to dysfunction of the nerve cells. A concomitant accumulation of special types of fat in the nerve cells is also observed in MLD. Three forms of the disease can be distinguished according to the three forms of the age of onset: Late-infantile, juvenile and adult (after the age of 20 years). The course of the disease varies in the different types. The type occurring in early childhood is the commonest, progresses most rapidly, and leads to pronounced handicapping and death.

In the infantile form of MLD there are several stages of the disease. The first stage is characterised by slack muscles (hypotonia) of the arms and legs. Walking deteriorates and the child needs support to walk. The picture is often complicated by disturbances of balance (ataxia) and weakened muscle reflexes. In the second stage, about 1-1½ years after the onset, the child can no longer stand, but it can still sit. The previous slack muscles become spastic. The disturbance of balance gets worse, and pain in the arms and legs is commonly observed. The disease progresses to the third stage after additional 3-6 months where the child has increasing paralysis of all four limbs and can no longer sit. The child gradually needs help with everything, vision is impaired, and movements become difficult.

The juvenile type of MLD starts between the ages of five and ten years. The progression is similar to the infantile type, but slower. Emotional lability and impaired vision may be the first symptoms of the disease. In the adult form of MLD the symptoms arise in the age after 20 years after normal development. The symptoms include cognitive and behavioural abnormalities.

Incidence of MLD

In Norway, about one child with MLD is born every year, i.e. a frequency of about 1:50.000. Similar results have been obtained in northern Sweden where the birth incidence rate for late infantile MLD in this population can be calculated to be about 1 per 40.000. Only one patient with juvenile MLD was born in the mentioned region during the same period. This demonstrates that the juvenile form of MLD is much more rare than the infantile form.

Animal Model of MDL

ASA knockout mice develop a disease, which corresponds to MLD (Hess et al. 1996, *Proc. Natl. Acad. Sci. U.S.A.* 93, 14821-14826, Gieselmann, V. et al. 1989 *J. Inherit. Metab. Dis.*, 21, 564-574, Gieselmann, V. et al. 2003, *Acta Paediatr. Suppl.*, 92, 74-79). Thus, they display storage deposits with a distribution and ultrastructure which is virtually identical to those in patients. The mice develop neurologic symptoms reminiscent of the human disease comprising gait disturbancies, reduced motor coordination abilities and hyperactivity (Hess et al. 1996, *Proc. Natl. Acad. Sci. U.S.A.* 93, 14821-14826, D'Hooge, R. et al. 2001, *Brain Res.*, 907, 35-43, Matzner, U. et al. 2002, *Gene Ther.*, 9, 53-63). The symptoms become apparent at around one year of age, but they do not reduce the life expectancy of the mice. The mild phenotype has been explained by the lack of widespread demyelination (Hess et al. 1996, *Proc. Natl. Acad. Sci. U.S.A.* 93, 14821-14826, Coenen, R. et al. 2001, *Acta Neuropathol. (Berl.).*, 101, 491-498, Wittke, D. et al. 2004, *Acta Neuropathol. (Berl.)*, 108, 261-271). The limited demyelination in mice can be attributed to the short life span, which does not allow for the development of cellular dysfunctions, causative for demyelination. The ASA knock out mice therefore represent an appropriate animal model particularly for investigating therapeutic interventions in an early stage of the human disease.

Existing Diagnosis of MLD

In order to diagnose MLD, examination of spinal fluid, urine, various blood tests, and analysis of the ASA activity can be carried out. Deficiency of ASA activity in material from patients with MLD (e.g. peripheral leukocytes and cultured skin fibroblasts) can be investigated. Analysis of the urine from patients with MLD can indicate a defect at the level of myelin metabolism but this is a less reliable source for diagnostic assays because the urinary enzyme level is normally highly variable. Excessive amounts of sulpatide excreted in the urine and metachromatic granules in the urinary sediment are observed. Furthermore, normal x-rays and computer tomography (CT) of the head may be carried out. Prenatal diagnosis appears to be possible by measuring ASA activity in cultured cells from amniotic fluid or chorionic villus cells. Cerebroside sulfate loading of such cells can also be used and is the method of choice if the pseudodeficiency gene is also present in the family.

Existing Treatment of MLD

There are relatively few treatment options for MLD. Bone Marrow Transplantation (BMT) has been used in the treatment of more than 20 patients with MLD (for instance Bayever E et al. Lancet 1985, 2, 471-473), and it appears that BMT slows the progression of symptoms, but benefits of the treatment are not seen for several months. In most late infantile patients, symptoms are progressing rapidly by the time of diagnosis, and the risks of the procedure tend to outweigh the possible benefits. In instances in which the diagnosis can be made presymtomatically and a well-matched donor is available, BMT may be a reasonable approach. Moreover, reported results suggest that BMT is efficacious only in MLD patients with high residual activity or when performed in presymptomatic stages in the late infantile form probably because of the rapid progression of the disease. The perspective of using bone marrow transplantation is further limited by the fact that it only reduces symptoms in the central nervous system and that supplementary treatment is required in order to alleviate symptoms in the peripheral nervous system.

Cell culture models suggest that cysteine protease inhibitor treatment (von Figura K et al. Am J Hum Genet 1986, 39, 371-382), thiosulfate treatment (Eto Y et al. Biochem Biophys Res Commun 1982, 106, 429-434), enzyme replacement (Porter M T Science 1971, 172 (989), 1263-1265), and gene replacement therapies (Sangalli A et al. Hum Gene Ther 1998, 9, 2111-2119) could be effective. Several possible gene therapy approaches have been suggested.

In one of these approaches an implanted polymer-encapsulated xenogenic transduced cell line secreting the ASA enzyme is used. This approach has previously been used for the treatment of other neurological disorders such as Amyotrophic Lateral Sclerosis and Parkinson disease. A cathetered devise, containing around 106 genetically modified cells surrounded by a semipermeable membrane, is suggested to be implanted in the ventricular space, providing slow continuous release of ASA directly in cerebral spinal fluid. For this gene transfer technique C2C12 mouse myoblast cells are used (Degion et al. Hum Gene Ther 1996, 7, 2135-2146). The semipermeable membrane prevents immunologic rejection of the cells and interposes a physical barrier between cells and host. Moreover, the device and the cells may be retrieved in the event of side effect due to the ASA administration.

In another approach, ASA genes are directly delivered into the brain by the use of recombinant adenovirus (Ohashi et al. Acta Paediatr Jpn. 1996, 38, 193-201). It was shown that the recombinant adenovirus (Adex1SRLacZ) was able to transduce the oligodendrocytes very efficiently. Despite the fact that gene therapy have led to satisfactory increases in tissue enzyme levels, the success of this approach appears limited, as studies have revealed no significant decline in the sulfatide levels in response to the increased enzyme levels in important tissues such as the kidney. The disappointing results may be caused by insufficient translocation of arylsulfatase A to the lysosomes.

Conventional Enzyme Replacement Therapy based on systemic infusion of arylsulfatase A would clearly provide cost-efficient treatment of MLD with little inconvenience and low risk of complications to the patients. As opposed to gene therapy, enzyme replacement therapy would also not raise any ethical questions. The application of enzyme replacement therapy in the treatment of MLD has, however, been hampered by the difficulties in preparing large amounts of arylsulfatase A with sufficient specific activity and at the quality required for clinical applications. Furthermore, enzyme replacement therapy is traditionally considered efficient only in reducing sulfatide levels in the peripheral nervous system, since arylsulfatase due to its size is unlikely to access the central nervous system.

SUMMARY OF THE INVENTION

In essence, the inventive concept of the present invention is based on the finding that isolation of recombinant arylsulfatase A from a mammalian cell system, which is cultured in a system allowing for continuous cell propagation, and purification by a series of specific chromatography steps implies a number of important advantages, including an increased expression level and yield of recombinant protein as well as increased purity of the rASA obtained. Furthermore, as opposed to batch fermentation, production in a continuos process may facilitate a tight control of production parameters so as to ensure a product of high and uniform quality, including correct post translational modification and functionality of the resulting enzyme. Such purified recombinant arylsulfatase A is suitable for use in pharmaceutical preparations and may be produced in a form that will be able to cross the blood-brain barrier.

Accordingly, the present invention pertains to a process for continuos production of recombinant arylsulfatase A in a cell culture system, the process comprising:
i) culturing a mammalian cell capable of producing rASA in liquid medium in a system comprising one or more bio-reactors;
ii) concentrating, purifying and formulating the rASA by a purification process comprising one or more steps of affinity chromatography and/or ion exchange chromatography.

In a preferred embodiment, the concentration and purification process of ii) comprises the following steps:
I) concentrating rASA present in the liquid medium by tangential flow filtration;
II) loading the rASA containing supernatant obtained in step I on an equilibrated chromatography column and eluting one or more fraction(s) containing rASA;
III) loading the fraction(s) from step II on another equilibrated chromatography column and eluting one or more fraction(s) containing rASA;
IV) purifying rASA present in the fraction(s) from step III by tangential flow filtration;
V) polishing the preparation of rASA from step IV in one or two or more successive steps, each step comprising loading the preparation on an equilibrated chromatography columns and eluting one or more fraction(s) containing rASA;
VI) passing the fraction(s) from step V through a viral reduction filter;
VII) formulating the fraction(s) from step VI in order to obtain a preparation of rASA in a suitable formulation buffer;
VIII) optionally filling the formulated preparation of rASA into a suitable container and freeze-drying the sample.

Other aspects of the invention provides a pharmaceutical composition comprising rASA, which is efficiently endocytosed via the mannose-6-phosphate receptor pathway in vivo as well as a rASA for use as a medicament and use of a rASA for the manufacture of a medicament for reducing the galactosyl sulphatide levels within target cells in the peripheral nervous system and/or within the central nervous system in a subject.

A final aspect of the invention provides a method of treating a subject in need thereof, said method comprising administering to said subject a pharmaceutical composition comprising a rASA and thereby obtaining a reduction in the galactosyl sulphatide levels in target cells within said subject.

DETAILED DESCRIPTION OF THE INVENTION

By the term "enzyme" is herein meant either the relevant enzyme which is substituted as it is, or an enzymatically equivalent part or analogue thereof. One example of an enzymatically equivalent part of the enzyme could be a domain or sub-sequence of the enzyme, which includes the necessary catalytic site to enable the domain or sub-sequence to exert substantially the same enzymatic activity as the full-length enzyme.

An example of an enzymatically equivalent analogue of the enzyme could be a fusion protein which includes the catalytic site of the enzyme in a functional form, but it can also be a homologous variant of the enzyme derived from another species. Also, completely synthetic molecules, which mimic the specific enzymatic activity of the relevant enzyme, would also constitute "enzymatic equivalent analogues".

A "contaminant" is a material that is different from the desired polypeptide product. The contaminant may be a variant of the desired polypeptide (e.g. a deamidated variant or an amino-aspartate variant of the desired polypeptide) or another polypeptide, nucleic acid, endotoxin etc.

By "purifying" a polypeptide from a composition comprising the polypeptide and one or more contaminants is meant increasing the degree of purity of the polypeptide in the composition by removing (completely or partially) at least one contaminant from the composition. A "purification step" may be part of an overall purification process resulting in a composition comprising at least about 20% by weight of the polypeptide of interest, based on total weight of the composition, preferably at least about 30% by weight.

"Treatment" refers to both therapeutic treatment and prophylactic or preventative measures. Those in need of treatment include those already with the disorder as well as those in which the disorder is to be prevented.

The present invention relates to a strategy for the treatment of MLD according to which recombinant aryl sulfatase A (rASA) is administered to a subject, for instance by systemic administration, in order to reach the relevant target cells. While basically all cells in the brain are deficient of the ASA, cell types of particular interest are oligodendrocytes or oligodendroglia that are responsible for myelination of neurons within the central nervous system and neuronal cells. Schwann cells, which are responsible for myelination of the peripheral nerve system (PNF), are one of the main target cells outside the central nervous system (BBB).

It has previously been proposed to apply a number of different delivery techniques rASA enzyme in order to facilitate its transport across the BBB and/or cellular membranes. Examples of such techniques are briefly described in the following paragraphs:

1) Use of mannose-6-phosphate tags produced as post-translational modifications by a combined action of phosphotransferases and phosphoglycosidases in the Golgi apparatus when the rASA is expressed in a mammalian cell system. The tagged version of the enzyme will have the capacity to cross the cellular membrane via mannose-6-phosphate receptor uptake.

2) Peptides and proteins as vehicles for passage of rASA to the target cells by passage over cell membranes and/or the BBB:

A number of earlier studies in animals have shown that certain proteins and/or peptides may act as vehicles for passage of BBB. For instance proteins modified by the insulin fragment (Fukuta et al. Phaomacol Res 11: 1681-1688) or antibodies to the transferrin receptor (Friden et al. Proc Natl Acad Sci USA 88: 4771-4775) can pass the blood-brain barrier. Also proteins modified by coupling to polyamines (Poduslo and Curran. J Neurochem 66: 1599-1606) have been reported to pass the blood-brain barrier.

Of particular relevance to the present invention are membrane-disrupting or protein-transducing domains, where the focus has been on short peptides 10-30 residues in length. When covalently attached to protein molecules these peptides can transport the molecule across the blood-brain barrier and also across cellular membranes in general (Schwarze et al., Trends Cell Biol. 2000; 10(7): 290-295; Lindgren et al., Trends Pharmacol. Sci. 2000; 21(3): 99-103). A modified rASA molecule containing such peptide sequences can be produced by expression techniques. The protein transduction process is not cell type specific and the mechanism by which it occurs is not fully elucidated, however, it is believed that it takes place by some sort of membrane perturbation and penetration process that is receptor independent. A partially unfolded state of the molecule may facilitate the process but is not essential.

Protein transducing domains are generally derived from viruses or other non-human protein molecules (and have the potential to be immunogenic). Examples of such domains include:

- The 11 residue basic peptide from the HIV TAT protein-YGRKKRRQRRR (Schwarze et al., Trends Cell Biol. 2000; 10(7): 290-295). This peptide binds to extracellular matrix-associated heparan sulfate proteoglycans (HSPGs) and transports a wide variety of large and small molecules across cellular membranes. The initial entry may be vesicular and the transduced molecule comes back out of the cell when the outside concentration decreases. The peptide can be present anywhere in the molecule as long as it is exposed, even in the reverse order of amino acid residues. All humans have low titer innate antibodies to this basic domain of TAT that are of the IgM isotype (Schwarze et al., Trends Cell Biol. 2000; 10(7): 290-295).
- A synthetic version of TAT-YARAAARQARA that confers more alpha-helicity and amphipathic nature to the sequence (Ho et al., Cancer Res. 2001; 61(2):474-477). This peptide is considerably more efficient than TAT and it also has documented effects in vivo. The peptide has no classical nuclear localization signal present, as is the case with the natural TAT sequence and it presents a different immunologic epitope.
- A synthetic leader peptide composed of poly -R or a mixture of basic -R and -K residues in combination with other amino acids.
- Peptides based on hydrophobic signal sequence moieties from either beta-3 integrin or Kaposi's sarcoma FGF (Dunican et al. Biopolymers 2001; 60(1): 45-60). These are termed membrane permeable sequences and are hydrophobic rather than basic sequences. They are derived from human proteins so their immunogenic potential may be low.

Other tags may have the capacity to direct the enzyme into the relevant target cells by carrier mediated transport. These tags may be a peptide or protein or the functional part of a peptide or protein which has affinity for a specific receptor. Examples of such receptors could be the nerve growth factor (NGF) or brain derived neurotropic factor (BDNF) receptors.

One way of ensuring a more efficient transport of proteins across the BBB would be to use specific transport systems. An example of such a system is the transferrin receptor which normal functions to transport transferrin and melanotransferrin across the BBB (Rothenberger et al., Brain Res. 1996, 712, 117-21; Demeule et al., J Neurochem 2002, 83, 924-33). When attached to the rASA a full length or synthetic protein or peptide with affinity for the receptor will "pull" the modified rASA over the blood-brain barrier. An alternative approach is the use of receptor mediated transfer of specific cytokines over the blood-brain barrier exemplified by the transport of TNF-alpha by p55 and p75 receptor (Pan et al., Exp Neurol. 2002 April; 174(2):193-200; Pan et al., Arch Physiol Biochem. 2001 October; 109(4):350-353).

3) Toxins as vehicles for passage rASA to the target cells by passage over cell membranes and/or the BBB:

Different bacteria, plants and animals produce toxins. Toxins have many different targets such as the gut (enterotoxins), nerves or synapses (neurotoxins). Toxins can traverse cell membranes via receptor mediated processes and the embodiment of the present invention is to use toxins as vehicles to passage rASA to the target cells over cellular membranes and/or the BBB. Use of toxins for delivery of therapeutics in the treatment of Metachromatic Leukodystrophy (MLD) is of particular relevance since preferred target cells of toxins are cells in the central nervous system and/or the peripheral nervous system. Of practical considerations and for safety reasons only the amino acid peptide pertaining to the translocation over cellular membranes and/or the BBB of the toxin is used.

Diphtheria Toxin (DT), from the *Corynebacterium Diptheriae* is a good example of a toxin which may be used as a vehicle. Bacterial toxins exhibit a wide range of toxicities and they fall into groups by structure and function. The toxin binds to a target cell and enters the cell via a receptor, and is reduced to separate fragments. The processed toxin can be divided into the following 3 domains: The catalytic domain (C), the receptor domain (R), and the translocation domain (T).

A main aspect of the present invention relates to a method for production and purification of recombinant arylsulfatase A or an enzymatic equivalent part or analogue thereof, which can be used in the prevention or treatment of MLD and/or the symptoms related to this disorder. The success of this strategy, however, is highly dependent on the availability of preparations of rASA that are of high purity and uniform quality. It is therefore also within the scope of the invention to provide a quality of rASA which can act as a catalyst in the intracellular metabolism of galactosyl sulfatide to galactocerebroside and thereby substitute for the deficient ASA, which is one of the characteristics of MLD. In a further perspective, it is within the scope of the invention to provide a recombinant form of arylsulfatase A, which is capable of crossing the blood brain barrier and also a form of rASA, which possesses specific tags for entry into target cells within the brain. A preferred embodiment of the invention, however, is the production and purification of rASA with a pattern of mannose-6-phosphate tags that allows the enzyme to enter its target cells by mannose-6-phosphate receptor mediated entry. In particular, it is an object of the present invention to provide a rASA, which is efficiently endocytosed in vivo via the mannose-6-phosphate pathway.

Mature human ASA has three putative N-glycosylation sites i.e. Asn158, Asn184, and Asn350, which can form the mannose-6-P tag. Asn158, Asn184, and Asn350 are referred to the precursor ASA which has an 18 residue signal peptide. In the mature ASA the mentioned asparagine residues are Asn140, Asn166, and Asn332, respectively. Only two of the N-glycosylation sites (Asn140 and Asn332) undergoes phosphorylation and can acquire the correct mannose-6-P tag and the mannose-6-P synthesis at these two sites via two distinct enzymatic steps.

Suitable host cells for the expression of glycosylated polypeptide are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CVI line transformed by SV40 (COS-7); human embryonic kidney line (293 or 293 cells subcloned for growth in suspension culture); baby hamster kidney cells (BHK); Chinese hamster ovary cells/-DHFR (CHO); mouse Sertoli cells (TM4); monkey kidney cells (CVI); African green monkey kidney cells (VERO-76); human cervical carcinoma cells (HELA); canine kidney cells (MDCK); buffalo rat liver cells (BRL 3A); human lung cells (W138); human liver cells (Hep G2, HB 8065); mouse mammary tumor (MMT 060562); TRI cells; MRC 5 cells; FS4 cells; and a human hepatoma line (Hep G2).

The present invention provides a process for production of rASA in a continuous cell culture system, the process comprising:
i) culturing a mammalian cell capable of producing rASA in liquid medium in a system comprising one or more bio-reactors;
ii) concentrating, purifying and formulating the rASA by a purification process comprising one or more steps of affinity chromatography and/or ion exchange chromatography.

More specifically, the method comprises the propagation of a mammalian cell line capable of synthesising rASA in a culture system, which allows for continuous cell propagation and the subsequent extraction and purification of the resulting rASA in a series of chromatography steps. When presented in a brief outline, the process for production and purification of rASA may comprise one or more of the following general steps:
A. Culturing of mammalian cells capable of producing rASA in a cell culture system allowing for continuous cell propagation.
B. Concentration of rASA from the supernatant and purification of rASA by a series of chromatography steps wherein the proteins are separated according to their net charge or affinity for ligands, supplemented by filtration procedures based on separation of the proteins according to size.
C. Formulation, filling, and freeze-drying.
of rASA in a cell culture system allowing the propagation of cell cultures over extended periods of time.

It is preferred that the cell comprises a nucleic acid sequence, which encodes:
(a) the amino acid sequence of SEQ ID NO:2;
(b) a portion of the sequence in (a), which is enzymatically equivalent to recombinant human arylsulfatase A
(c) an amino acid sequence analogue having at least 75% sequence identity to any one of the sequences in (a) or (b) and at the same time comprising an amino acid sequence, which is enzymatically equivalent to recombinant human arylsulfatase A.

In the present context, an amino acid sequence or a portion of an amino acid sequence which is a polypeptide capable of hydrolysing an amount of the arylsulfatase A substrate pNCS at 37° C. a rate corresponding to a specific activity of at least 20 U/mg polypeptide (preferably 50 U/mg polypeptide) when determined in an assay for measuring arylsulfatase A activity as described in example 1 of the present application, and/or a polypeptide, which is capable of hydrolysing at least 40% of labelled arylsulfatase A substrate, fx. $^{14}C$ palmitoyl sulfatide, loaded into MLD fibroblasts, when assayed by incubation at a dose level of 25 mU/ml in an assay as described in example 2 of the present invention.

Equally preferred is a process incorporating a cell, which comprises
(a) the nucleic acid sequence of SEQ ID NO:1;
(b) a portion of the sequence in (a), which encodes an amino acid sequence, which is enzymatically equivalent to recombinant human arylsulfatase A
(c) a nucleic acid acid sequence analogue having at least 75% sequence identity to any one of the sequences in (a) or (b) and at the same time encoding an amino acid sequence, which is enzymatically equivalent to recombinant human arylsulfatase A It may be preferred that the degree of sequence identity between the nucleic acid sequence comprised within the cell according to the invention and SEQ ID NO: 1 is at least 80%, such as at least 85%, at least 90%, at least 95%, at least 97%, at least 98%, or at least 99%. It may be equally preferred that the degree of sequence identity between the amino acid sequence encoded by the above mentioned nucleic acid sequence and SEQ ID NO: 2 is at least 80%, such as at least 85%, at least 90%, at least 95%, at least 97%, at least 98%, or at least 99%.

For the purpose of the present invention it is preferred that the arylsulfatase A is a recombinant enzyme, particularly preferred is recombinant human arylsulfatase A (rhASA).

It is preferred that rASA is produced in mammalian cell or cell line and that said mammalian cell or cell line produces a glycoform of rASA, which is efficiently endocytosed in vivo via the mannose-6-phosphate receptor pathway. Specifically, the preferred glycoform of rASA comprises an amount of exposed mannose-6-phosphate, which allows efficient endocytosis of rASA in vivo via the mannose-6-phosphate pathway.

It has previously been contemplated that expression of rASA in either CHO, COS and BHK cells ensures correct mannose-6-phosphate tagging on the molecule, which in turn ensures efficient receptor mediated uptake (Stein et al. J Biol Chem. 1989, 264, 1252-1259). While this may be true for endocytosis in vitro, the present inventors have observed a markedly increased in vivo endocytosis of rASA produced in CHO cells as compared to the endocytosis in vivo of rASA produced in BHK and COS cells. The efficient endocytosis of the enzyme is a prerequisite for obtaining the desired correction of the sulfatide levels in the peripheral nervous system and in visceral organs of the body. Therefore, it is preferred that at least one of the produced glycoforms of rASA is similar to a glycoform produced in CHO cells.

The inventors have further observed that production must be optimised in order to ensure correct post translational processing of the enzyme. In particular, production of the enzyme at a too high rate and intensity leads to a product of sub-optimal quality in terms of glycosylation, phosphorylation and formylation. Therefore, it is further preferred that the production of arylsulfatase A or its equivalent occurs at a rate and under conditions which result in a product comprising a glycoform of the enzyme having four glycosylation intermediates as determined by MALDI-TOF analysis after treatment with low concentrations of PNGase F. Further preferred are conditions under which the acquired carbohydrate moieties of the arylsulfatase A or its equivalent have a combined mass of 3-8 kDa. It is also preferable that production of arylsulfatase A or its equivalent occurs at a rate and under conditions which result in a product comprising a glycoform of the enzyme having a pattern of high mannose and/or complex oligosaccharides, which are phosphorylated so as to allow efficient endocytosis of the enzyme via mannose-6-phosphate receptor mediated entry.

As explained the post translational modification of the cysteine residue in position 51 in the mature human arylsulfatase A is critical for the activity of the enzyme. Accordingly, in a preferred embodiment of the present invention production of the arylsulfatase A or its equivalent occurs at a rate and under conditions, which result in a product comprising an isoform of the enzyme in which the amino acid corresponding to Cys-69 in SEQ ID NO: 2 is converted to Formylglycine, corresponding to Fgly-51 in SEQ ID NO: 3. SEQ ID NO: 4 represents mature human arylsulfatase A after cleavage of the 18 amino acid signal peptide but prior to modification of C-51.

This embodiment thus relates to a process, wherein the arylsulfatase A produced or its enzymatical equivalent is selected from the group consisting of
(a) the amino acid sequence of SEQ ID NO:3;
(b) a portion of the sequence in (a), which is enzymatically equivalent to recombinant human arylsulfatase A
(c) an amino acid sequence analogue having at least 75% sequence identity to any one of the sequences in (a) or (b) and at the same time being enzymatically equivalent to recombinant human arylsulfatase A.

It may be preferred that the degree of sequence identity between the enzyme produced according to the invention and SEQ ID NO: 3 or SEQ ID NO: 4 is at least 80%, such as at least 85%, at least 90%, at least 95%, at least 97%, at least 98%, or at least 99%.

The term 'sequence identity' indicates a quantitative measure of the degree of homology between two amino acid sequences or between two nucleic acid sequences of equal length. If the two sequences to be compared are not of equal length they must be aligned to give the best possible fit, allowing the insertion of gaps or, alternatively, truncation at the ends of the polypeptide sequences or nucleotide sequences. The sequence identity can be calculated as $(N_{ref} - N_{dif}) 100 / N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}=2$ and $N_{ref}=8$). A gap is counted as non-identity of the specific residue(s), i.e. the DNA sequence AGTGTC will have a sequence identity of 75% with the DNA sequence AGTCAGTC ($N_{dif}=2$ and $N_{ref}=8$).

In all polypeptide or amino acid based embodiments of the invention the percentage of sequence identity between one or more sequences is based on alignment of the respective sequences as performed by clustalW software (http:/www.ebi.ac.uk/clustalW/index.html) using the default settings of the program. These settings are as follows: Alignment=3Dfull, Gap Open 10.00, Gap Ext. 0.20, Gap separation Dist. 4, Protein weight matrix: Gonnet. With respect to the nucleotide-based embodiments of the invention, the percentage of sequence identity between one or more sequences is also based on alignments using the clustalW software with default settings. For nucleotide sequence alignments these settings are: Alignment=3Dfull, Gap Open 10.00, Gap Ext. 0.20, Gap separation Dist. 4, DNA weight matrix: identity (IUB).

The biological activity and the effects of the enzyme in vivo requires that an adequate amount of the enzyme has acquired a glycosylation pattern as described above and has been modified post translationally at position 51. It is therefore critical that at least 50%, 60%, 70%, 80%, 90%, 95% or 98% of the enzyme produced is of the above described glycoform/isoform.

It is preferred that the mammalian cells used in the process according to the invention are of human or primate origin. In a currently most preferred embodiment, the mammalian cells are CHO cells and it is further preferred that these cells are are CHO-DG44 cells. In another preferred embodiment a human cell line is used.

In a preferred embodiment of the present invention the cells used for production of rASA comprise a nucleic acid sequence which encodes an amino acid sequence according to SEQ ID NO: 2. In a further preferred embodiment, the rASA is encoded by SEQ ID NO: 1.

In the process according to the invention, protein purification is simplified since in the system described, rASA is secreted into the medium.

The cell culture system is based on one or more conventional bioreactors, which are connected to a source of fresh medium and to a system in which the cells can be harvested and the medium collected. A part of this system may be a cell retention device. Preferably these different parts of the system are interconnected in a way so that fresh medium can be added and medium which contains cells together with one or more biosynthetic products secreted from the cells can be collected on a continuous basis. Mannose-6-phosphate tagged mASA is secreted into the medium and, optionally, purification of rASA is facilitated by the use of ammonium salts (NH$_4$Cl) in the fermentation step.

One immediate advantage of this system as compared to a batch system is to allow for an effective production phase extending over longer time. It is therefore within the scope of the present invention to operate the system continuously over a period extending over one week, preferably two weeks, more preferably 3 weeks, even more preferably 4 weeks. The cells can be propagated at 37° C., however it is preferred to reduce the temperature to 33-35° C. when the plateau of the production phase is reached in order to increase the productivity of the system.

In one preferred embodiment of the invention, this system is based on the use of bioreactors with a volume of 1 L. Alternatively, bioreactors with a volume of 5 L or bioreactors capable of holding approximately 4 L of medium may be preferred. As it can be appreciated, however, the system is also intended as a basis for production of rASA with a larger capacity and thereby scale-up to large scale production as will be required in the pharmaceutical industry. Other preferred embodiments of the present invention are therefore bioreactors or fermentors with a capacity of 10 L, more preferably 50 L, 200 L, 1000 L. Currently, a bioreactor volume of 100 L, 400 L or 700 L is preferred. It is further preferred that the production phase extends for at least two weeks an, additionally, a process wherein 1 to 2 or even up to 4 reactor volumes of cell culture are harvested each day is contemplated.

In a preferred embodiment, the process according to the invention is performed using one or more bio-reactors that are equipped with cell retention devices and re-circulation loops.

The cell line used to produce the polypeptide of this invention may be cultured in a variety of media. Commercially available media such as Ham's F 10 (Sigma), Minimal Essential Medium ((MEM), (Sigma), RPMI-1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the cell line selected for expression of the enzyme, and will be apparent to the person of ordinary skill in the art.

In order to control the levels of unwanted proteins in the culture medium it is preferred, however, that the system is developed for culturing the cells in a serum-free medium which only contains recombinant human proteins that have molecular weights less than 10 kDa. The total protein concentration is from less than 10 mg/ml to less then 100 ug/ml, such as less than 1 mg/ml. In a preferred embodiment of the invention the cell line is cultured in serum-free Excell 302 medium supplemented with insulin-like growth factor-1 (IGF-1).

A starting material for the purification process may be a crude cell extract but preferably the rASA is secreted by the cells and is subsequently purified from the cell culture supernatant. The purification process may comprise but is not limited to the following general steps:

1) concentration and diafiltration step,
2) capture step (ion-exchange chromatography),
3) intermediate purification step (chromatography),
4) acidic filtration
5) polishing (chromatography),
6) virus removal,
7) formulation,
8) filling and freeze-drying.

In addition, one or more buffer exchange steps may be incorporated and, optionally, the concentration and diafiltration step may be omitted. This is feasible in particular if the concentration and purification process of the above mentioned step ii) comprises one or more steps of Expanded Bed Chromatography. Preferably the Expanded Bed Chromatography step is performed as the capture step.

Furthermore it is preferred that the concentration and purification process of (ii) comprises a polishing step including a passive step, wherein the arylsulfatase A passes through an affinity chromatography resin or membrane and/or a cation chromatography resin or membrane, and an active step, wherein the arylsulfatase A is detained within and subsequently eluted from an anion exchange membrane or resin. This combination of passive and active steps is suggested from the surprising finding that whereas most contaminating proteins binds to an anion exchange matrix at pH values less than 5.8, preferably at pH values around 5.5-5.7, arylsulfatase A will pass the cation exchange matrix and subsequently bind to an anion exchange resin. It is believed that a change in the structure of the enzyme from a dimer to an octamer at pH values below 5.8 is responsible for this surprising effect. This change in structure has physiological relevance since the enzyme is active in the lysosomes at low pH.

In an embodiment of the invention, the concentration and purification process of the above mentioned step ii) comprises the following steps:

I) concentrating rASA present in the liquid medium by tangential flow filtration;
II) loading the rASA containing supernatant obtained in step I on an equilibrated chromatography column and eluting one or more fraction(s) containing rASA;
III) loading the fraction(s) from step II on another equilibrated chromatography column and eluting one or more fraction(s) containing rASA;
IV) purifying rASA present in the fraction(s) from step III by tangential flow filtration;
V) polishing the preparation of rASA from step IV in one or two or more successive steps, each step comprising loading the preparation on an equilibrated chromatography columns and eluting one or more fraction(s) containing rASA;
VI) passing the fraction(s) from step V through a viral reduction filter;
VII) formulating the fraction(s) from step VI in order to obtain a preparation of rhASA in a suitable formulation buffer;
VIII) optionally filling the formulated preparation of rASA into a suitable container and freeze-drying the sample.

It is contemplated that it may not be necessary to perform all the general and specific steps of the purification process as outlined above. One could for instance omit the formulation step as well as the filling and freeze-drying if the aim is not to provide a final product suitable for medicinal use.

As mentioned step I of the above outlined process may be omitted. Therefore it may be preferred that the concentration and purification process of ii) comprises the following steps:

II) contacting an arylsulfatase A containing supernatant on an equilibrated chromatography column and eluting one or more fraction(s) containing arylsulfatase A;
III) loading the fraction(s) from step II on another equilibrated chromatography column and eluting one or more fraction(s) containing arylsulfatase A;
IV) buffer exchange of the arylsulfatase A present in the fraction(s) from step III by tangential flow filtration;
V) polishing the preparation of arylsulfatase A from step IV in one or two or more successive steps, each step comprising loading the preparation on an equilibrated chromatography columns and eluting one or more fraction(s) containing arylsulfatase A;
VI) passing the fraction(s) from step V through a viral reduction filter;
VII) formulating the fraction(s) from step VI in order to obtain a preparation of arylsulfatase A in a suitable formulation buffer;
VIII) optionally filling the formulated preparation of arylsulfatase A into a suitable container and freeze-drying the sample.

In step I) of the process the concentration of rASA in the material is increased with the purpose of obtaining a solution of rASA in a volume, which is sufficiently small to be conveniently loaded onto the chromatography columns of the subsequent steps of the purification procedure. Preferentially the rASA is concentrated 5-50 times in volume, more preferentially 10-20 times by tangential flow filtration. It is obvious to the person of ordinary skill in the art that various different membranes with different nominal weight cut-offs can be used. Nominal weight cut-offs may thus be in the range of 10 to 100 kDa, however, in the present application it is preferred that a 30 KDa membrane is used.

An additional part of step I) includes diafiltration of the rASA containing solution, which is performed in order obtain a solution of rASA in a buffer suitable as a loading buffer in the subsequent chromatography steps. Diafiltration is performed using commercially available equipment and following a standard procedure well known to a person skilled in the art.

In a preferred embodiment step II in this process is based on anion exchange chromatography. Anionic resins will generally bind proteins with a net positive charge. Negatively charged or neutral proteins will pass through the matrix, and positively charged proteins (with varying degrees of charge) can be discriminately eluted by gradually changing (in a linear fashion or stepwise linear fashion) the counterion charge of the system with a salt.

As will be known by the person skilled in the art, ion exchangers may be based on various materials with respect to the matrix as well as to the attached charged groups. For example, the following matrices may be used, in which the materials mentioned may be more or less crosslinked: agarose based (such as Sepharose CL-6B®, Sepharose Fast Flow® and Sepharose High Performance®), cellulose based (such as DEAE Sephacel®), dextran based (such as Sephadex®), silica based and synthetic polymer based. For the anion exchange resin, the charged groups which are covalently attached to the matrix may e.g. be diethylaminoethyl (DEAE), quaternary aminoethyl (QAE), and/or quaternary ammonium (Q). In a preferred embodiment of the present process, the anion exchange resin employed is a DEAE Sepharose column, and more specifically, it may be a DEAE Sepharose Fast Flow®, or a DEAE Streamline column, but other anion exchangers can be used.

The ion exchange resin is prepared according to known methods. Usually, an equilibration buffer, which allows the resin to bind its counterions, is passed through the ion exchange resin prior to loading the composition comprising the polypeptide and one or more contaminants onto the resin. Conveniently, the equilibration buffer is the same as the loading buffer, but this is not required.

The aqueous solution comprising the rASA and contaminant(s) is loaded onto the anionic resin using a loading buffer that has a salt concentration and/or a pH such that the polypeptide and the contaminant bind to the anion exchange resin. The resin is the washed with one or more column volumes of loading buffer followed by one or more column volumes of wash buffer wherein the salt concentration is increased. Finally, the rASA is eluted by further increasing the salt concentration. Optionally, elution of the enzyme may also be mediated by gradually or stepwise decreasing the pH. The fractions containing rASA activity are collected and combined for further purification.

It is apparent to the person of ordinary skill in the art that numerous different buffers may be used in the loading, washing, and elution steps. In a preferred embodiment of the invention a loading buffer comprising 5-100 mM Tris-HCl, pH 7.0-8.0, hereinafter referred to as "standard buffer", is used. Alternatively, a sodium phosphate buffer, such as 10 mM sodium phosphate, pH 7.5, may be used as standard buffer throughout the purification process since this will inhibit any residual phosphatases that could cleave off phosphate groups on the mannose-6-phosphate. The concentration of NaCl is increased to 0.05-0.15 M and 0.2-0.4 M during the wash and elution steps, respectively.

In an optional embodiment of the invention, the ion exchange resin is regenerated with a regeneration buffer after elution of the polypeptide, such that the column can be reused. Generally, the salt concentration and/or pH of the regeneration buffer is/are such that substantially all contaminants and the polypeptide of interest are eluted from the ion exchange resin. Generally, the regeneration buffer has a very high salt concentration for eluting contaminants and polypeptide from the ion exchange resin.

Step III in the purification process comprises an additional chromatography step, which preferably is Hydrophobic Interaction Chromatography (HIC). HIC utilizes the attraction of a given molecule for a polar or non-polar environment and in terms of proteins, this propensity is governed by the hydrophobicity or hydrophilicity of residues on the exposed, outer surface of a protein. Thus, proteins are fractionated based upon their varying degrees of attraction to a hydrophobic matrix, typically an inert support with alkyl linker arms of 2-18 carbons in chain length. The stationary phase consists of small non-polar groups (butyl, octyl or phenyl) attached to a hydrophilic polymer backbone (e.g. cross-linked sepharose, dextran or agarose). Thus, the HIC column is preferably a butyl sepharose column or a phenyl sepharose column, most preferably a butyl sepharose column.

Loading, washing and elution in HIC basically follow the same principle as described above for the ion-exchange chromatography, but often nearly opposite conditions to those used in ion exchange chromatography are applied. Thus, the HIC process involves the use of a high salt loading buffer, which unravels the protein to expose hydrophobic sites. The protein is retained by the hydrophobic ligands on the column, and is exposed to a gradient of buffers containing decreasing salt concentrations. As the salt concentration decreases, the protein returns to its native conformation and eventually elutes from the column. Alternatively proteins may be eluted with PEG.

The use of butyl sepharose and octyl sepharose as solid phases in the HIC is preferred in the present invention. Again, it is readily apparent that, when it comes to the exact conditions as well as the buffers and combinations of buffers used for the loading, washing and elution processes, a large number of different possibilities exist. In a preferred embodiment the column is equilibrated in the standard buffer mentioned above to which has been added 0.25-1 M $Na_2SO_4$. Washing is performed using 1-2 column washes of equilibration buffer followed by 1-5 column volumes of 1.0-3.0 M NaCl or 1.8 M Na-acetate in standard buffer pH 7.5. The rASA is eluted using 0.25-0.75 M NaCl or 1-5 column washes of 0.9 M Na-acetate in standard buffer pH 7.5.

In a further preferred embodiment of the invention, the purification of rASA by HIC succeeds the purification by ion-exchange chromatography as performed in the initial capture step. It is contemplated, however, that the two steps could be performed in the reverse order, but this will presumably lead to a lower yield.

In an additional embodiment of the invention, purification of the sample in step IV of the purification process is accomplished by tangential flow filtration.

In step IV of the purification process, the rASA is purified by separation from contaminants according to their size in an acidic environment by tangential flow filtration. The rASA forms an octamer at low pH with a theoretical molecular weight of 480 kDa and will therefore be retained by a relatively open membrane while most of the contaminants will pass this membrane (Sommerlade et al., (1994) Biochem. J., 297; 123-130; Schmidt et al., (1995) Cell, 82 271-278; Lukatela et al., (1998) Biochemistry, 37, 3654-3664). As the starting material for this process is a suspension of rASA as eluted from the chromatography column in the previous step of the process the pH in this suspension is adjusted to 4-5 by addition of 0.2-1 M Na-acetate pH 4.5. Diafiltration is then performed against 1-10 buffer volumes of Na-acetate pH 4.0-5.5 in a manner well known to somebody skilled in the art. The filtration can be performed with the application of several different filter types with nominal weight cut-off values ranging from 20-450 kDa, however it is preferred to use a filter with a cut-off value ranging from 100-300 kDa. For further processing of the rASA containing solution the pH is adjusted to a value within the range between 7 and 8 by addition of Tris-base to a final concentration of approximately 20-50 mM.

As an alternative to the acidic tangential flow filtration as described above, separation of rASA from the contaminants can be obtained with acidic gel filtration using essentially the same conditions and compositions of buffers. The filtration is performed at low pH through a gel filtration column, which has been equilibrated with a solution at low pH. In the current procedure a 0.2-0.9 M solution of Na-acetate at pH 4-5. As an option, the solution of rASA is concentrated by tangential flow filtration through a 20-50 kDa filter prior to the gel filtration. The extent of concentration may vary considerably so that the rASA may be concentrated from about 0.1 mg/ml to about 50 mg/ml preferably to about 5 mg/ml.

In a currently preferred procedure, the sample pool from step III is concentrated against a Biomax A-screen, 30 kDa. Diafiltration is performed against 3-5 column washes of 20 mM Na-acetate, pH 5.4-5.7. Most preferred is a process wherein tangential flow filtration occurs against a Biomax A-screen.

Several options exist for the polishing step (step V in the purification process). This step may involves purification using ion-exchange chromatography essentially as described above. As of convenience the sample is loaded in the buffer from the previous step of the purification process. In another embodiment, chromatography on a ceramic hydroxyapatite column can be used.

Hydroxyapatite (HAP) usually refers to the crystalline form of calcium phosphate. The mechanism of HAP involves non-specific interactions between negatively charged protein carboxyl groups and positively charged calcium ions on the resin, and positively charged protein amino groups and negatively charged phosphate ions on the resin. Basic or acidic proteins can be adsorbed selectively onto the column by adjusting the buffer's pH; elution can be achieved by varying the buffer's salt concentration. Again, it is evident that numerous buffer compositions as well as combinations of buffers can be employed. Preferably, however, the column is equilibrated with 1-10 column washes of a buffer comprising 1-100 mM Tris-HCl pH 7.0-8.0. As of convenience the sample is loaded in the buffer from the previous step of the purification process. The column is washed with 1-10 column volumes of the buffer used for equilibration and the sample is eluted in a mixture of this buffer and a buffer comprising 100-800 mM Sodium phosphate. Optionally the column is reconstituted by washing with 1-10 column volumes of 100-800 mM Sodium phosphate.

In the chromatography steps the appropriate volume of resin used when packed into an chromatography column is reflected by the dimensions of the column, i.e. the diameter of the column and the height of the resin, and varies depending on e.g. the amount of protein in the applied solution and the binding capacity of the resin used. However, it is within the scope of the present invention to increase the scale of the production process as well as the purification process in order to obtain production and purification of rASA on an industrial scale. Accordingly parameters such as column size, diameter, and flow rate can be increased in order to comply with the speed and efficiency of such large-scale production. Whereas columns with a diameter ranging from 50-100 mm, volumes in the size of 100-300 ml, and flow rates between 40-400 cm/hour or 5 to 100 ml, are suitable for small-scale (non-industrial) purification.

In a presently preferred version, the procedure of step V is based on the characteristics of rASA as follows: Theoretically and practically, rASA has an isoelectrical point which is in the vicinity of pH 6.0. This means that the protein should bind to an anion exchanger at a pH larger than 6.5 and to a kation exchanger at a pH less than 5.5. The present inventors have confirmed such binding to a kation exchanger experimentally, where it is found that, in principle, no rASA binds at a pH of 5.6. Approximately 50% of any rASA binds at pH 5.2 and 100% binds at pH 4.8. For the anion exchanger, however, rASA binds at any pH-value tested within the range from 7.2 down to 4.8. In principle, it thus appears that rASA binds to positively charged anion exchangers at pH 4.8, where the enzyme itself should also be positively charged. Under the same conditions the enzyme binds equally well to a cation exchanger. It is assumed that these unexpected binding characteristics result from the enzyme being extremely polarized having a strong "positively charged" side and a strong "negatively charged" side. Alternatively, the binding characteristics may be explained by the enzyme changing from a dimer to an octamer at pH-values under 5.8.

The currently preferred procedure of step 5 takes advantage of these unexpected characteristics. The polishing step is thus initiated at pH 6.0 where the enzyme will not bind to a first affinity chromatography resin or a first cation exchanger (passive step). This step, however, eliminates many of the contaminating Host Cell Proteins. For a preparation to be used in a pharmaceutical preparation the amount of such proteins must be at a very minimum.

Following the passage through the affinity or cation resin the rASA will bind to a subsequent anion exchange resin, which may be coupled to the cation resin in series. If the two resins are coupled, the cation exchange resin is subsequently uncoupled and the amino exchanger is washed at a pH around 4.8, leaving rASA bound to the resin. The fact that rASA remains bound to the resin at pH 4.8 is highly unexpected and it is contemplated that this ability will only be shared by very few other protein as, effectively they should have an isoelectrical point below 4.2.

Accordingly, in the currently most preferred embodiment of the invention the two or more successive steps in step V of the purification process comprise a passive step, wherein the rASA passes through a cation chromatography resin or membrane, and an active step, wherein the rASA is detained within and subsequently eluted from an anion exchange membrane or resin. The anion exchange membrane or resin may be a high resolving anion exchanger.

Additionally, it may be further preferred that the cation chromatography chromatography membrane or resin and said anion exchange membrane or resin are coupled or connected in a series. In the present context, the term "coupled or connected in a series", when used in connection with the affinity or cation chromatography and anion ion exchange chromatography, means that the proteins passing through the affinity or cation chromatography resin are loaded directly onto the anion ion exchange resin with no change of buffer or other conditions.)

In a currently most preferred embodiment of the invention the cation chromatography chromatography membrane or resin is a Mustang™ S membrane, an S-sepharose resin or a Blue Sepharose resin and said anion exchange membrane or resin is a Mustang™ Q membrane or Source™ Q resin.

In a specific embodiment of the invention, the columns are equilibrated with more than 10 column volumes of 20-100 mM NA-acetate pH 4.5-8.5, preferably 20-100 mM Sodium Acetate pH 5.5-7.7. Sample pool from step 4 is loaded on the columns and after passage of the rASA through the cation exchange column the two columns are uncoupled and the anion exchanger is washed with 2-4 column volumes of 50-75 mM Na-acetate pH 4.8. The anion exchanger is equilibrated with more than 10 column volumes of 20 mM Tris-HCL pH 7.5 (standard buffer). The column is washed with 0.1 mM NaCl in standard buffer and the rASA is eluted with a linear gradient of 0.1-0.3 M NaCl in standard buffer.

In a currently preferred embodiment the anion and/or cation resins or membranes are washed with 2-4 column washes of 20-70 mM Sodium Acetate at pH 4.8. 31. It is equally preferred that the anion exchange membrane or resin is equilibrated with at least 11 column washes of 10 mM sodium phosphate pH 7.5 and, subsequently, washed with 60 mM NaCL in 10 mM sodium phosphate pH 7.5. Finally, it is currently preferred that the arylsulfatase A is eluted from the anion exchange resin with a linear gradient of 60-500 mM NaCl in 10 mM sodium phosphate pH 7.5

In the purification process is further incorporated one or more steps of virus inactivation or virus filtration. It is understood that these methods are intended to give rise to a preparation of an enzyme, which is substantially free of infectious vira and which can be denoted a "virus-safe product". In addition, it is contemplated that the various methods can be used independently or in combination. Preferably, virus filtration is performed after purification of the enzyme by several steps of chromatography. In a preferred embodiment, the virus filtration step is performed by passage of the rASA containing solution which is a result of step 5 of the purification process through a sterile filter and subsequently passage of the sterile filtered solution through a nanofilter. By "sterile filter" is meant a filter, which will substantially remove all micro-organisms capable of propagating and/or causing infection. Whereas it is preferred that the filter has a pore size of 0.1 micron, the pore size could range between 0.05 and 0.3 micron.

In addition to or as an alternative to virus filtration, virus-inactivation can be accomplished by the addition of one or more "virus-inactivating agents" to a solution comprising the enzyme. Preferably, the virus-inactivating step will be performed prior to the purification process in order to assure that the agent is not present in the final product in any amounts or concentrations that will compromise the safety of the product when used as a pharmaceutical or when the product is used for the preparation of a pharmaceutical. The term "virus-inactivating agent" is intended to denote such an agent or a method, which can be used in order to inactivate lipid-enveloped viruses as well as non-lipid enveloped viruses. The term "virus-inactivating agent" is to be understood as encompassing both a combination of such agents and/or methods, whenever that is appropriate, as well as only one type of such agent or method.

It may be feasible to replace or combine virus filtration of the sample as performed in step VI of the purification process with contacting the sample with a detergent, preferably prior to step V or preferably prior to step II of the purification process.

Preferred virus-inactivating agents are detergents and/or solvents, most preferably detergent-solvent mixtures. It is to be understood that the virus inactivating agent is optionally a mixture of one or more detergents with one or more solvents. A wide variety of detergents and solvents can be used for virus inactivation. The detergent may be selected from the group consisting of non-ionic and ionic detergents and is selected to be substantially non-denaturing. Preferably, a non-ionic detergent is used as it facilitates the subsequent elimination of the detergent from the rASA preparation in the subsequent purification steps. Suitable detergents are described, e.g. by Shanbrom et al., in U.S. Pat. No. 4,314,997, and U.S. Pat. No. 4,315,919. Preferred detergents are those sold under the trademarks Triton X-100 and Tween 20 or Tween 80. Preferred solvents for use in virus-inactivating agents are di- or trialkylphosphates as described e.g. by Neurath and Horowitz in U.S. Pat. No. 4,764,369. A preferred solvent is tri(n-butyl)phosphate (TNBP). An especially preferred virus-inactivating agent for the practice of the present invention is Tween 20, but, alternatively, other agents or combinations of agents can be used. The preferred agent added in such a volume that the concentration of Tween-20 in the rASA-containing solution is within the range of 0.5-4.0% by weight, preferably at a concentration of about 1% by weight.

The virus-inactivation step is conducted under conditions inactivating enveloped viruses resulting in a substantially virus-safe rASA-containing solution. In general, such conditions include a temperature of 4-37° C., such as 19-28° C., 23-27° C., preferably about 25° C., and an incubation time found to be effective by validation studies. Generally, an incubation time of 1-24 hours is sufficient, preferably 10-18 hours, such as about 14 hours, to ensure sufficient virus inactivation. However, the appropriate conditions (temperature and incubation times) depend on the virus-inactivating agent employed, pH, and the protein concentration and lipid content of the solution.

It is contemplated that other methods for removal of or inactivating virus can also be employed to produce a virus-safe product, such as the addition of methylene blue with subsequent inactivation by radiation with ultraviolet light.

In a preferred embodiment, the process according to the invention results in a product or formulation comprising a relative amount of bioactive recombinant arylsulfatase A, in particular recombinant human arylsulfatase A which is at least 90%, such as at least 95%, at least 97%, at least 98%, at least 99%, at least 99.5%, or at least 99.9% of the total amount of proteins in the product or formulation as determined by reverse phase HPLC.

A therapeutic formulation comprising the polypeptide, optionally conjugated with a heterologous molecule, may be prepared by mixing the polypeptide having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. "Pharmaceutically acceptable" carriers, excipients, or stabilizers are nontoxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride: phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN, PLURONICST or polyethylene glycol (PEG).

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semi-permeable matrices of solid hydrophobic polymers containing the polypeptide variant, which matrices are in the form of shaped articles, e.g., films, or microcapsule. Examples of sustained-release matrices include polyesters, hydrogels (for example, poly (2-hydroxyethyl-methacrylate), or poly (vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)3-hydroxybutyric acid.

The polypeptide purified as disclosed herein or the composition comprising the polypeptide and a pharmaceutically acceptable carrier is then used for various diagnostic, therapeutic or other uses known for such polypeptides and compositions. For example, the polypeptide may be used to treat a disorder in a mammal by administering a therapeutically effective amount of the polypeptide to the mammal.

In a specific embodiment of the invention, the rASA is formulated in an isotonic solution such as 0.9% NaCl and 10-50 mM Sodium phosphate pH 6.5-8.0 or sodium phosphate, glycine, mannitol or the corresponding potassium salts. In another embodiment the rASA is formulated in a physiological buffer, such as:
a) formulation buffer I containing (in mM): $Na_2HPO_4$ (3.50-3.90), $NaH_2PO_4$ (0-0.5), Glycine (25-30), Mannitol (230-270), and water for injection; or
b) formulation buffer II containing (in mM): Tris-HCl (10), Glycine (25-30), Mannitol (230-270), and water for injection.

In a further embodiment, the rASA is formulated as lipid vesicles comprising galactoside and/or phosphatidyl choline and/or phosphatidyl ethanolamine.

A further embodiment of the invention is a process wherein the rASA is formulated as a sustained release formulation involving bio-degradable microspheres, such as microspheres comprising polylactic acid, polyglycolic acid or mixtures of these.

It may further be desired to formulate the rASA with a hypertonic solution in order to cause osmotic opening of the blood-brain barrier and also to formulate the rASA is formulated in a solution comprising an enhancer for nasal administration.

A specific embodiment is contemplated, wherein the rASA is formulated so as to enhance its half-life in the bloodstream and/or reduce clearing via the kidneys and/or prevent extended uptake via the liver.

Finally, the process according to the invention may result in production, purification and formulation of a protein, which is enzymatically equivalent to rASA. This enzyme may in terms of its structure be different from the rASA according to SEQ ID NO: 3. It may be an advantage that the sequence of amino acid residues surrounding the Cys-51 is identical or has a high degree of sequence identity to the corresponding sequence in SEQ ID NO: 3. Thus, it may be preferred that a linear sequence of 20 amino acids, such as 19, 18, 17, 16, 15, 14, 13, 12, 11, 10, 9, 8, 7, 6, 5 or 4 amino acid residues surrounding the Cys-51 in the arylsulfatase A is identical or at least 90% identical, such as 95%, 96%, 97%, 98%, or 99% identical to the corresponding sequence in SEQ ID NO: 3. As the active form of rASA within the lysosymes is an octamer a further object of the invention is to provide a rASA which is an octamer or assembles into an octamer under physiological conditions.

Other aspects of the present inventions include analytical methods for testing the efficiency of each purification step as well as the quality of the resulting preparations of rASA with respect to, for instance, enzyme activity, concentration of total protein and rASA, purity, and endotoxin levels.

Enzyme activity, which is to be understood as the catalytic activity of the rASA, may be measured in an enzyme assay based on the rASA mediated hydrolysis of either a detectable substrate or a substrate, which leads to a detectable end product. In a preferred aspect the assay is based on hydrolysis of the synthetic, chromogenic substrate, para-Nitrocatechol sulphate (PNCS) which has an end product, para-Nitrocatechol (pNC) that absorbs light at 515 nm.

Total protein concentration in in-process samples and final products may be determined by a commercially available assay that utilises principles of the reduction of $Cu^{2+}$ to $Cu^+$ by proteins in an alkaline medium (the Biuret reaction). This method is well known to a person skilled in the art.

Concentration of rASA in samples collected after various steps of the purification process may be assessed in rASA enzyme linked immunosorbent assay (ELISA). Quantitative determination of a protein by ELISA is a conventional technique known to the person of ordinary skill in the art. However, it is within the scope of the present invention to provide a specific ELISA for the detection of rASA based on capturing the enzyme with specific polyclonal immunoglobulins and subsequently detecting the captured enzyme with specific monoclonal antibodies.

Purity and identity of the various preparations of rASA may be determined by methods well known to the person of ordinary skill in the art, such as rpHPLC, SDS-PAGE, and Western blot rASA. In addition, the amount of whole cell proteins (HCP) in preparations of rASA may be determined by the use of ELISA as well as Western blotting techniques using commercially available antibodies. Preferably, all the above mentioned processes are adapted to be performed in microtiter plates for convenience.

As compared to batch fermentation the continuos fermentation process of the present invention allows tight control of the process parameters so as to provide preparations and formulations of the enzyme which are of a uniform high quality. The characteristics of the enzyme product of the present invention as well as the formulation comprising the enzyme product and its applicability in the prevention or treatment of MLD depends critically on the production and purification process described above. Another main aspect of the present invention therefore pertains to a formulation of arylsulfatase A and an arylsulfatase A product, which are obtainable or obtained by a process as described above.

While the use of various adjuncts, including vehicles for cellular delivery and membrane permeating agents, have been suggested in order to enhance the therapeutic efficiency of arylsulfatase A in enzyme replacement therapy in vivo experiments have surprisingly shown that the enzyme preparation or formulation according to the present invention is highly efficient when used without any such adjuncts. Accordingly, it is presently preferred that the formulation of arylsulfatase A does not comprise any of the following:
  a) a vehicle, such as a peptide or polypeptide, for delivery of the enzyme (arylsulfatase A) into the central nervous system, and
  b) a component capable of causing opening or disruption of the blood brain barrier, and
  c) an intact cell.

A number of vehicles are mentioned in previous sections of the present description, including peptides such as the insulin fragment, peptides and proteins derived from virus or bacteria, antibodies or antibody fragments such as transferrin receptor antibodies and toxins. Also, the use of intact cells including a transduced cell, for instance a transduced autologous cell, such as a transduced fibroblast or a peripheral blood lymphocyte has been suggested in the art. In particular, implantation of polymer encapsulated cell lines secreting arylsulfatase A into the cerebrospinal fluid has been suggested. Furthermore, a number if agents or chemicals, such as for instance thiosulphate, are known to cause temporary disruption of the blood brain barrier. An arylsulfatase A or a formulation of arylsulfatase A according to the present invention may of course be combined with such vehicles, agents, chemicals or cell systems. As mentioned above, formulation of arylsulfatase A in a hypertonic solution has also been suggested in order to enhance the accessibility of the central nervous system. In a preferred embodiment of the invention, however, the use of any or all of such known vehicles, agents, chemicals, formulations or cell systems in connection with the enzyme preparation of the present invention is hereby disclaimed.

In addition, the possibility of administrating enzyme preparations directly across the blood brain barrier, such as by spinal or intrathecal injection, has been discussed in the prior art. It is preferred, however, that the formulation of arylsulfatase A according to the present invention is for systemic delivery, such as for intravenous administration.

The arylsulfatase A product and the formulation comprising arylsulfatase A according to the present invention have as one of their characteristics a very low content of host cell proteins. In a product or formulation intended as a pharmaceutical composition or a product intended to be used in the preparation of a pharmaceutical composition the content of such proteins is critical since they are expected to have immunogenic effects. In a preferred embodiment of the invention the final product or formulation contain less than 1.5% whole cell proteins, such as less than 1%, e.g. less than 0.75%, or less than 0.5%, or less than 0.25% whole cell proteins. The product or formulation may further contain impurities in the form of enzymatically inactive variants of the main component. In a preferred embodiment the product or formulation according to the invention contains at least 90% enzymatically active rASA, such as 92% or 94%. In an even more preferred embodiment the relative amount of enzymatically active rASA is at least 95%, such as 96% or 97% or even 98% or 99% as determined by reverse phase HPLC.

In addition to the process according to the invention it is an object of the invention to provide a formulation or a pharmaceutical composition comprising rASA, which is efficiently endocytosed via the mannose-6-phosphate receptor pathway in vivo. When applied to endocytosis of rASA, the term "efficiently" refers to endocytosis leading to at least a 100-fold increase in the concentration of rASA within cells in the kidney, the plexus brachialis and the nervus ischiaticus in MLD mice eight days after intravenous injection of a single dose of rASA (40 mg/kg).

In accordance with the described efficiency of the of the purification process it is preferred that this formulation or composition comprises at least 98% bioactive rASA as determined by reverse phase HPLC. A further characteristic of the enzyme or formulation prepared according to the process of the invention is its high level of specific activity. It is thus preferred that the formulation or pharmaceutical composition according to the invention comprises a rASA with a specific activity of at least 10 U/mg, at least 20 U/mg, at least 25 U/mg, at least 30 U/mg, at least 40 U/mg, at least 50 U/mg, at least 60 U/mg, at least 70 U/mg, at least 75 U/mg, at least 80 U/mg, at least 85 U/mg, at least 90 U/mg, at least 100 U/mg, at least 150 U/mg, at least 200 U/mg at least 250 U/mg or at least 300 U/mg protein Another main aspect of the invention is an arylsulfatase A or a formulation comprising an effective amount of arylsulfatase A, for use as a medicament. The rASA may have any of the characteristics described above and it is thus preferred that the arylsulfatase A or the formulation is obtainable or actually obtained by a process according to the invention. Specifically, it is an object of the invention to provide a rASA for use as a medicament for reducing the sphingolipid 3-O-sulfogalactosylceramide (galactosyl sulphatide) levels within cells in the peripheral nervous system and/or within the central nervous system in a subject suffering from and/or being diagnosed with metachromatic leukodystrophy.

In accordance with the disclosures in the present application the administration of this rASA will lead to decreased impairment of motor-learning skills and or to increased nerve motor conduction velocity and/or nerve conduction amplitude.

According to a recent publication, intrathecal injection, that is injection directly into the cerebrospinal fluid) of recombinant human alpha-L-iduronidase (rhIDU) can reduce carbohydrate storage in brain tissue in a canine model of mucopolysaccharidosis (MPL) (Kakkis, 2003). On the basis of these observations, the present invention provides methods of treatment which comprise:
(a) administration of a pharmaceutical composition according to the invention intravenously in order to obtain a reduction in galactosyl sulphatide levels in target cells within the peripheral nervous system, optionally as an adjunct to treatment by bone marrow transplantation; and/or
(b) administration of a pharmaceutical composition according to the invention intravenously in order to obtain a reduction in galactosyl sulphatide levels in target cells both within the peripheral and central nervous system; and/or
(c) administration of a pharmaceutical composition according to the invention intravenously in order to obtain a reduction in galactosyl sulphatide levels in target cells within the peripheral nervous system, optionally in combination with intrathecal injection of a pharmaceutical composition according to the invention in order to obtain a reduction in galactosyl sulphatide levels in target cells within the central nervous system.

Accordingly, the method according to the invention preferably comprises administering said pharmaceutical composition intravenously and by spinal injection and thereby obtaining a reduction in the galactosyl sulphatide levels in target cells within the peripheral nervous system and in target cells within the central nervous system in said subject.

According to a further preferred embodiment of the invention the method comprises administering said pharmaceutical composition intravenously to said subject and thereby obtaining a reduction in the galactosyl sulphatide levels in target cells within the peripheral nervous system and in target cells within the central nervous system in said subject.

A further preferred embodiment of the invention is a method wherein rASA is efficiently endocytosed in vivo into target cells within a tissue selected from the group comprising liver, kidney, spleen, heart.

As the skilled addressee will be aware said target cells within the central nervous system are preferably oligodendroglia and said target cells within the peripheral nervous system are preferably Schwann cells.

It is contemplated that the exact nature of the treatment plans based on the method according to the present invention will depend on factors such as age, sex and disease stage of the subject to be treated, and that the optimal dose regimen and frequency of administration may, with advantage, be determined on an empirical basis. However In one preferred embodiment of the invention said pharmaceutical composition is administered in one or more doses, each dose comprising an amount of rASA which is within the range of 0.1 to 100 mg/kg body weight, such as within the range of 0.25 to 50, 1 to 25, 1 to 10 or 1 to 5 mg/kg body weight.

Also it may be preferred that the pharmaceutical composition is administered on a daily, weekly, bi-weekly or monthly basis.

In accordance with the above description, intravenous and or spinal injection of said pharmaceutical composition may be performed as a supplement to bone marrow transplantation.

While enzyme replacement therapy has been suggested as an approach to the treatment of diseases characterised by increase lysosomal accumulation of galactosyl sulphatide it has been accepted as a fact the therapeutic effects of conventional enzyme replacement therapy based on systemic administration of the enzyme would be limited to the peripheral nervous system. An interesting aspect of the present invention relates to the surprising discovery that administration of a formulation containing arylsulfatase A, when repeated on a regular basis, causes a reduction in the levels of stored lipids, not only in the peripheral nervous system, but also in the central nervous system. This aspect of the invention provides the use of a formulation comprising an effective amount of arylsulfatase A for the manufacture of a medicament for reducing the levels of galactosyl sulphatide in cells within the central nervous system in a subject suffering from and/or being diagnosed with metachromatic leukodystrophy. In a further preferred embodiment of the present invention, therefore, the method according to the invention leads to a reduction in the galactosyl sulphatide levels in target cells within the central nervous system created wholly or in part by a washout effect caused by the clearance of sulfatides in tissues and in blood. Sulfatides are cleared from the brain partly due to the concentration gradient resulting from the clearance of sulfatides in the tissue and in the blood.

Consistent with the fact that only marginal increases in enzyme levels are seen in cells within the brain the therapeutic affects in the CNS results mainly from the maintenance of effective levels of enzyme in the circulation or in the visceral organs as caused by systemic administration of an effective amount of the enzyme. Thus, the effective amount of arylsulfatase A is such that:
a) effective levels of the enzyme are sustained in circulation for not less than 8 days, and/or
b) effective levels of the enzyme are sustained in visceral organs, sciatic nerve and brachial plexus for not less than 8 days, and/or
c) effective levels of the enzyme are sustained in the liver for not less than 8 days, subsequent to systemic and preferably intravenous administration of said formulation.

As the effects seen after administration of arylsulfatase A appear transient, it is contemplated that effective amount of arylsulfatase A must be such that:
a) effective levels of the enzyme are sustained in circulation, and/or
b) effective levels of the enzyme are sustained in visceral organs, sciatic nerve and brachial plexus, and/or
c) effective levels of the enzyme are sustained in the liver and/or kidney by repeated intravenous administration of the formulation on a weekly, bi-weekly or monthly basis. In the present context the term "effective levels" is to be understood as levels of arylsulfatase A, which are effective in causing at least a 100% reduction of the stored sphingolipid 3-O-sulfogalgactosylceramide (galactosyl sulphatide) in cells within visceral organs, including the kidney, as determined by TLC 8 days after intravenous administration of arylsulfatase A in an amount of 40 mg/kg body weight. It may be preferred that the reduction in galactosyl sulphatide is at least 15%, at least 20%, at least 25%, at least 30% or at least 40% relative to the levels present prior to administration of the enzyme. Also, it may be preferred that the arylsulfatase A is administered in an amount of between 5 and 100 mg enzyme per kg of body weight, such as 10 mg/kg body weight, 20 mg/kg body weight, 30 mg/kg body weight, 50 mg/kg body weight, 60 mg/kg body weight, 70 mg/kg body weight 80 mg/kg body weight or 90 mg/kg body weight. As the effects in the CNS are likely to depend critically on the quality of the enzyme, it is preferred that the arylsulfatase A formulation is a formulation as described above.

It is further of importance that the enzyme has a high specific activity, and it is preferred that the arylsulfatase A has a specific activity of at least 20 U/mg, such as at least 30 U/mg, at least 40 U/mg, at least 50 U/mg, at least 60 U/mg, at least 70 U/mg, at least 80 U/mg or at least 90 U/mg.

The use of adjuncts, such as compounds or formulations with a know ability to facilitate delivery of macromolecules to the central nervous system does not appear necessary in order to obtain the observed effect in the central nervous system. In a preferred embodiment, therefore, the medicament does not comprise any of the following components:
a) a vehicle, such as a peptide or polypeptide, for delivery of the enzyme (arylsulfatase A) into the central nervous system, and
b) a component capable of causing opening or disruption of the blood brain barrier, and
c) an intact cell, including a transduced cell, such as a transduced autologous cell, such as transduced fibroblasts or peripheral blood lymphocytes.

It is also apparent that supplementary treatment with any of the above mentioned agents or components may be unnecessary. It is therefore preferred that the medicament is for administration to a subject which does not receive any additional medical treatment for reduction of the sphingolipid 3-O-sulfogalgactosylceramide levels, including:
- a) administration of a formulation comprising a vehicle, such as a peptide or polypeptide or antibody, for delivery of the enzyme (arylsulfatase A) into the central nervous system, and
- b) administration of a formulation capable of causing opening or disruption of the blood brain barrier, and
- c) administration of an intact cell, including a transduced cell, such as a transduced autologous cell, such as transduced fibroblasts or peripheral blood lymphocytes.

Still another aspect of the invention is a method of treating a subject in need thereof, said method comprising administering to said subject a pharmaceutical composition comprising a rASA, which may have any of the characteristics described above, and thereby obtaining a reduction in the galactosyl sulphatide levels in target cells within said subject.

This aspect of the invention thus pertains to a method of treating/alleviating a symptom of a disorder associated with increased lysosomal storage of sphingolipid 3-O-sulfogalgactosylceramide (metachromatic leukodystrophy), said method comprising administering to a subject a formulation of arylsulfatase A obtained or obtainable by a process according to the invention and thereby obtaining a reduction in the galactosyl sulphatide levels in cells within said subject. It is to be understood that the cells, which are targeted by this method of treatment may be or may include cells within the peripheral nervous system and/or cells within the central nervous system. The disorder may be Metachromatic Leukodystrophy (MLD) or Multiple sulfatase deficiency (MSD).

As mentioned it is preferred that the administration of the medicament, that is the formulation of arylsulfatase A does not comprise mechanical, chemical or biological invasion of the central nervous system. These terms comprise direct administration of the medicament across the blood brain barrier as well as the use of adjuncts an/or formulations with a known ability of facilitating delivery of macromolecules across the blood brain barrier.

Accordingly the therapeutic method of the invention preferably comprises administering the formulation of arylsulfatase A by a route other than intracerebroventricular, spinal, intrathecal or intracranial administration, such as a route selected from the group consisting of intravenous, intraarterial, oral, subcutaneous, intraperitoneal, intramuscular, intraparenchymal, mucosal, nasal, and rectal administration.

Most importantly, it must be acknowledged that the therapeutic method according to the invention provides an efficient approach to the treatment of metachromatic leukodystrophy. Therefore, in a preferred embodiment, the subject receiving therapeutic treatment according to the invention, including the administration of a formulation of arylsulfatase A, is a subject which does not receive any of the following treatments previous to, concomitant with or subsequent to the administration of said formulation of arylsulfatase A:
- a) administration of a formulation of aryl sulphatase A by route selected from a group consisting of intracerebroventricular, spinal, intrathecal or intracranial administration,
- a) administration of a vehicle for delivery of the enzyme to the central nervous system,
- b) transplantation of bone marrow or bone marrow stem cells,
- c) administration of cells expressing endogenous and/or exogenous arylsulfatase A,
- d) administration of a medicament capable of causing opening or disruption of the blood brain barrier, for instance sodium thiosulphate, or a hypertonic solution capable of increasing the permeability of the blood brain barrier,
- f) systemic or intrathecal administration of intact cells, including a transduced cell, such as a transduced autologous cell, such as transduced fibroblasts or peripheral blood lymphocytes,
- g) gene therapy.

The topographic distribution of lysosomal sulfatide storage in the central nervous system of arylsulfatase A deficient mice is described in detail in Wittke, D. et al. 2004, Acta Neuropathol 108, 261-271. In the present context a reduction in the sulfatide storage within the central nervous system is seen in particular in phagocytes, including activated microglial cells, neurons and oligodendroglia. The reduction in sulfatide levels within the central nervous system is primarily seen in cells located within the white or grey matter within any one of the following regions: Spinal cord, brain stem, cerebellum, forebrain nuclei and cerebral cortex.

In addition to the reduction in sulfatide levels in cells within the central nervous system as described above a corresponding reduction is seen within the peripheral nervous system, in particular in the Schwann cells.

In a further embodiment of the invention, the pharmaceutical composition further comprises a hypertonic solution or is administered together with a hypertonic solution in order to cause osmotic opening of the blood-brain barrier.

The ability of rASA to enter into a target cell over the cell membrane while maintaining its catalytic properties can be determined in vitro using cultures of a cells containing a suitable substrate for the enzyme as described by Kudoh and Wenger. J. Clin. Invest. 1982. 70(1): 89-97. Example 2 of the present text provides an example of such a model system and shows test results for a preparation of rASA obtained by the process described.

Accordingly, one aspect of the present invention includes a model system comprising a culture of mammalian cells wherein the degradation of sulfatides by exogenous ASA can be determined. In a preferred aspect of this embodiment these cells are fibroblasts derived from a MLD patient and accordingly they lack endogenous functional ASA. It is readily apparent, however, that other cells which are characterised by deficient ASA activity and the ability to accumulate a detectable substrate of ASA can form the basis of such an assay, hereunder cells that are genetically engineered so as to reduce or abolish the expression and/or function of ASA. In another preferred aspect of this embodiment the sulfatides used as substrate in this system are labelled by the addition of a radioactive or non-radioactive compound for subsequent detection. In a most preferred aspect the substrate of rASA is palmitoyl sulfatide, and in an equally preferred aspect the substrate is labelled with $^{14}C$.

An additional embodiment of the invention is a preparation of rASA, which is capable of reducing the cellular content of one or more of its substrates when analysed in the system described above. Preferably, the enzyme will be added to the culture medium at a concentration ranging from 0 to 100 mU/ml and lead to a reduction in the intracellular substrate levels preferably corresponding to 20%, more preferably 30%, even more preferably 40%, still more preferably 50%, yet more preferably 60%, most preferably more than 70%.

A final aspect of the invention provides a continuous cell culture system as described for the process according to the invention.

With respect to the above description of the various aspects of the present invention and of the specific embodiments of these aspects it should be understood that any feature and characteristic described or mentioned above in connection with one aspect and/or one embodiment of an aspect of the invention also apply by analogy to any or all other aspects and/or embodiments of the invention described.

When an object according to the present invention or one of its features or characteristics is referred to in singular this also refers to the object or its features or characteristics in plural. As an example, when referring to "a cell" it is to be understood as referring to one or more cells.

Throughout the present specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The following text provides an example of production of rASA by continuous cell propagation in the culture system and purification of the product according to step 1 through 5 of the purification procedure as outlined above (examples 1 and 2). The biological activity of the purified rASA is evaluated in an in vitro system as described above. Furthermore, the effects of administrating rASA according to the present invention in vivo are evaluated in a series of experiments performed on ASA(-/-) (knockout) mice, also denoted MLD-mice. Results from these in vitro and in vivo experiments are provided in examples 3 to 6.

These examples serve to provide a further characterisation of the invention, however they are not intended to be limiting to the scope of the invention.

BRIEF DESCRIPTION OF THE ACCOMPANYING DRAWINGS

FIG. 1: (A) Schematic representation of the system for continuous cell propagation. (B) Outline of the purification process.

Figure 2:
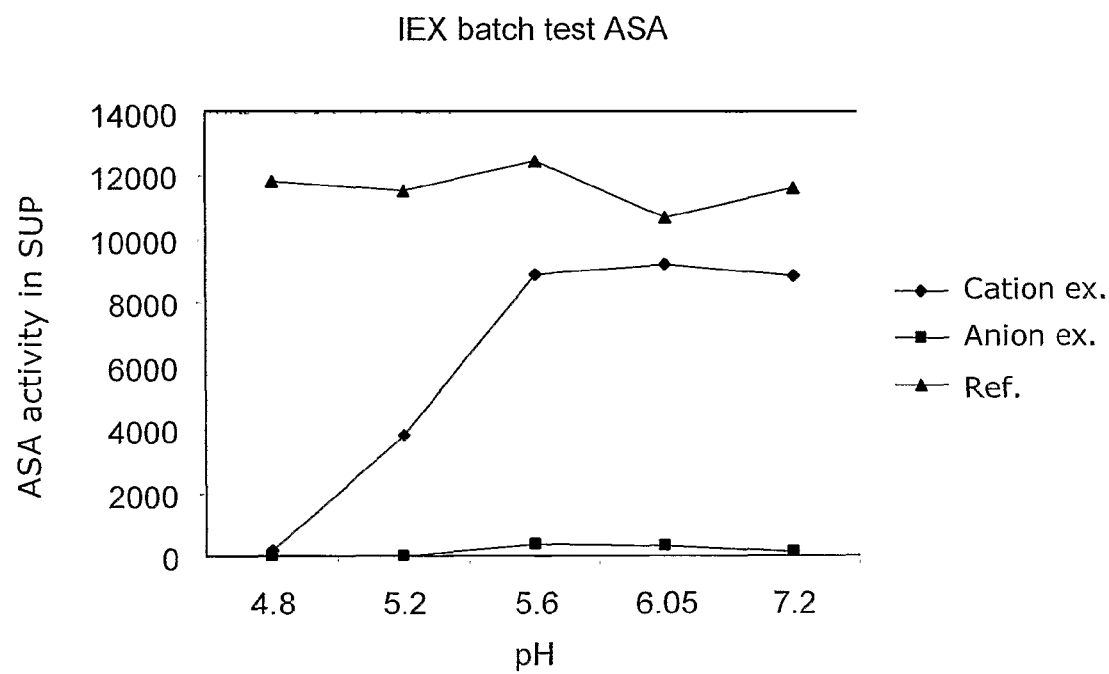

FIG. 2: Ion exchange chromatography batch test of rhASA.

Figure 3:
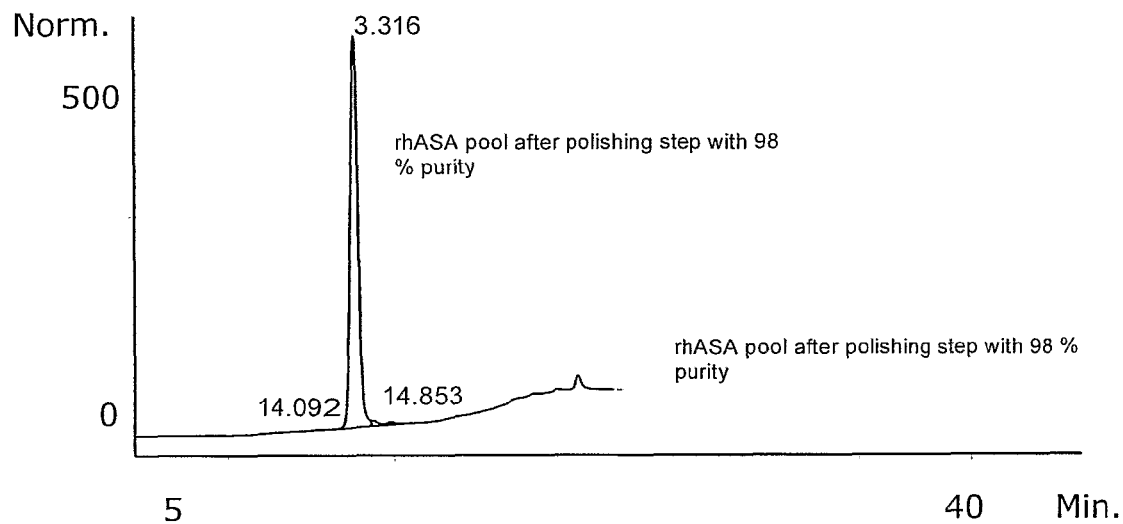
Figure 3:
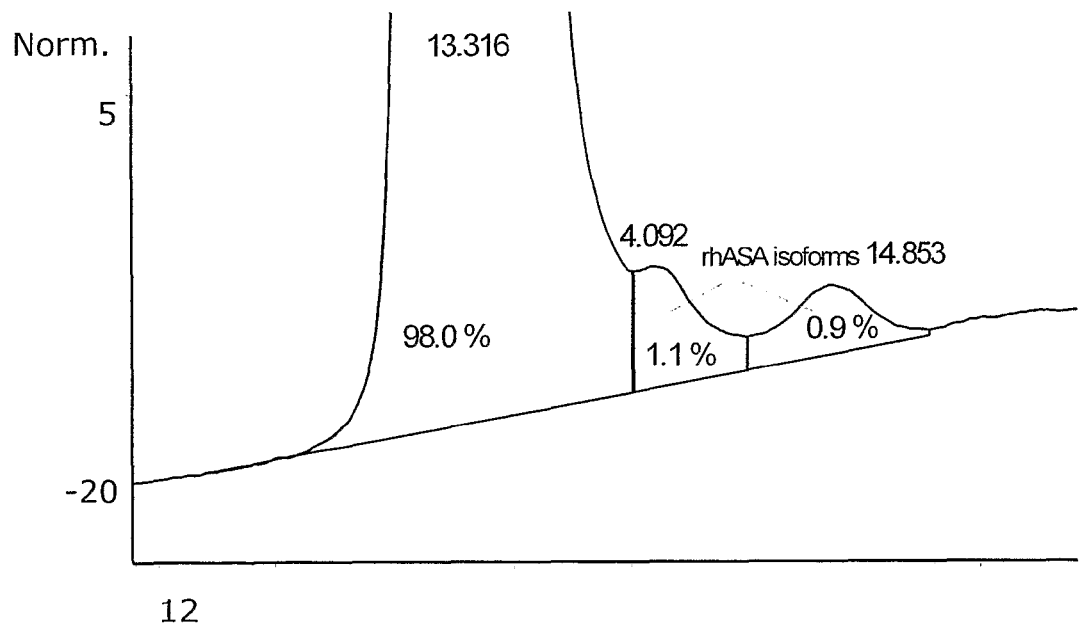

FIG. 3: (A) HPLC-chromatogram of rhASA after completion of step (V) of the purification procedure according to the present invention. (B) Enlargement of the HPLC chromatogram of (A).

Figure 4:
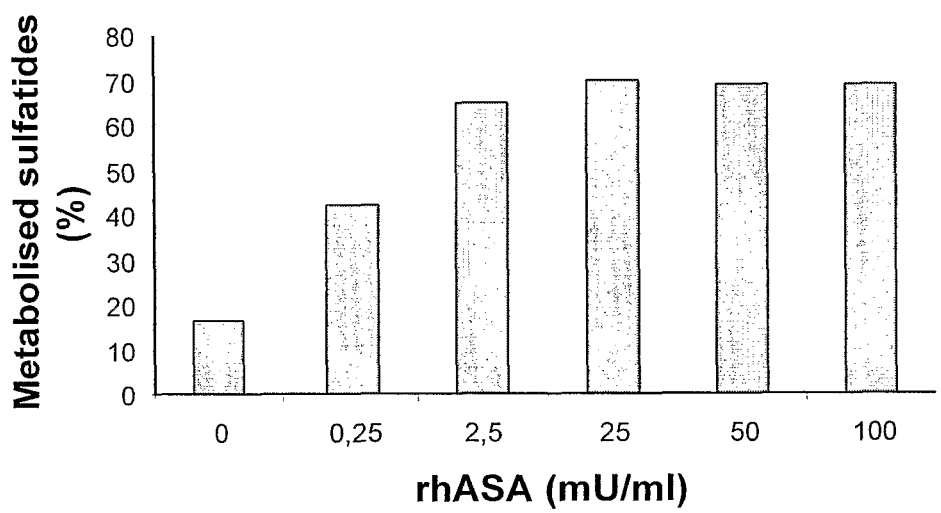

FIG. 4: Sulfatide clearance in MLD-fibroblasts loaded with radiolabelled sulphatide after incubation with rhASA for 24 hours.

Figure 5:
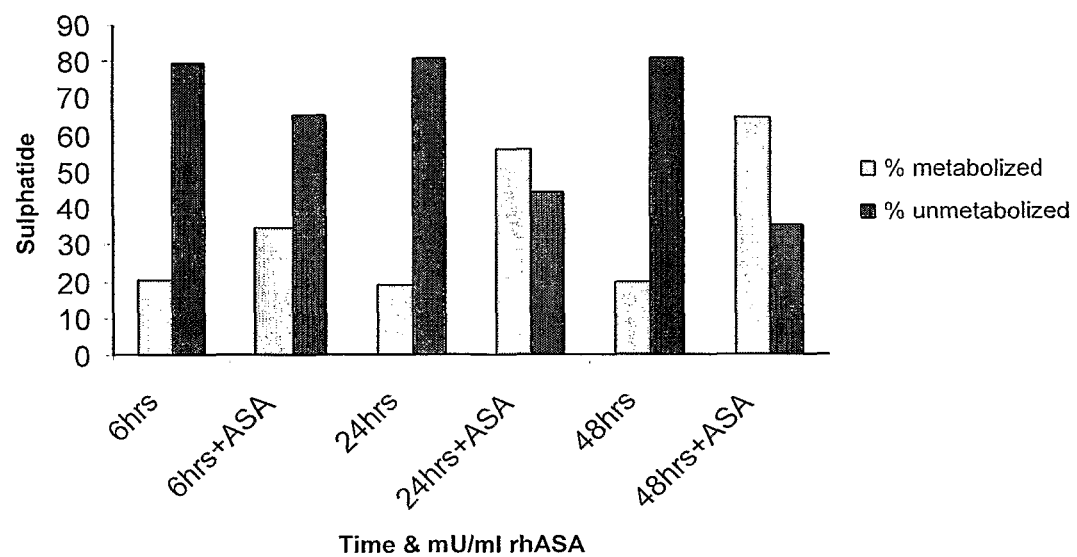

FIG. 5: Sulfatide clearance in MLD-fibroblasts loaded with radiolabelled sulphatide after incubation with rhASA for 6, 24 and 48 hours.

Figure 6:
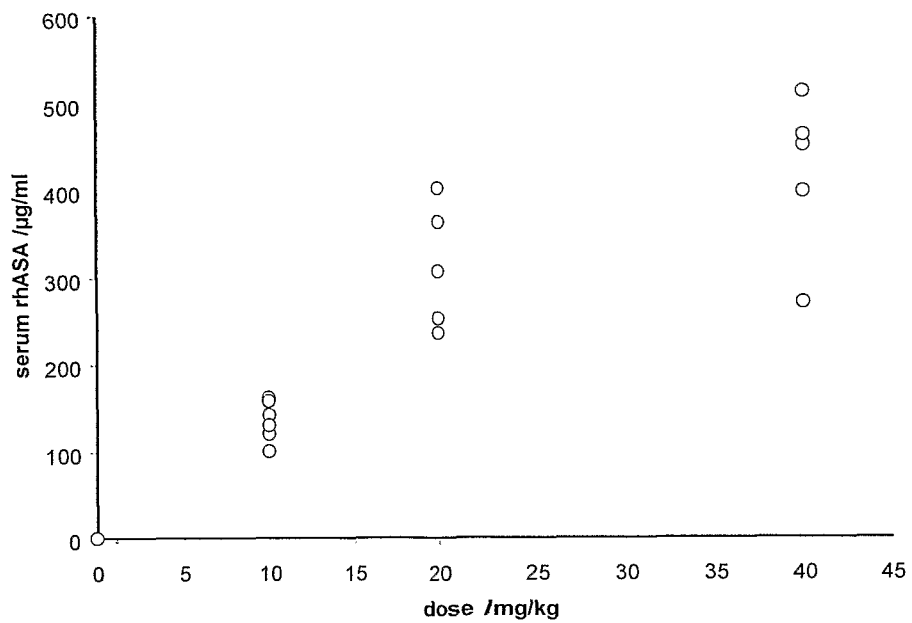

FIG. 6: rhASA serum levels 10 min after intravenous injection of rhASA

Figure 7:
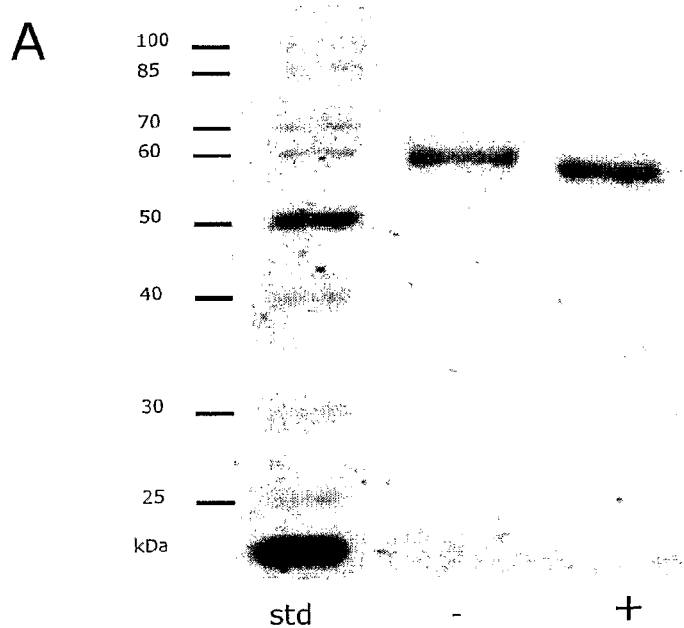
Figure 7:
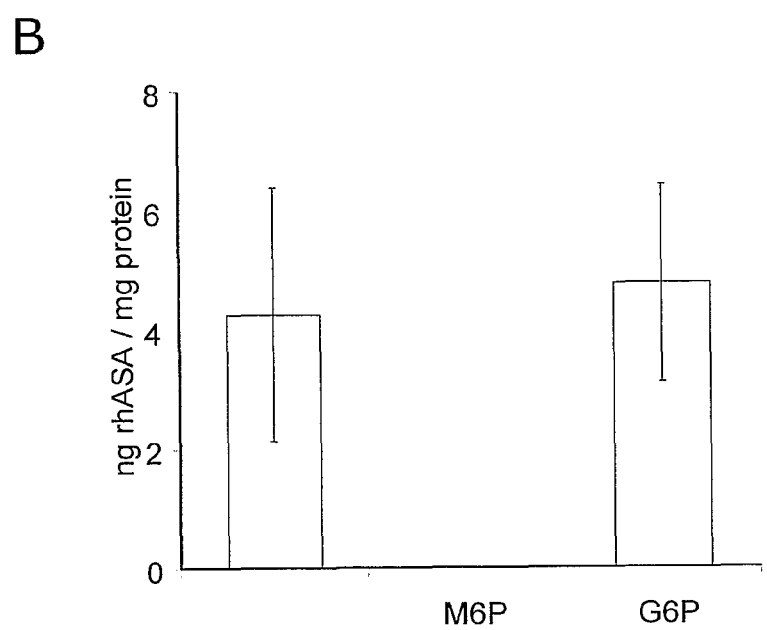

FIG. 7: In vitro analyses of CHO-rhASA. (A) SDS-PAGE of native (−) and deglycosylated (+) enzyme. Gels were stained with Coomassie blue. The masses of protein standards (std) are indicated. Treatment with PNGase F causes a shift of the ASA band due to the loss of N-linked carbohydrates. (B) M6P-dependent endocytosis of CHO-rhASA by BHK cells analysed by ELISA. BHK cells were incubated with 1 µg CHO-rhASA per ml medium for 20 h in the presence or absence of 10 mM M6P. Other dishes were supplemented with 10 mM glucose 6-phosphate (G6P) as a control. The complete block of endocytosis by M6P indicates that BHK cells internalize CHO-rhASA via M6P receptors. This indicates the presence of M6P residues on CHO-rhASA. The data are expressed as means±SD, n=3.

Figure 8:
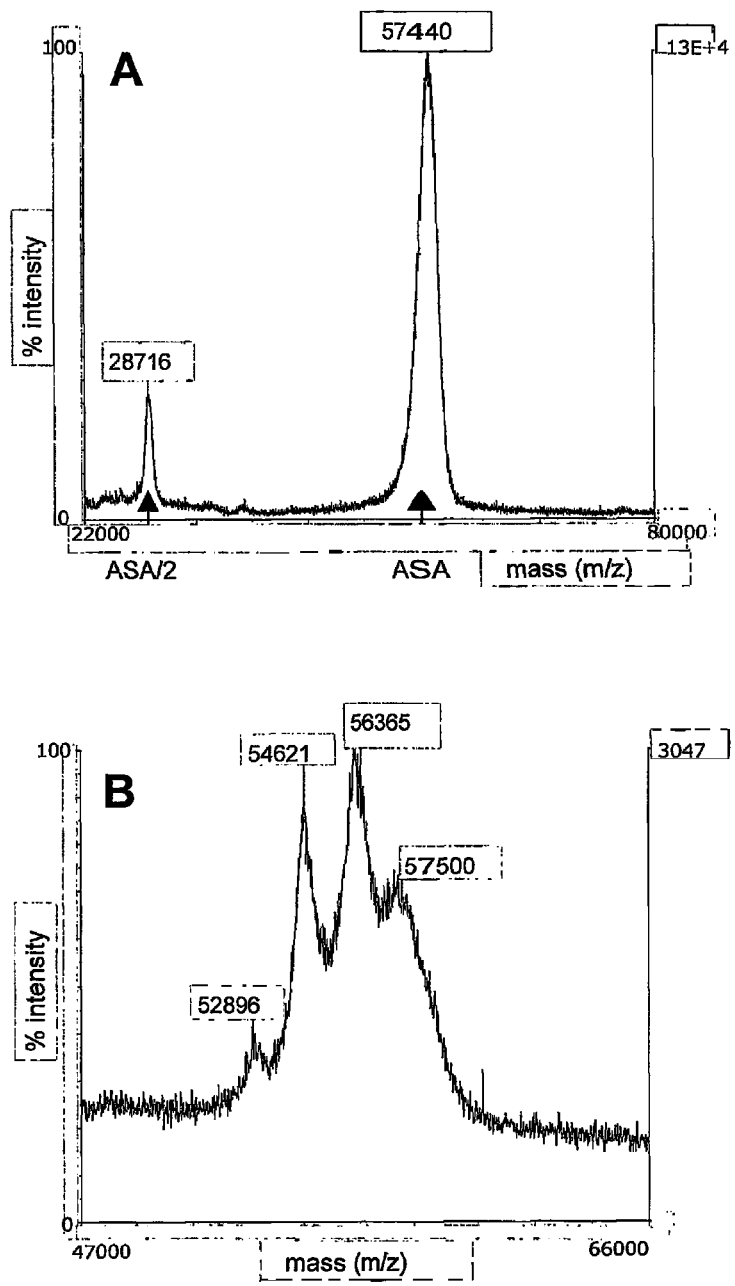

FIG. 8: (A) MALDI-TOF analysis. rhASA isolated from secretions of CHO cells exhibits a correct size of 57 kDa and the enzyme preparation lacks major contaminants. The minor peak at 29 kDa (ASA/2) represents the doubly charged molecule. (B) MALDI-TOF analysis of CHO-rhASA treated with a low concentration of PNGase F. The limited deglycosylation yields four products. They presumably represent rhASA which bears three, two, one or no N-glycan(s). The mass pattern therefore suggests that all three potential N-glycosylation sites of the CHO-rhASA are glycosylated.

Figure 9:
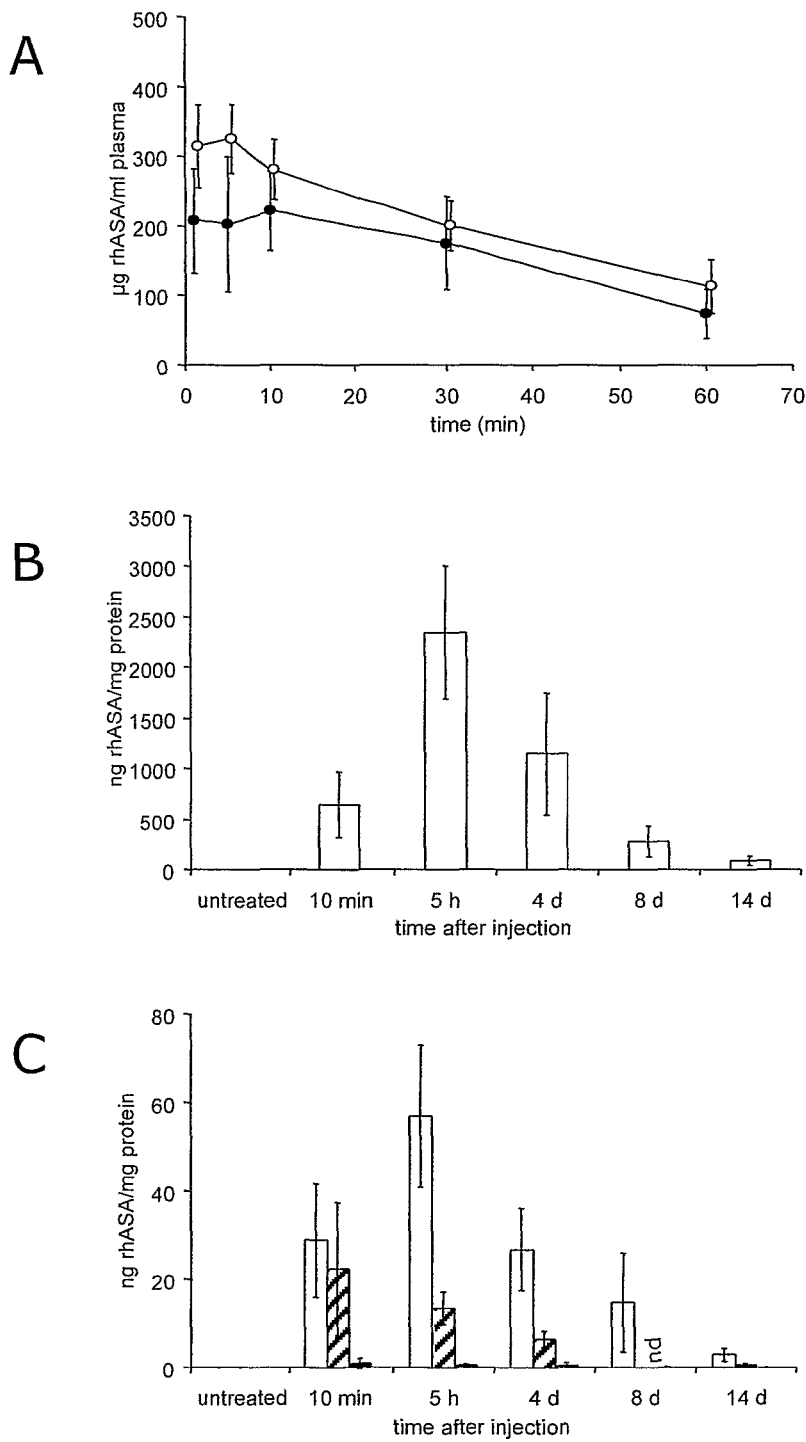

FIG. 9. Pharmacokinetics of CHO-rhASA after a single injection into the tail vein of ASA-deficient mice. All data are expressed as means±SD. (A) rhASA levels in plasma in the first hour after injection of 20 mg/kg (closed circles, n=9) or 40 mg/kg (open circles, n=11). The concentration was determined by ELISA. (B) rhASA levels in liver at various times after administration of 40 mg/kg. The concentration was determined by ELISA (n=3). (C) Tissue kinetics of rhASA after administration of 40 mg/kg in kidney (open bars), sciatic nerve (hatched bars) and brain (closed bars) as determined by ELISA (n=3). nd—not determined.

Figure 10:
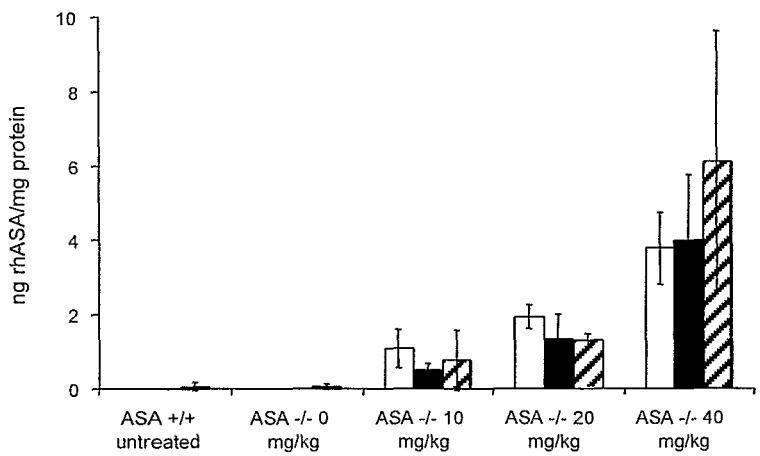
Figure 10:
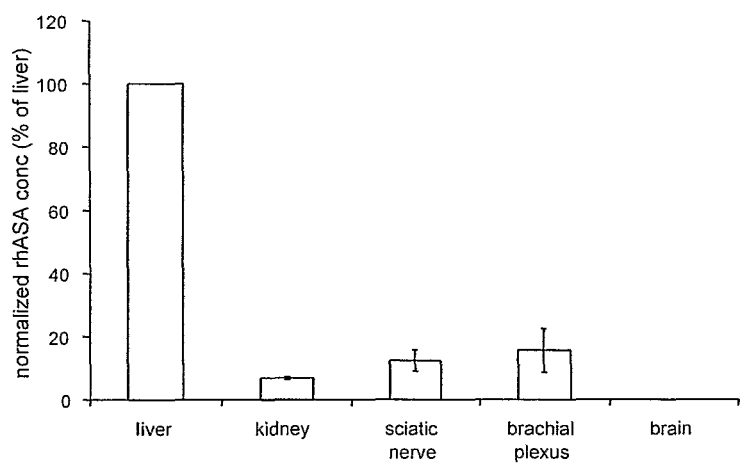

FIG. 10: Pharmacokinetics of CHO-rhASA after a single injection into the tail vein of ASA-deficient mice. All data are expressed as means±SD. (A) Tissue levels of rhASA 8 days after injection of different enzyme doses (n=5). The concentration was determined by ELISA for kidney (open bars), brachial plexus (closed bars) and sciatic nerve (hatched bars). Tissues from untreated wildtype mice and mock-treated ASA knockout mice were analysed as negative controls. Control homogenates from the sciatic nerve show some unspecific background signal since the incubation times had to be prolonged to quantify the specific immunoreactivity in the very small nerve samples from treated mice. (B) Relative tissue distribution of rhASA 8 days after injection of 20 mg/kg. The rhASA concentration was measured by ELISA and normalized on the level in liver (n=3).

Figure 11:
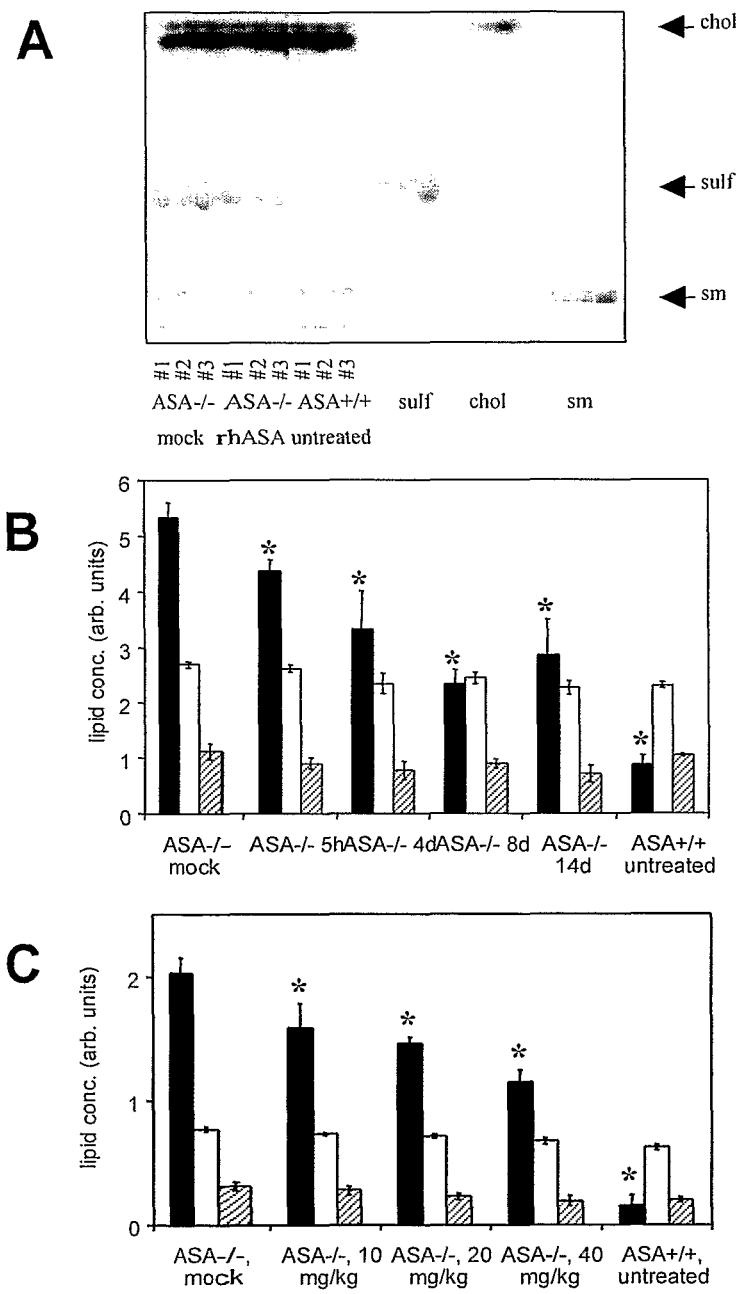

FIG. 11: Sulfatide clearance from tissues after single treatment of ASA-deficient mice with CHO-rhASA. The levels of sulfatide (closed bars), cholesterol (open bars) and sphingomyelin (hatched bars) were determined by TLC and are expressed as means of arbitrary units±SD. Asterisks indicate a statistically significant difference to mock-treated controls (student's t-test, p<0.05). (A) Analysis of kidney lipids by TLC. Lipids were extracted from kidneys of different experimental groups and incubated under alkaline conditions to hydrolyze phosphoglycerolipids and cholesterylester. The reaction products were separated by TLC, visualized and analysed by densitometry. The loading volumes were normalized on the protein concentration of the crude tissue homogenate used for lipid extraction. Increasing amounts of cholesterol (chol), sulfatide (sulf) and sphingomyelin (sm) were loaded as standards. (B) Lipid levels in kidney at different times after injection of 40 mg/kg (n=3). (C) Lipid levels in kidney 8 days after injection of different enzyme doses (n=5).

Figure 12:
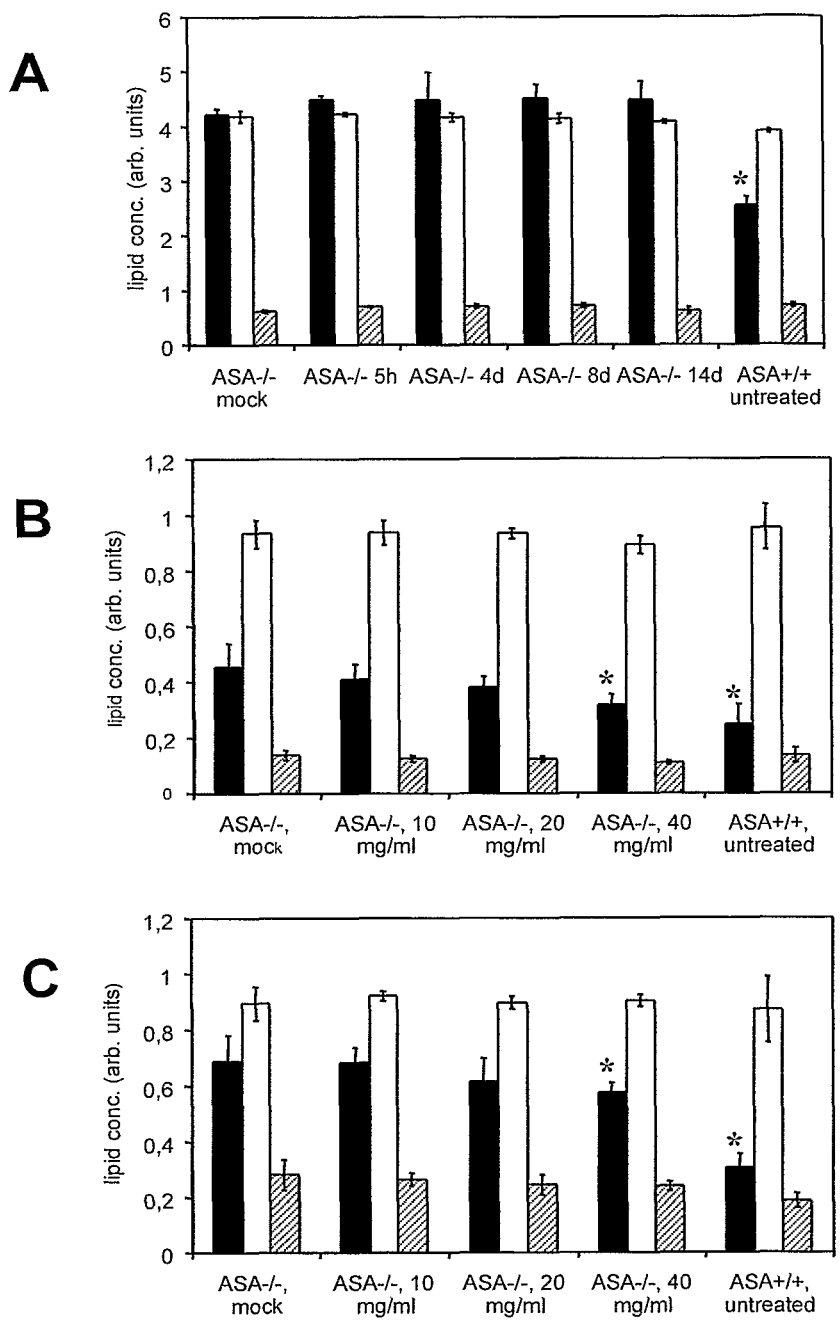

FIG. 12: Sulfatide clearance from tissues after single treatment of ASA-deficient mice with CHO-rhASA. The levels of sulfatide (closed bars), cholesterol (open bars) and sphingomyelin (hatched bars) were determined by TLC and are expressed as means of arbitrary units±SD. Asterisks indicate a statistically significant difference to mock-treated controls (student's t-test, p<0.05). (A) Lipid levels in brain at different times after injection of 40 mg/kg (n=3). (B) Lipid levels in the sciatic nerve 8 days after injection of different enzyme doses (n=5). (C) Lipid levels in the brachial plexus 8 days after injection of different enzyme doses (n=5).

Figure 13:
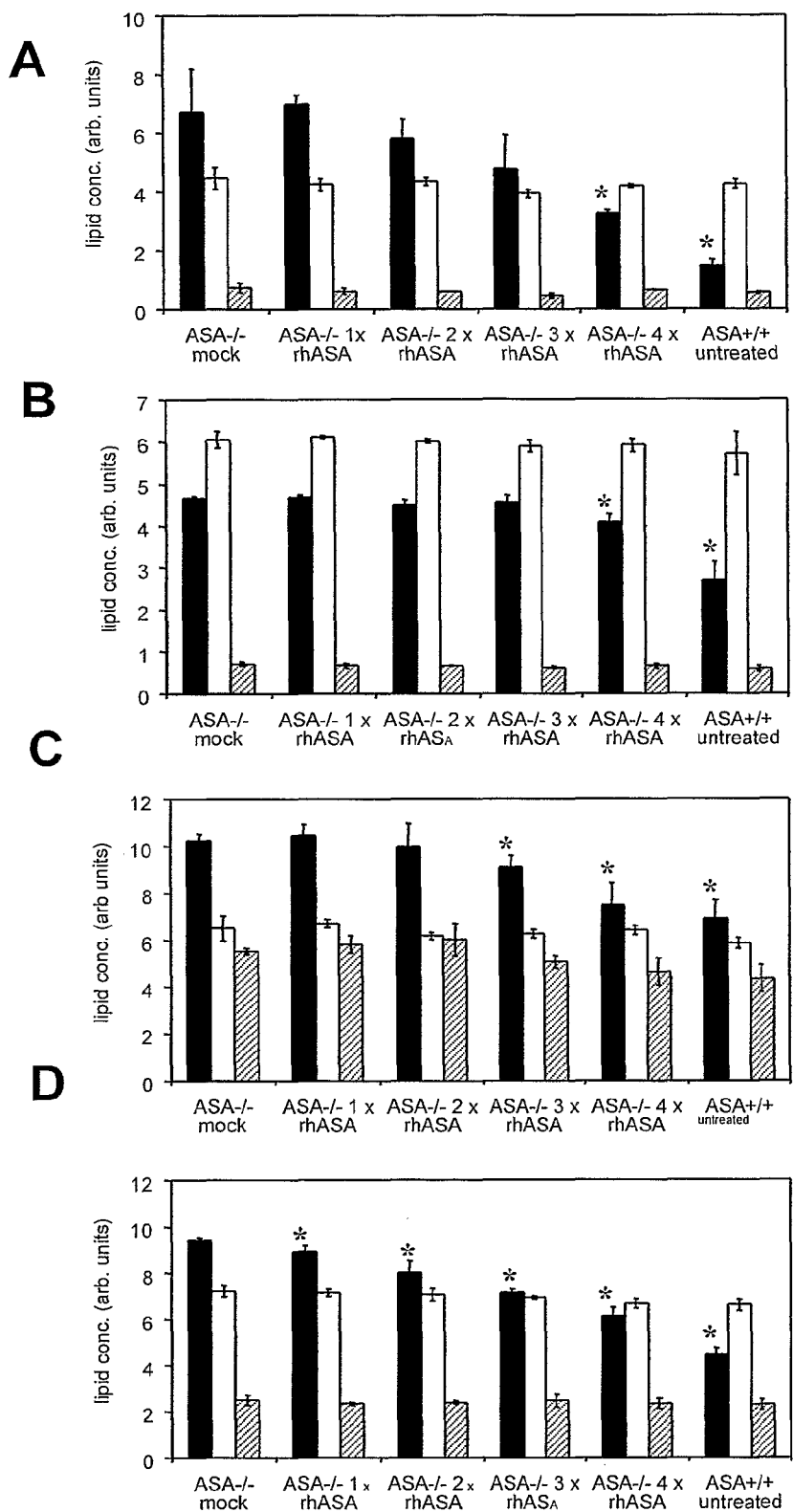

FIG. 13. Lipid levels in (A) kidney (B) brain, (C) sciatic nerve and (D) brachial plexus after repeated dosing of 20 mg CHO-rhASA/kg once weekly. The knockout mice were treated with up to four infusions of CHO-rhASA. Controls were mock-treated with four injections of buffer. The levels of sulfatide (closed bars), cholesterol (open bars) and sphingomyelin (hatched bars) were analysed 8 days after the last dosing and are expressed as means±SD (n=3). Asterisks indicate a significant difference in the sulfatide level compared to mock-treated controls (student's t-test, p<0.05).

Figure 14:
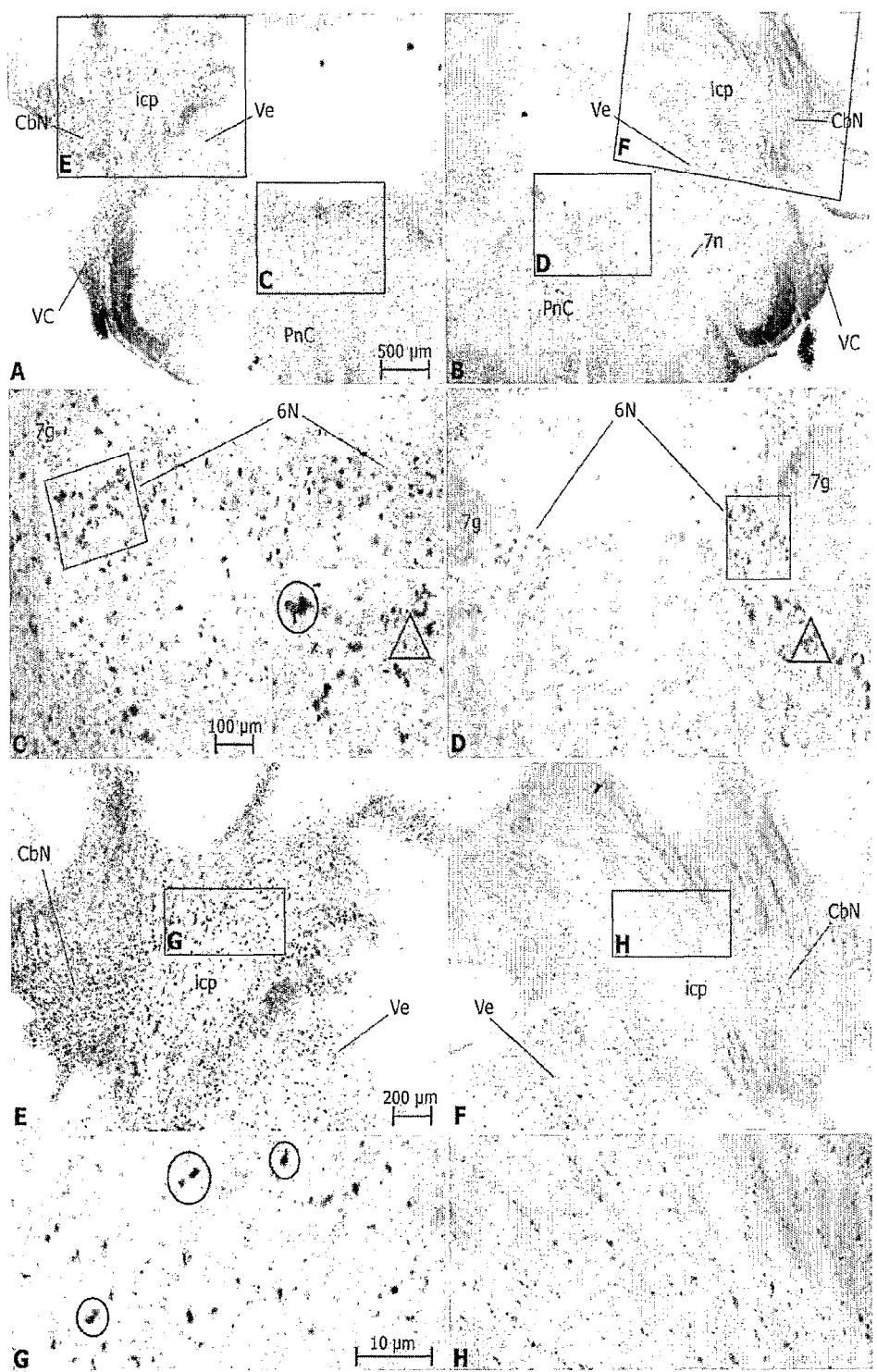

FIG. 14. Sulfatide storage in the CNS as histochemically demonstrated by incubation with alcian blue (see Methods). Coronal thick sections (100 μm) through the brain stem of a mock-treated ASA knockout mouse (A, C, E, G) and an enzyme-treated ASA knockout mouse (B, D, F, H). (A, B) overview to outline the regions shown at higher magnification in the photomicrographs below. 7n—root of facial nerve, CbN—cerebellar nucleus, icp—inferior cerebellar pedunculus, PnC—pontine reticular nucleus, VC—ventral cochlear nucleus, Ve—vestibular nucleus. (C, D) Abducens nucleus (6N) and adjacent regions. 7g—genus of facial nerve. In the mock-treated mouse alcianophilic material (sulfatide) is seen in many cells, of which phagocytes and neurons can be identified (marked by triangles and circles, respectively, in the inset). In the rhASA-treated mouse alcianophilic material is seen mainly in neurons. (E, G) and (F, H) Inferior cerebellar pedunculus (icp) as an example of a white matter tract. In the mock-treated mouse numerous large alcianophilic phagocytes are seen only a few of which are in the optic focus in G (some are marked by circles). The small alcianophilic granules may be associated to oligodendrocytes which can, however, not be identified at this magnification. In the rhASA-treated mouse the icp shows only small alcianophilic structures suggesting that the sulfatide-storing phagocytes are decreased in size and/or number. The overall staining of the cerebellar and vestibular nuclei in F is reduced since alcianophilia is restricted mainly to neurons and has largely disappeared from phagocytes. Bars: 500 μm in A and B; 100 μm in C and D; 200 μm in E and F; 10 μm in G, H and insets of C and D.

Figure 15:
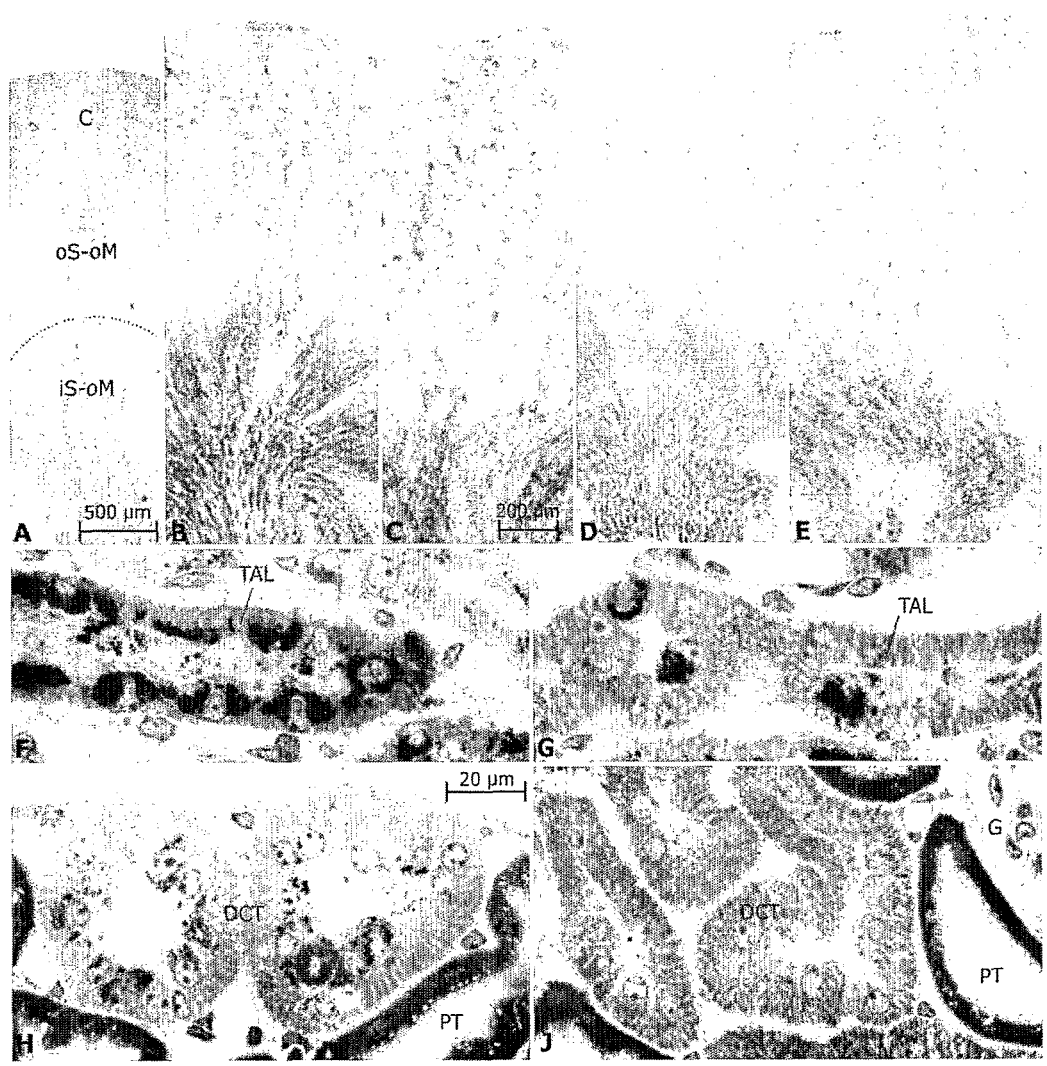

FIG. 15. Sulfatide storage in the kidney as histochemically demonstrated by incubation of 100 μm slices with alcian blue (see Methods). (A) wild type mouse; weak staining is seen in the inner stripe of the outer medulla (iS-oM), whereas the outer stripe of outer medulla (oS-oM) and the cortex (C) are unstained. (B, C) Mock-treated ASA knockout mouse. Severe sulfatide storage (alcianophilic material) is seen in the tubules of the inner stripe of outer medulla; in the outer stripe and cortex several profiles show sulfatide storage. (D, E) ASA knockout mouse treated with four doses of 20 mg CHO-rhASA/kg. The cortex is devoid of alcianophilic material. In the outer stripe staining is reduced. In the inner stripe staining appears unchanged as compared with the mock-treated animal. Bars represent 500 μm in A, B, D and 200 μm in C, E. (F-J) Semithin sections stained with toluidine blue. (F, H) Mock-treated ASA knockout mouse, thick ascending limb (TAL) in the outer stripe and distal convoluted tubules (DCT) in cortex. The intensely stained cytoplasmic inclusions correspond to lysosomes filled with sulfatide as shown previously (Lullmann-Rauch, R. et al., *Histochem. Cell Biol.,* 116, 161-169). (G, J) ASA knockout mouse treated with four doses of 20 mg CHO-rhASA/kg, representative segments of the nephron corresponding to those in F and H. The storage material is reduced in the TAL and absent from the DCT profiles. G—glomerulus, PT—proximal tubule. Bar represents 20 μm in F-J.

Figure 16:
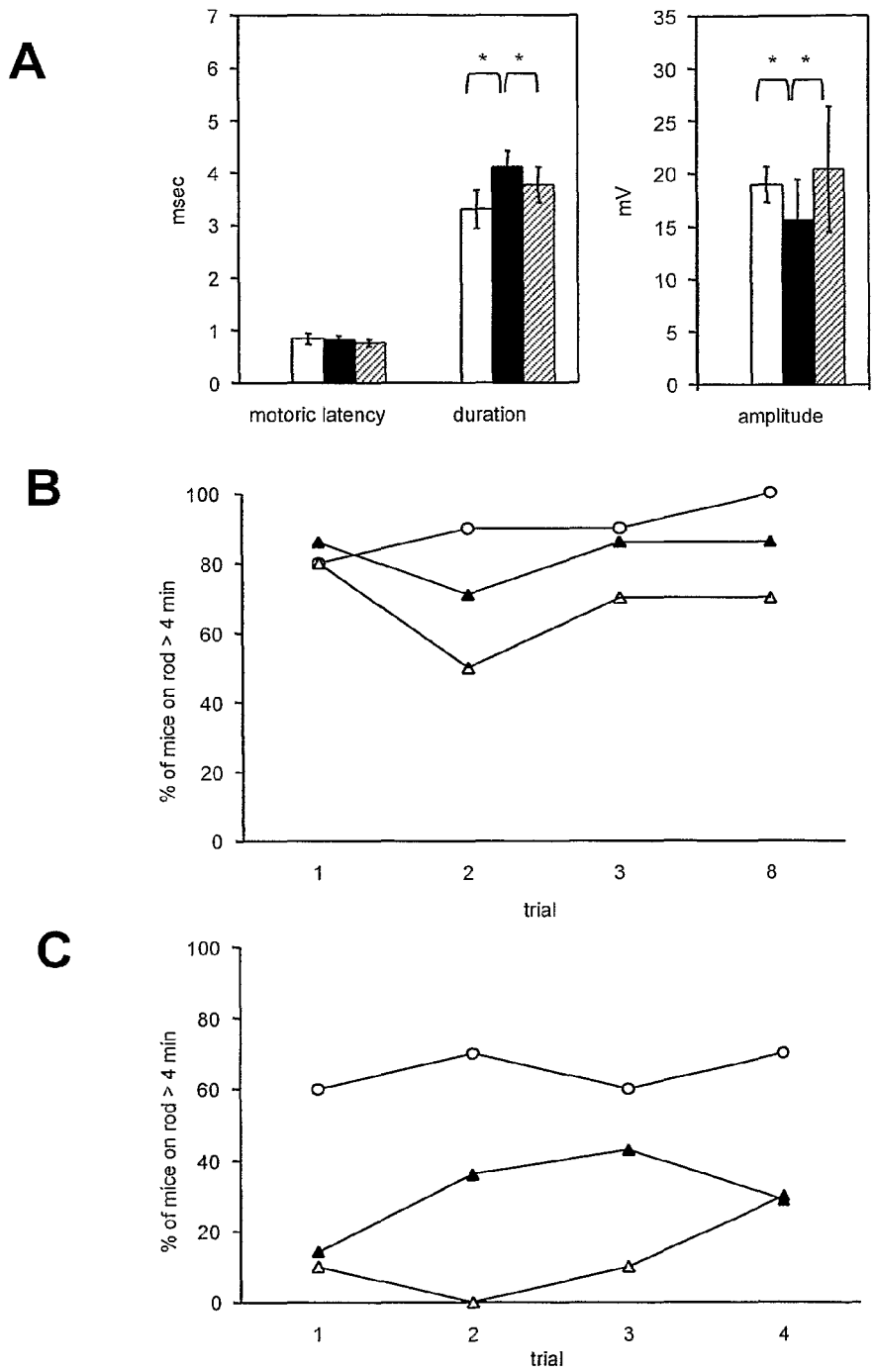

FIG. 16. Functional effects of repeated dosing with 20 mg CHO-rhASA/kg once weekly. (A) Neurophysiological parameters determined in wildtype mice (closed bars), mock-treated ASA knockout mice (open bars) and ASA knockout mice 6 days after the fourth injection of CHO-rhASA (hatched bars). The indicated parameters were measured in the intrinsic foot musculature after distal stimulation of the sciatic nerve. Data are expressed as means±SD (n=7-8). Asteriscs indicate a significant difference (student's t-test, p<0.05). (B) Rotarod performance of mice at a mean age around 9 mo (9.2±1.1 mo). ASA knockout mice (closed triangles, n=7) were analysed at day 2 and 3 after the third treatment with 20 mg CHO-rhASA/kg. Age-matched wild-type mice (circles, n=10) and mock-treated ASA knockout mice (open triangles, n=10) were analysed as controls in parallel. The percentages of mice, which were able to balance on a slowly rotating rod for at least 4 min were determined in four consecutive trials. (C) Rotarod performance of mice at a mean age of 12 mo (11.8±1.1 mo). Also in this experiment the treated mice were tested at day 2 and 3 after the third injection of 20 mg CHO-rhASA/kg. Legend and group sizes as in B, except n=14 for rhASA-treated knockout mice.

Figure 17:
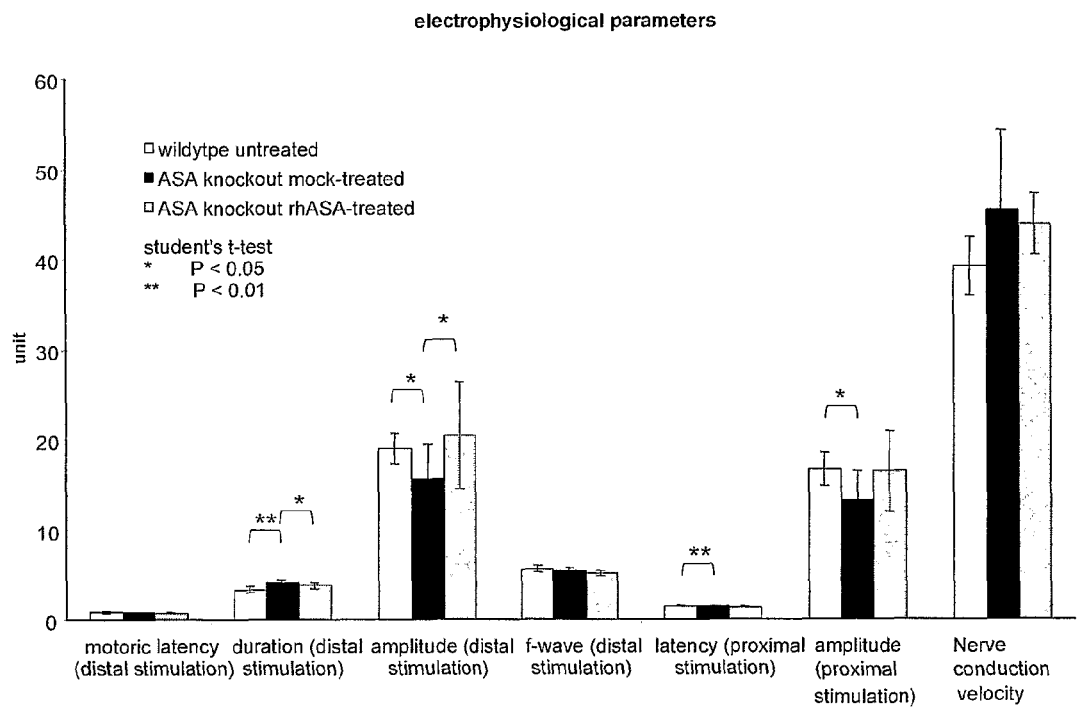

FIG. 17: Presentation of electrophysiological parameters from studies on nerve motor conductivity. (Corresponds in part to panel (A) of FIG. 16).

EXAMPLES

Example 1

Continuous Cell Propagation

A continuous cell propagation system and a small to medium size purification process for rhASA in 200-400 ml column scale intended for scale-up to large-scale production (column scale>2 L) is developed. A schematic representation of the system is given in FIG. 1. The quality and purity of the final product (rhASA) is very high and suitable for toxicology testing (including steps 1-4+7) and finally also suitable for clinical trials (including all steps described). As described above, the process will include a capture step, 1-2 intermediate purification steps, 1 polishing step, 1-2 virus removal steps and 1 formulation step. 1 or more buffer exchange steps will also be included.

Experimental Design:

Several different chromatography gels are tested and performance of the different steps (with respect to removal of contaminants, yield and purity) are analysed with a battery of analytical methods described briefly below.

Analytical Methods

| | |
|---|---|
| Enzyme activity: | Arylsulfatase assay |
| Total protein concentration: | BCA analysis |
| rhASA concentration: | rhASA ELISA |
| Purity: | rpHPLC, SDS-PAGE |
| Identity: | rpHPLC, Western Blot rhASA |
| HCP proteins: | HCP-ELISA, Western blot HCP proteins |
| Endotoxin level: | According to European Pharmacopoeia (Ph. Eur.) method 2.6.14. For i.v.-administration the acceptable value is 5 IU/kg/h. With a maximal dose of 1 mg/kg/h and a concentration of the product of 5 mg/ml, the limit is 25 IU/ml. |

| | |
|---|---|
| Osmolality: | According to Ph. Eur. method 2.2.35. Since no acceptable value is stated in the European Pharmacopoeia for this exact product the value (250-350 mOsmol/kg) is defined because it compares to an isotonic solution of (0.9%) NaCl, which is well-tolerated in-vivo. |
| DNA content: | DNA threshold |
| pH: | According to Ph. Eur. method 2.2.3. Since no acceptable value is stated in the European Pharmacopoeia for this exact product. The value (7.0-8.0) is defined because it is neutral pH and well-tolerated in-vivo. |
| Bacterial count: | Ph. Eur. method 2.6.12 (membrane filtration) will be used to test the API and Bulk Substance. There is no acceptable value stated in the European Pharmacopoeia for this exact product. The value ($\leq$10 cfu/ml) is defined to ensure an adequate minimal bioburden prior to sterilisation. The final product for i.v.-administration will be sterile and tested according to Ph. Eur. method 2.6.1 |

Description of Analytical Methods

Aryl Sulphatase Assay

In addition to its natural substrates ASA is also able to catalyze the hydrolysis of the synthetic, chromogenic substrate, para-Nitrocatechol sulfate (pNCS), see FIG. The product, para-Nitrocatechol (pNC), absorbs light at 515 nm. The method is described by Fluharty et al. 1978, Meth. Enzymol. 50:537-47

Materials and Equipment

Spectrophotometer Spectra MAX Plus from Molecular Devices or equivalent. Cuvette 1 ml (glass or plastic) with 1 cm path-length suitable for 515 nm. Flat bottomed 96 well micro-titer plate.

Chemicals and Reagents pNCS—p-NitroCatechol Sulfate (no. N-7251, Sigma)
BSA—Bovine Serum Albumin Frac. V
NaAc—Sodium Acetate trihydrate
Triton X-100
Tris-HCl molecular biology grade
PBS, pH 7.4 w/o $Ca^{2+}$, $Mg^{2+}$: 0.20 g/l KCl, 0.20 g/l $KH_2PO_4$, 8 g/l NaCl, 1.15 g/l $Na_2HPO_4$. Adjust pH.

All other solvents and chemicals were of p.a. quality (Merck)

a. 2× ASA substrate solution: 30 mM PNCS, 10% (w/v) NaCl and 1 mg/ml BSA in 0.5 M NaAc pH 5.0.
b. TBS, pH 7.5: 10 mM Tris-HCl and 150 mM NaCl in $H_2O$.
c. Stop solution: 1 M NaOH Since many anions and kations, such as $SO_4^{2-}$, $PO_4^{3-}$, $SO_3^{2-}$, F, $Ag^+$, $Cu^{2+}$ and $Hg^{2+}$, are inhibitors of the enzyme at concentrations in the millimolar range or lower the sample is transferred to a suitable buffer (e.g. TBS) before activity is measured. This is done by dialysis or buffer exchange on a gel filtration column (e.g. PD10 from Amersham Pharmacia Biotech).

a. Measurement of ASA Activity in Cell Supernatants

The used medium is centrifuged (110×g, 5 minutes) and the supernatant is transferred to a clean tube. The buffer is changed to TBS by dialysis or by using a gel filtration column.

b. Measurement of Intracellular ASA Activity

Cells in suspension are washed once with PBS and then once with TBS before they are lysed in 0.5 ml TBS+0.5% TritonX-100 for 10 minutes, RT. After vortexing the lysates are centrifuged (13.200 rpm, 10 minutes) and supernatants collected in clean tubes. Alternatively, the cells are resuspended in TBS and then lysed by repeated freeze-thawing cycles.

c. Measurement of ASA Activity in In-Process Samples and Final Product

The buffer is changed to TBS before activity is measured and protein concentration in the samples is determined using the BCA Protein Assay Reagent kit (see below).

In order to assure linearity a final absorbance between 0.1 and 2 (see reference 2) is aimed at. Samples are diluted in TBS if necessary.

a. 50 µl of sample diluent (TBS or TBS+TritonX-100) is added in at least duplicates to a micro-titer plate and use as blanks.
b. 50 µl of samples or diluted samples is added in duplicates to the micro-titer plate.
c. 50 µl of 2× ASA substrate solution is added into each well. The plate is sealed and incubated at 37°+/−0.50° C. for exactly 30 minutes.
d. The reaction is stopped by adding 50 µl of stop solution (1 M NaOH) into all wells.
e. Pre-read is done using a micro-titer plate filled with 0.15 ml MilliQ water/well to correct for scattering effects. Subsequently the absorbance at 515 nm is measured within 30 minutes using a plate reader. The absorbance measured from the micro-titer plate to a 1 cm path length by the use of an application named Path Check.
f. The delta absorbance (ΔA) is calculated by subtracting the absorbance value of the blank from the measured absorbance of each of the samples. The molar extinction coefficient (εM) for the product pNC is 12 400 M−1 cm−1.

Calculations

Definition: One Unit (1 U) of enzyme activity is defined as the hydrolysis of 1 µmol pNCS per minute at 37° C., pH 5.0.

The following equation is used in order to calculate the enzyme activity in µmol pNCS hydrolysed/min×ml (=Units/ml):

$$\frac{V_{tot} \text{ (ml)}}{\varepsilon_M / 1000 \times V_{sample} \text{ (ml)} \times \text{Incubation time (min)}} \times \Delta A = \text{Units/ml} \quad (1)$$

where:
ΔA=absorbance of sample—absorbance of blank
Vtot (ml)=total reaction volume in ml (in this case 0.15 ml)
Vsample (ml)=added sample volume in ml (in this case 0.05 ml)
$\varepsilon_M$=the molar extinction coefficient for the product pNC, which in this case is 12 400 $M^{-1}$ $cm^{-1}$ Equation 1 could more simplified be written as:

$$\Delta A \times (0.15/(12\,400 \times 1000 \times 0.05 \times 30)) = X \, \mu\text{mol}/(\text{minute} \times \text{ml})(=\text{Units/ml}) \quad (1)$$

To calculate the specific activity in µmol pNC consumed/(minute×mg) (=Units/mg) divide equation 1 with the protein concentration of the sample:

$$\text{Eq. 1/Protein conc. (mg/ml)} = Y \, \mu\text{mol}/(\text{minute} \times \text{mg}) = \text{Units/mg} \quad (2)$$

BCA Analysis

A commercially available assay kit (Pierce BCA Protein assay kit, no. 23225) is used according to the manufacturers instructions.

rhASA ELISA for Determination of rhASA Concentrations

The procedure is an enzyme-linked immunosorbent assay (ELISA) for quantitative determination of recombinant human Arylsulfatase (rhASA) in solutions, such as buffers, cell culture medium and serum.

rhASA is captured on maxisorp 96-well plates coated with the IgG fraction of rabbit antiserum to affinity-purified rhASA. The captured rhASA is detected with a monoclonal antibody to rhASA, followed by horseradish peroxidase (HRP)-conjugated anti-mouse immunoglobulins. HRP will convert the substrate tetramethylbenzidine (TMB) to a blue product, which turns yellow upon acidification. The absorbance is measured at 450 nm and a standard curve from known rhASA concentrations is used to calculate rhASA concentrations of the samples.

Equipment

Spectrophotometer for plates, i.e. Spectramax Plus, Molecular Devices with SOFtmax PRO software for calculations Plate washer Plate shaker Pipettes; single and multi-channel Materials Maxisorp 96-well plates Sealing tape Reagents Coating Buffer Tris-buffered saline (TBS): 10 mM Tris-HCl, 0.15 M NaCl, pH 7.4.

Washing Buffer

TBS (coating buffer) is supplemented with 0.1% tween-20. 1 ml tween-20 is added to 1 liter of TBS.

Blocking Buffer

SuperBlock blocking buffer in TBS (Pierce).

Dilution Buffer 10 ml blocking buffer is added to 90 ml TBS (coating buffer).

Polyclonal Immunoglobulins to rhASA

Medium from rhASA-CHO cells is affinity-purified on a column with monoclonal antibody to rhASA (5.7) cross-linked to Protein A. Rabbits are immunized with affinity-purified rhASA (DAKO) and the antisera are verified to react to rhASA with western blotting. Antiserum from rabbit is purified on HiTrap protein G column(s).

The IgG fraction is stored in 50% glycerol, 10 mM Na-Pi, 75 mM NaCl, pH 7.2 at 4° C. The protein concentration is 1.25 mg/ml, determined with BCA protein assay kit.

rhASA Standard

Purified rhASA, batch M0208, is used as a standard. The standard is purified from rhASA-CHO cell supernatant with three consecutive purification steps, DEAE sepharose, HIC octyl sepharose and Mustang Q.

The stock is stored in 50% glycerol, 10 mM Tri-HCl, pH 7.5 at 4° C. The concentration, determined with BCA protein assay kit, is estimated to 100 µg/ml.

Monoclonal Antibody to rhASA

Supernatant from a rhASA monoclonal antibody (mab) producing hybridoma (19-16-3 from Prof. Gieselmann, Bonn) is purified on a HiTrap protein A column.

The mab is stored at −20° C. in 20 mM Na-Pi, 0.145 M NaCl, pH 7.2 (PBS) supplemented with 0.02% sodium acid. A working portion is kept at 4° C. for 6 months.

HRP-Anti-Mouse Immunoglobulins

Horseradish peroxidase-conjugated, affinity-isolated, goat anti-mouse immunoglobulins are purchased from DAKO (P 0447) and stored at 4° C.

TMB Substrate.

The One-Step Substrate system containing 3,3',5,5'-tetramethylbenzidine (TMB) is purchased from DAKO (S 1600) and stored at 4° C.

Stop Solution

1 M $H_2SO_4$

Method

Coating

The stock of anti-rhASA polyclonal IgG is diluted 1:1000 in TBS to 1.25 µg/ml and 100 µl/well is added to a maxisorp the 96-well plate. The plate is incubated over night at room temperature and washed twice with ~250 µl washing buffer.

Blocking

200 µl of blocking buffer is added per well prior to incubation at room temperature under agitation for at least 15-60 minutes.

Capturing of rhASA

100 µl diluting buffer is added to all wells.

rhASA Standard:

The rhASA standard stock solution is diluted 2000 times in dilution buffer in triplicates 50 ng/ml. Triplicates of 100 µl standard are transferred to the 96-well plate and serial two-fold dilutions are prepared.

Samples:

The samples are diluted in triplicates in dilution buffer to estimated rhASA concentration around 25 ng/ml. 100 µl of each sample are transferred to the 96-well plate. 2-8 two-fold dilutions are prepared in the plate.

The plate is incubated for 100-140 minutes at room temperature and under agitation and is subsequently washed four times with ~250 µl washing buffer.

Detection with Monoclonal Antibody

The monoclonal antibody (mab) to rhASA is diluted 1:2000 to 185 ng/ml in dilution buffer and 100 µl is added to each well. The plate is incubated for 70-120 minutes at room temperature under agitation and is subsequently washed four times with ~250 µl washing buffer.

Detection of Complexed Mab with Anti-Mouse IgG-HRP

Anti-mouse IgG-HRP is diluted 1:2000 to 500 ng/ml in TBS (coating buffer) and 100 µl is added to each well. The plates are incubated for at 70-120 minutes at room temperature under agitation and subsequently washed four times as above.

Colour Development

TMB substrate (100 µl) is added to each well and the plates are incubated for 15 minutes at room temperature without agitation. The reaction by adding 100 µl/well 1 M $H_2SO_4$ (stop solution) and the absorbance is measured at 450 nm with endpoint reading in the plate spectrophotometer.

Evaluation rhASA concentrations are calculated using the SOFTmax PRO software ( . . . ) according to the manufacturers instructions.

The linear part of the standard curve is plotted using linear regression and the concentration of unknown samples is read from the standard curve.

Reversed Phase HPLC for Analysis of rhASA

The purity of Arylsulfatase A (rhASA) is determined by reversed phase HPLC, monitoring the UV absorption at 220 nm. The elution is obtained with an increasing concentration of organic modifier (acetonitrile) in the mobile phase. The retention times for rhASA and other components in the sample are dependent on their ability to adsorb and desorb to the non-polar stationary phase, which in turn depends on factors such as protein conformation, hydrophobicity and sequence.

Materials and Equipment

Hewlett Packard model 1090 HPLC system equipped with a tertiary pump system, auto injector, diode array detector, controlled by HP Chemstation version A.06.03. Equivalent HPLC systems may be used provided that the system suitability test verifies an adequate performance.

Filter for Sample Concentration:
Centriplus YM-30, Millipore corp.
Analytical Column:
Zorbax 300SB-C18, 2.1*150 mm 5-micron, Rockland Technologies Scientific, Inc.
Inline Filter:
Inline filter A-102X and inline filter cartridge 1*1 mm, Upchurch Scientific, Inc.
Filter for Sample Preparation:
Whatman Anatope 10 LC Chemicals and Reagents Milli-Q water, HPLC grade water or equivalent
Acetonitrile, far UV, HPLC grade (VWR, LiChrosolve or equivalent)
Trifluoroacetic acid (TFA), ampoules 10×1 g (Pierce)
Tris base p.a. quality (Angus or equivalent)
Guanidinium chloride p.a. quality (VWR biochemistry grade or equivalent)
Mobile Phase A:
Dissolve 1 ampoule TFA (1 g) in 1 litre of Milli-Q water
Mobile Phase B:
Dissolve 1 ampoule TFA (1 g) in 1 litre of acetonitrile
Sample Diluent:
20 mM Tris-HCl, pH 7.5
Column Cleaning Solution 1:
50% Isopropanol p.a. quality in water
Column Cleaning Solution 2:
6 M Guanidinium chloride rhASA standard (purified on a mab ASA/protein A Sepharose column. Reported in experimental summary Exp. No: M-6). If affinity purified rhASA not is available, samples of lower purity from the rhASA purification scheme may be used as a standard.

All other chemicals and reagents were of p.a. quality if not otherwise stated and purchased through common commercial sources.

Method
Instrumental Conditions

| Mobile phase composition: | A: Water, 0.1% TFA |
| | B: Acetonitrile (AcN), 0.1% TFA |
| Flow rate | 0.2 ml/min |
| Temperature: | +40° C. |
| Sample injection volume: | |
| Crude extract | 20 μl (if concentrated to 0.3 mg/ml) |
| In-process samples: | 20 μl (if concentrated to 0.3 mg/ml) |
| Affinity purified samples: | 5 μl (if 1.0 mg/ml) |

Gradient:

| Time (min) | % A | % B |
| --- | --- | --- |
| 1.00 | 70 | 30 |
| 10.00 | 40 | 60 |
| 15.00 | 5 | 95 |
| 20.00 | 5 | 95 |
| 25.00 | 70 | 30 |
| 30.00 (post time) | 70 | 30 |

Column Wash (Performed every 5$^{th}$ Injection):

Injection of 25 μl of 50% isopropanol (p.a. grade) as a sample and a run of the gradient stated above in order to clean the column.

Sample and Standard Preparation rhASA samples with a protein concentration less than 100 μg/ml are concentrated in a Centriplus centrifugal filter device (model YM-30, Millipore Corp.).

The obtained retentate is adjusted to a protein concentration of 1.0-0.3 mg/ml with 20 mM Tris-HCl pH 7.5 and filtrated through a 0.22 μm filter in order to remove any particles and precipitated proteins. In case of small sample volumes the filtration can be replaced by centrifugation at 10.000 g for 10 minutes.

Chromatography

The samples are loaded and run on the chromatograph while the temperature is kept low (+8° C.) if possible.

Integration and Calculation of Purity

Area under the curve measured at 220 nm for the rhASA peak is calculated and related to total integrated area. Purity is reported as percentage rhASA of total protein. Use the integration parameters in the appendix (designed for Hewlett Packard/Agilent Chemstation 06.03 software) as base for integration. Since integration of the rhASA main peak is not always optimal with the preset integration parameters, manual integration might be necessary. Different HPLC software might also require different integration parameters, which has to be tested individually for each system.

Evaluation

Identity:

The retention of the main peak of the sample should be within ±0.5 minutes as compared to the rhASA standard.

Purity:

The purity of the sample is determined by comparing the integrated area of the main peak compared to total integrated area. Purity is reported as % main peak (rhASA).

Raw Data

Raw data files are stored on a server or CD-ROM discs.

Appendix

Integration Parameters

Integration parameters are highly instrument and system dependent and have to be evaluated for different systems used. The integration parameters below are optimized for Agilent/Hewlett Packard ChemStation HPLC software version 06.03.

| Event | Value | Time |
| --- | --- | --- |
| Slope sensitivity | 10.0 | initial |
| Peak width | 0.2 | initial |
| Area reject | 5.0 | initial |
| Height reject | 1.0 | initial |
| Detect shoulders | drop | initial |
| Integration | OFF | 0.000 |
| Integration | ON | 5.000 |

Outline of Continuous Cell Propagation

The continuous mammalian cell propagation has been developed in B. Braun 5 L bioreactors equipped with Bio-Sep cell retention devices from AppliSens. The principle of the process presented schematically in FIG. 2. The mammalian cell are cells capable of amplification and production of foreign proteins as a suspension culture in bioreactors or large-scale fermentors.

During the process development the cell line is maintained and propagated in Excell 302 medium (catalog number 81045 from JRH Biosciences). This is a serum-free medium, which is devoid of proteins of animal or human origin. Furthermore, the medium, which does not contain phenol red, has been supplemented with insulin-like growth factor-1 (IGF-1) and with glucose. The glucose concentration is monitored and adjusted to optimal levels during the process.

The recombinant human ASA produced by the continuous culture process in B. Braun 5 L bioreactor is presently expressed in CHO DG44 cells. The amplification of the CHO cells after thawing is initiated in T-flasks and the cells are later transferred to spinner flasks. Before splitting and inoculation of the bioreactor culture, the spinner culture has a cell density of $1.3 \cdot 10^6$ cells/ml with a viability of 96%.

In preparation for the culture process the cells are transferred from the spinner flasks to the bioreactors. Data on cell densities in the bioreactor before and after inoculation can be deducted from table 1 below. Also typical initial values for viability, glucose, agitation, pH, $pO_2$ and temperature are reported.

When propagated and maintained as described above the cells do not clump, and propagate and produce as suspension cultures.

Part of the propagation, maintenance and production from the CHO DG44 culture is the harvest of 1-4 reactor volumes of media per day. To compensate for the harvest, the culture is supplemented with the same amount of fresh medium per day.

The continuous culture process can be maintained over a period of more than 500 hours, and a production phase of 2 weeks or more is preferable. In order to increase the yield it is desirable to lower the temperature from 37° C. to 32-35° C. once the plateau of the production phase is reached. Cell density values at and above the $1.2 \times 10^7$ cells/ml are obtained and productivities above 3.0 µg/cell/day resulting in >20 mg rhASA/L is demonstrated in this system. During the process the parameters; glucose, lactate, glutamine, ammonium and osmolarity are measured and controlled.

TABLE 1

| Parameters | Values |
|---|---|
| Volume | 1000 ml, 5000 ml, 15 L 100 L, 400 L, 700 L |
| Agitation | 100-165 rpm |
| Temperature | 37° (reduce to 32° C.-35° C.) |
| Re-circulation rate | 3 to 4 times the perfusion rate |
| Separation parameters | CRE above 95% |
| Bleeding | 0-10% of bioreactor volume per day |
| Glucose | 2-4 g/l |
| Lactate | 0.13-5.0 g/l |
| Oxygenation | Pure oxygen sparging + PID parameter adjustments |
| $pO_2$ | 30-40% |
| Perfusion rate | Up to 4 vol/day |
| Cell viability at inoculation | >93% |
| Cell viability in production phase | >90% |
| Cell density at inoculation | $3.6 \times 10^5$ cell/ml |
| Cell density | $10\text{-}14 \times 10^6$ cells/ml during production |
| Specific ASA production | 1.5-3.0 pg/cell/day |
| Protein output per bioreactor per day | >170 mg/day (5 L reactor volume) >1 g/day (100 L reactor volume) |
| pH | 6.8-7.3 |
| Steady production state | To be defined |

Main Parameters for the Cell Culture System. Cell Retention Efficiency (CRE) is a measure, reported as a percentage, of the efficacy with which the cell retention device separates the cells from the medium and bring back the cells to the culture vessel. Bleeding is a deliberate harvest of cell containing medium. Proportional Integral Differential (PID) parameter is relevant when controlling the way a process reaches and maintains defined set-points. Steady production-state is a set of process parameters, chosen because the are believed to support an optimal production. The aim is to maintain the process at these parameters for a longer period, the steady production-state, and harvest product during this period. Cell culture is performed in medium without serum and with the addition of less than 1 mg/L recombinant human proteins with a molecular weight of less than 10 kDa.

Outline of Purification Process

Clarification and Virus Reduction

20 L of medium (ASA activity in the range of 0.3-1.5 U/ml) is clarified through a sequence of depth filters from Millipore (Polygard D5 5 µm+Opticap FF and Opticap 0.45 µm). For virus reduction Tween 80 is added to a final concentration of 1% and left at least 30 min (over night also possible) at +4° C.

Application to Production in 15 L Bioreactor:

~300 L (1-2 U/ml) harvest/cultivation (36 days). How many filters are needed? Suggestion: Clarify every third day during perfusion, 45 L/filtration. Application to production in 100 L Bioreactor: ~2000 L harvest/cultivation. 300 L/filtration.

Concentration/Diafiltration with Tangential Flow Filtration (TFF)

The filtrate is concentrated 10-20 times in volume using TFF at transmembrane pressure (TMP) 15 psi on a Sartoflow system with a Sartorius frame (Sartorius). A Millipore Biomax 30 kDa screen type A with 0.1 $m^2$ area is used. After concentration diafiltration is performed against 20 mM Tris-HCl pH 7.5 or against 10 mM sodium phosphate buffer (standard buffer), pH 7.5, approximately 2 volumes until the conductivity is approx. 4 mS/cm. The medium was finally filtered through a Opticap 0.45 µm filter Example: To 20 L filtrate (clarified harvest) a 0.1 $m^2$ membrane is used. The expected yield is 90-100%.

Application to Production in 15 L Bioreactor:

Concentrate totally ~300 L filtrate to ~15 L (20-40 U/ml) and change 2 volumes of buffer. Suggestion: TFF every $6^{th}$ day during perfusion. Concentrate 90 L to 4.5 L, 3-4 times per cultivation.

Application to Production in 100 L Bioreactor:

2000 L to 100 L and change 2 volumes of buffer. Concentrate 300 L to 15 L, 3-4 times/cultivation.

Step 1: Capture Step—DEAE Sepharose FF (Amhersam Biotech)

Sample from step 1 (corresponding to 50,000 U of total activity) is applied on a 800 ml DEAE sepharose packed in a 70 mm diameter column (Pharmacia Index 70/500) equilibrated with standard buffer. Flow rate is 80-120 cm/hr. Protein bound to the DEAE gel is then washed with 2-3 column volumes (CV) of standard buffer followed by 2-3 CV's of 0.1 M NaCl in standard buffer.

rhASA is eluted with 3-4 CV's of 0.3 M NaCl in standard buffer. Fractions containing rhASA activity are pooled and used for further purification. Normal yield is 90% and purity approximately 30-40%.

For large scale production the capture step is preferably performed using Expanded Bed Adsorption technology—STREAMLINE DEAE A STREAMLINE DEAE is equilibrated in a Direct STREAMLINE column with sodium phosphate buffer pH 7.1+200 mM mannitol (final concentration). The resin expands to ~3 times the sedimented bed volume (SBV). The arylsulfatase A containing sample is mixed, preferably online, with 300 mM mannitol, 1:1, and applied on the column. Alternatively, the sample is stirred with a top spinner continuously after mixing. Conductivity is ~7 mS/cm. The resin is washed with 2 SBV of equilibration buffer followed by 8 SBV of sodium phosphate buffer pH 7.1+0.06 M NaCl. and the rhASA is eluted with 8 SBV sodium phosphate buffer pH 7.1+0.35 M NaCl and 4-6 SBV are collected.

Flow is upward and 300 cm/hr.
Estimated yield is 95% and estimated purity is 30-40%.
Capacity is 80 U ASA(~1 mg)/ml adsorbent.
CIP immediately.

Application to Production in 5 L and 15 L Bioreactor:
1.4 L STREAMLINE Direct 95/1.0 column=20 cm sedimented bed height (~60 cm expanded). Harvest is loaded twice/week. For a 15 L Bioreactor the load corresponds to 135 and 180 L after dilution. 5.5-8 L rhASA pool is eluted at each run.

Capacity limit of column: 80 U/ml adsorbent. Maximum rhASA load on 1.4 L adsorbent=112 000 Units (~1.4 g rhASA), which corresponds to maximum 1.2 U/ml harvest (15 mg/L if specific activity is 80 U/mg) in harvest from a 4 days-pool and max 1.7 U/ml (21 mg/L) from a 3 days-pool.

Application to Production in 100 L Bioreactor:
12.3 L STREAMLINE Direct 280 column=20 cm sedimented bed height (~60 cm expanded).

Harvest is loaded twice/week, corresponding to 900 and 1200 L load after dilution.

50-70 L rhASA pool is eluted at each run.

Capacity: 984 000 U corresponds to 1.6 U/ml (20 mg/ml) in harvest from a 4-days pool and 2.2 U/ml (27 mg/ml) in a 3 days-pool.

When using a 30-50 cm bed height and 15.4-30.8 L adsorbent capacity is 1.2-2.5 $10^6$ U, corresponding to 2.0-4.1 U/ml (4-days pool) and 2.7-5.5 U/ml (3-days-pool).

Replacing the conventional anion chromatography (DEAE sepharose FF) with Expanded Bed Adsorption technology is favoured for large scale production since it renders prior concentration/Diafiltration with Tangential Flow Filtration (TFF) (step 1) redundant.

Step 2: Intermediate Step 1—Butyl Sepharose FF (Amhersam Biotech)

Sample pool from step 2 is mixed 1:1 with 1.0 M $Na_2SO_4$ in standard buffer and applied on a 800 ml octyl sepharose FF packed in a 70 mm diameter column (Pharmacia Index 70/50) equilibrated with standard buffer+0.5 M $Na_2SO_4$. Flow rate is 60-120 cm/hr. Column is washed with 1-2 CV of equilibration buffer followed by 1-2 CV's of 1.8 M Na-Acetate in standard buffer pH 7.5. rhASA is eluted with 1.5-3 CV's of 0.9 M Na-Acetate in standard buffer pH 7.5 and fractions containing activity are pooled and used for further purification. Normal yield is 90% and purity 70-87%.

As an example, the sample from step 1 corresponding to maximum tested 53 000 U of arylsulfatase activity is applied on a 600 ml Butyl Sepharose 4FF column (packed in a Pharmacia Index 70/50 column). The capacity is 100-300 U/ml gel.

Application to Production in 15 L Bioreactor:
Volume of HIC column is from 1.1-3.5 L. Three eluates from step 1 are mixed with 33-50 L 1 M $Na_2SO_4$, and loaded twice per Bioreactor cultivation. 11 L (or 3.5 L) rhASA pool is eluted/run. On condition that the eluted rhASA can be stored without risk for bacteria contamination, the two runs on HIC could be exchanged to a single run on a larger column followed by a single steps Application to Production in 100 L Bioreactor:
~25 (or 8) L column.

Step 3: Concentration and Diafiltration with TFF

Sample pool from step 3 is concentrated to approximately 1 mg/ml with TFF against a Biomax A-screen, 30 kDa. Diafiltration is performed against 3-5 volumes of 20 mM Na-Acetate, pH 5.4-5.7. Normal yield is 90-100% and purity the same as the previous step. Alternatively, the mixture is concentrated to ~4 mg (total protein)/ml and the buffer is changed to 2 mM sodium phosphate, pH 7.5 by 6 volumes of diafiltration. Diafiltration is performed at transmembrane pressure (TMP) 15 psi with Biomax 30 kDa, screen A, polyethersulfone membrane (Millipore). Yield is 90-100% and purity is the same as step 4.

Application to Production in 15 L Bioreactor Concentrate ~11 L to ~2 L and change buffer with 6 volumes of 2 mM Na-Pi, pH 7.5. Twice/cultivation.

Application to Production in 100 L Bioreactor:
Concentrate ~80 L to ~16 L.

Optionally, concentration and diafiltration is preceded by virus-inactivation by Tween-80: The eluate from step 2 is mixed with Tween-80 ($C_{18}H_{124}O_{26}$) to a final concentration of 1% and left for at least 1 hour.

Step 4: Polishing Step

Mustang-S Membrane or Blue Sepharose (Passive Step)+ Anion Exchanger or Membrane (Active Step)

Brief Description:

A Mustang-S membrane or Blue Sepharose is coupled in series with a high resolving anion exchanger (e.g. Source-Q from Amhersam Biotech or Mustang Q membrane). The columns are equilibrated with >10 CV's of 20-100 mM Sodium Acetate pH 5.4-6.0. Sample pool from step 4 is loaded on the columns after adjustment of the pH by mixing 1:1 with 0.1 M NaAc, pH 5.6 (rhASA will pass through the Mustang-S membrane/Blue Sepharose and be captured on the high resolving anion exchanger). The Mustang-S membrane/Blue Sepharose is uncoupled and the high resolving anion exchanger is washed with 2-10 CV's of 20-75 mM Sodium Acetate pH 4.8.

The anion exchanger is re-equilibrated with >10 CV's of 20 mM Tris-HCl pH 7.5 (standard buffer) or, alternatively with 10 column volumes of 10 mM Na-Pi buffer pH 7.5. The column is washed with 0.1 M NaCl in standard buffer or, alternatively with 0.06 M NaCl in 10 mM Na-Pi, pH7.5 and rhASA is eluted with a linear gradient of 0.1-0.3 M NaCl in standard buffer or, alternatively with a gradient of from 60-500 mM NaCl in Na-Pi, pH 7.5. The active rhASA fractions are collected.

Flow rate is 100-120 cm/hr., estimated yield is 90% and purity 98-100%. Capacity>40 mg/ml for Blue Sepharose and ~30 mg/ml for Source 30Q.

Application to Production in 15 L Bioreactor:
200 ml Blue Sepharose and a 300 ml Source 30Q column run twice/cultivation. Load the pool from 4 after lowering pH by dilution 1:1 with 0.1 M NaAc pH 5.6=4 L.

Application to Production in 100 L Bioreactor:
~1.3 L Blue Sepharose and 2 L Source 30Q, twice/cultivation.

Step 5: Virus Filtration Step

Virus filtration will be performed on the product pool from step 5 using a 0.1 micron sterile filter followed by a DV 20 nano filter from Pall with an applied constant pressure of 20-50 psi. Estimated flow through in process scale is 25 L/hr.

As an alternative, 1% of Tween 20 or 80 could be applied to the supernatant (contact time 30-60 minutes) before the first concentration and diafiltration step (step 1).

Step 6: Diafiltration/Formulation Step

Tangential flow filtration (TFF) against a Millipore Biomax 30 kDa screen type A against 5-10× volumes of formulation buffer is performed. The most likely formulation buffers are presented below Formulation Buffer 1.

| | |
|---|---|
| $Na_2HPO_4$ | 3.50-3.90 mM |
| $NaH_2PO_4$ | 0-0.5 mM |
| Glycine | 25-30 mM |
| Mannitol | 230-270 mM |

Water for injection (WFI)
Formulation Buffer 2.

| | |
|---|---|
| Tris-HCl | 10 mM |
| Glycine | 25-30 mM |
| Mannitol | 230-270 mM |

Water for injection (WFI)
Formulation Buffer 3.

| | |
|---|---|
| $Na_2HPO_4$ | 3.50-3.90 mM |
| $NaH_2PO_4$ | 0-0.5 mM |
| Glycine | 25-30 mM |
| Mannitol | 230-270 mM |

Water for injection (WFI)

The pH and osmolality in both formulation buffers will be balanced to 7.5±0.2 and 300±50 mOsm/kg respectively. Final protein concentration should be according to the specification (>5 mg/ml).

Step 7: Formulation, Filling
Formulation and Dosage Form

In the development of the dosage form, the stability of rhASA is an important factor to consider. At present, all stability data points towards an aqueous stabile solution. Freeze-dried powder is currently our back-up strategy.

The options at present are the two different formulation buffers described in step 7: Formulation buffer 1 and 2.

Both these formulations are known to stabilize proteins in aqueous solutions as well as in freeze-dried powders. The pH and osmolality in both Formulation buffers will be balanced to 7.5±0.2 and 300±50 mOsm/kg respectively. Final protein concentration should be according to the specification and in the range 5-20 mg/ml.

The filling of rhASA will be performed in a production unit according to EU GMP practice and in a room classified as Class A. During production the filling zone is monitored with particle count and settle plates. The personnel are regularly trained according to EU GMP and monitored after each production with glove prints. The sterility of equipment and materials are secured by validated sterilization procedures.

Conclusion

The described purification process consists of 7 steps and two sub-batches is produced per Bioreactor cultivation. The overall yield is ~60-70%. The purity is at least 95%. The Host cell proteins content should be <200 ng/mg with a target value<100 ng/ml. To reduce HCP's further it might be necessary to reduce the yield for either the intermediate or the polishing step.

TABLE 2

Flow chart of the purification process.

| Step | In process analysis | Standing time at +5° C. of product from the step |
|---|---|---|
| Harvest | 42 | ~4 days |
| 1. Capture: EBA | 42 | 30 days |
| 2. Intermediate: Butyl Sepharose | 42, CMC-A280 nm | At least over night |
| 3. TFF | 42, CMC-A280, 38 | At least 15 days |
| 4. Polish: Blue + Source Q | 42, CMC-A280, 38 | 30 days |
| 5. Virus filtration | 42, CMC-A280 | 30 days |
| 6. TFF, bulk drug substance | 42, 34 or/and CMC-A280, 38, LAL, bacterial count, pH, osmolality, CMC-HCP ELISA | Stable |
| 7. Filling | To be decided: 42, 34 or/and CMC-A280, 38, LAL, bacterial count osmolality, HCP ELISA CMC | Stable |

TABLE 3

Analytical methods.

| Dora No | Methods for analysis |
|---|---|
| 34 | Protein determination of rhASA by BCA Protein assay Kit Microtiter Plate Protocol or OD |
| CMC-A280 | Protein determination OD at A280 nm |
| 35 | SDS-PAGE analysis of recombinant human Arylsulfatase A (rhASA) |
| 38 | Reversed Phase HPLC analysis of recombinant Human Arylsulfatase A (rhASA) |
| 9213 | Carbohydrate composition quantification of glycoproteins by reversed phase HPLC with fluorescence detection |
| 40 | Western blotting from SDS-PAGE for analysis of CHO host cell proteins |
| 43 | ELISA method for determination of CHO host cell proteins |
| CMC-HCP ELISA | ELISA method for determination of CHO host cell proteins/CMC |
| 42 | Enzyme assay for analyzing activity of Arylsulfatase A, ASA. Microtiter Plate Protocol |
| 28 | ELISA method for determination of recombinant human Arylsulfatase A (rhASA) concentrations |

TABLE 4

Analysis performed at Zymenex

| Dora No | 1.1.1.1.1 When |
|---|---|
| 9213 | After step 6 or later, occasionally |
| 43 | After step 6 or later, occasionally |
| 40 | After step 6 or later occasionally |
| 35, 28 | After any step, occasionally |

Clean in Place (CIP) Procedures:

Step 1: STREAMLINE DEAE:

Upward flow, 100 cm/hr immediately after each run. 1 M NaCl 8-10 SBV, 1 M NaOH 5 SBV to waste, then recirculation>6 hrs, $H_2O$, citric acid/HAc if needed. Store 20% EtOH.

Step 2 Butyl Sepharose:

Upward flow, ~30 cm/hr. After each run CIP at reversed flow with 1-2 CV $H_2O$-2 CV 1 M NaOH (40 min contact time), 1-2 CV $H_2O$ and 1-2 CV 20% EtOH. Store in 20% EtOH.

Steps 3 and 6 TFF Membrane, Biomax 30 kDa:

Wash with distilled water followed by 0.5 M NaOH and then 0.1 M NaOH. Store in 0.1 M NaOH.

Step 4 Blue Sepharose:

After each run CIP at reversed flow with 2 CV 1 M NaCl, 2 CV $H_2O$, 1-2 CV 0.1 M NaOH (40 min contact time), 1-2 CV $H_2O$ and 1-2 CV 20% EtOH. Store in 20% EtOH.

Source Q:

Upward flow After each run CIP at reversed flow with 2 CV 2 M NaCl, 2 CV $H_2O$, 1-2 CV 1 M NaOH (40 min contact time), 1-2 CV $H_2O$ and 1-2 CV 20% EtOH, flow rate ~30 cm/hr. Store in 20% EtOH.

Results

Data for preparations of rhASA obtained through a purification procedure as outlined above are presented in tables 5 and 6. In brief, the results show that the overall yield of the purification process correspond to 79% of the rhASA present in the starting material. The purity of rhASA in the resulting preparation corresponds to 98.0% as determined by reverse phase HPLC. Results are shown in FIG. 3. Specific conditions for the procedure for which data are shown are as follows:

Step 1-3:

As described above.

Step 4:

A 10 ml Mustang-S membrane is coupled in series with a high resolving anion exchanger (Resource-Q from Amhersam Biotech, 6 ml). The columns are equilibrated with >10 CV's of 20 mM Sodium Acetate pH 5.5, rhASA from Tox03HC20 is buffer exchanged to the equilibration buffer and loaded on the columns. After passing the Mustang-S membrane, rhASA will be captured on the Resource-Q column. The Mustang-S membrane is uncoupled and the Resource-Q column is washed with 3 CV's of 75 mM Sodium Acetate pH 4.8.

The Resource-Q column is washed with >10 CV's of 20 mM Tris-HCl pH 7.5 (standard buffer) until the correct pH is reached. The column is washed with 0.1 M NaCl in standard buffer and rhASA is eluted with a linear gradient of 0.1-0.3 M NaCl in standard buffer. Fractions containing active rhASA are collected.

TABLE 5

Purification scheme Tox03HC20, which have been used for evaluation of the polishing step. Enzyme activity in the scheme may vary due to changes of the method during development

| Step | Volume (ml) | Total Activity (U) | Yiel(% activity) | Purity (% by rp-HPLC) |
|---|---|---|---|---|
| TFF | 7990 | 54358 | n.d. | n.d. |
| Capture: DEAE | 2250 | 61537 (high?) | n.d | n.d. |
| Intermediate: Butyl | 720 | 42768 | n.d | n.d |

TABLE 5-continued

Purification scheme Tox03HC20, which have been used for evaluation of the polishing step. Enzyme activity in the scheme may vary due to changes of the method during development

| Step | Volume (ml) | Total Activity (U) | Yiel(% activity) | Purity (% by rp-HPLC) |
|---|---|---|---|---|
| TFF | 655 | 49125 (based on average activity 75 U/ml)* | 90% (slightly on the high side) | 92% | n.d. = not determined

TABLE 6

Result from polishing test development in small scale using Tox03HC20 as start material. Test Mustang-S (passive) + Resource-Q (active) as polishing step.

| Step | Volume (ml) | Total Activity (U) | Total protein (mg) | Specific activity (U/mg) | Yield (% activity) | Purity (% by rp-HPLC) |
|---|---|---|---|---|---|---|
| Start: Tox03HC20 | 3.2 | 293 | 11 | 26.6 | 100. | 91.2% |
| Polishing pool | 19.0 | 249 | 8.7 | 28.5 (purification factor of 1.07) | 85% (based on activity) 79% (based on protein) | 98.0% |

Product Specification

Specification Bulk substance for i.v. Toxicology testing of recombinant human Arylsulfatase A (rhASA). The analytical tests are performed before sterile filtration and filling in vials at the end of the purification process.

Description:

Recombinant human Arylsulfatase A (rhASA) in solution for i.v. administration

Shelf life is 6 month from production if stored at −20° C. In-use time is 1 week from thawing if stored at +5° C.

| TEST | METHOD NO. | LIMIT |
|---|---|---|
| | Content | |
| rhASA specific activity (Units/mg) | Enzyme activity of rhASA | ≧50 U/mg Actual: 60-120 U/mg |
| rhASA protein concentration (BCA) (mg/ml) | 2500-P-1034 | ≧5 mg/ml |
| | Identity | |
| Retention time main peak on HPLC (relative to standard) | 2500-P-1038 | Approved |
| | Purity | |
| HPLC (% main peak) | 2500-P-1038 | >95% Actual: >97% |
| Host cell proteins (HCP) (ng/mg protein) | 2500-P-1041 | <200 ng/mg Actual: 50-100 ng/mg |

| TEST | METHOD NO. | LIMIT |
|---|---|---|
| Other Tests | | |
| Bacterial count, membrane filtration (cfu/ml) | Ph.Eur. | ≦10 cfu/ml |
| LAL (IU/mg) (max 2.5 mg rhASA/kg) | Ph.Eur. | ≦2 IU/mg rhASA |
| Osmolality (mOs/kg) | Ph.Eur. | 250-350 |
| pH | Ph.Eur. | 7.2-8.2 |

Example 2

Test of rhASA for Binding to Cation Exchange Resin and Anion Exchange Resin

Experimental Description:

rhASA (Tox03HC20) 5 mg/ml was mixed 1:10 with buffers at pH 4.8-7.2 Kation exchanger (Unosphere-S, BioRad)+ Anion exchanger (DEAE FF, Amhersam Biotech) was portioned in test tubes and equilibrated with 20 mM Na-Acetate pH 4.8, 5.2, 5.6 and 6.05 or 20 mM Tris-HCl pH 7.2. (approx. 100 µl IEX media/tube). 170 µl rhASA 1:10 in resp. buffer was added to the the IEX media with the same pH+to empty reference tubes. Mix several times and let sit for approx. 30 minutes. Spin down and measure activity in Supernatant.

Conclusion:

rhASA binds as expected to the cation exchanger, but not to the anion exchanger. Even at pH 4.8 rhASA binds strongly and unexpected to the resin. This binding may be explained by strong polarity or alternatively by a change from dimer to octamer below pH 5.8, which induces changes in exposed charged groups. Results are shown in FIG. 2.

Example 3

Degradation of Natural Sulfatides in Fibroblasts by rhASA Dose/Response Experiment Experimental Design Fibroblasts from a MLD patient with null-mutation (GM00243, purchased from Coriell Cell Repository, USA) are grown almost to confluency in 25 cm² flasks with medium containing heat-inactivated fetal calf serum (FCS). Cells are loaded with the natural substrate, $^{14}$C-palmitoyl sulfatide (15 µM). Following incubation for 40 h the medium is changed to rhASA containing medium (0, 25, 50 and 100 mU/ml affinity-purified rhASA, respectively). After 24 h the cells are harvested and lipid extracts are prepared from the cells by a chloroform-methanol extraction. The lipid fractions are analysed by TLC-chromatography by comparing to radioactively labelled references. The TLC plate is exposed to X-ray film and the different lipid fractions from the TLC plate are quantified using liquid scintillation counting. The data is expressed as percent of radioactivity of remaining and metabolised sulfatides.

Results

The data from this experiment (Table 3 and FIG. 4) shows that all dose levels of rhASA used (0.25, 2.5, 25, 50 and 100 mU/ml) metabolise approximately 40-70% of the $^{14}$C labelled sulfatide loaded into the MLD fibroblasts. The background degradation of the substrate is approximately 15% in cells not incubated with rhASA. This background may be explained by a low residual activity of sulfatases in the MLD cells, or some sulfatase activity from the heat-inactivated serum, even though no ASA activity can be detected in the cells or the FCS. This can also explain the low sulfatide metabolism in the control cells in which no rhASA is added.

TABLE 7

Degradation of radiolabelled sulfatide in MLD fibroblasts with or without the addition of recombinant human arylsulfatase A (rhASA). The results are given as percent of recovered radioactivity in the cellular lipid fraction.

| | Experiment | | | | | |
|---|---|---|---|---|---|---|
| | A | B | Mean | C | D | Mean |
| Added arylsulfatase A (mU/ml) | 0 | 0 | | 25 | 25 | |
| Metabolised sulfatide (%) | 17.3 | 15.8 | 16.6 | 68.7 | 67.6 | 68.2 |
| Remaining sulfatide (%) | 82.7 | 84.2 | 83.4 | 31.3 | 32.4 | 31.8 |

| | Experiment | | | | | |
|---|---|---|---|---|---|---|
| | E | F | Mean | G | H | Mean |
| Added arylsulfatase A (mU/ml) | 50 | 50 | | 100 | 100 | |
| Metabolised sulfatide (%) | 69.0 | 68.7 | 68.9 | 68.5 | 69.1 | 68.8 |
| Remaining sulfatide (%) | 31.0 | 31.3 | 31.1 | 31.5 | 30.9 | 31.2 |

Time-Course Experiment:

Experimental Design

Cells are loaded with $^{14}$C-palmitoyl sulfatide (15 µM) as described above. The medium is changed to medium containing 25 mU/ml affinity-purified rhASA and harvested at 6, 24 and 48 hours. Lipid extracts are prepared and analysed as a described above. The data is expressed as percent of radioactivity of remaining and metabolised sulfatides.

Results

The data from this experiment illustrate that the metabolism of the $^{14}$C labelled sulfatide loaded into the MLD fibroblasts increases over 48 hours after addition of affinity-purified rhASA. Data are shown in FIG. 5.

Conclusion:

From these data it can be concluded that rhASA is efficiently taken up by fibroblasts from a MLD patient and that sulfatides loaded into these fibroblasts can be efficiently metabolised by the exogenous rhASA even at low doses and after incubation for a few hours.

Example 4

Characterisation and Use of CHO-rhASA Produced and Purified in Large Scale

Characterization of the CHO-rhASA

Human ASA was purified from secretions of chinesei hamster ovary (CHO) cells overexpressing the human ASA from the expression plasmid pASAExp1 (Zymenex A/S, Hillerød, Denmark—former HemeBiotech A/S). The specific activity of the enzyme preparation was above 60 U/mg. The CHO-rhASA was rebuffered in 1×TBS pH 7.4 to a concentration of 2.5-4.3 mg/ml and analysed by SDS-PAGE and MALDI-TOF spectroscopy. MALDI mass spectra were collected using a Voyager-DE STR BioSpectrometry workstation (Perspective Biosystems, Inc., Framingham, USA) equipped with a 337 nm nitrogen laser. Measurements were taken manually in linear, positive ion mode at a 20-24 kV acceleration voltage, 90% grid voltage and 200 ns delayed ion extraction. Each mass spectrum obtained was the sum of 300 unselected laser profiles on one sample preparation. Sinapinic acid was used as matrix. For partial or complete deglycosylation of CHO-rhASA 1 μg enzyme was reacted with 1 or 500 mU PNGase F (Roche Diagnostics, Mannheim, Germany) for 20 h at 37° C. The endocytosis assay was done with 1 μg CHO-rhASA per ml medium for 20 hr as described (Matzner, U. et al. *Gene Ther.*, 7, 805-812). ASA was measured by an indirect sandwich ELISA and an activity assay (Matzner U, et al. (2000) Gene Ther. 7(14):1250-7, Baum, H. et al. (1959). *Clin. Chim. Acta.*, 4, 453-455).

Results

SDS-PAGE and MALDI-TOF analysis of CHO-rhASA preparations detected a compound of correct size and the absence of contaminants (FIGS. 7A and 8A). Wildtype human ASA has three N-linked carbohydrates with a combined molecular mass of approximately 5-6 kDa (Gieselmann, V. et al. (1992), *J. Biol. Chem.*, 267, 13262-13266). Treatment with PNGase F reduced the apparent molecular mass of CHO-rhASA indicating glycosylation of the recombinant enzyme (FIG. 7A). After reacting the CHO-rhASA with low concentrations of PNGase F MALDI-TOF analysis revealed four deglycosylation intermediates (FIG. 8B), possibly representing the polypeptide linked to three, two, one and no N-linked glycan(s). The mass difference between the products with the highest and the lowest mass is in the range of 5 kDa suggesting full glycosylation of the enzyme. To evaluate the mannose phosphorylation of CHO-rhASA, the mannose 6-phosphate (M6P)-dependent endocytosis of the enzyme was evaluated by an in vitro feeding assay. The assay revealed efficient endocytosis of CHO-rhASA by BHK cells (FIG. 7B). Furthermore, uptake could be completely blocked by M6P, but not by glucose 6-phosphate. It can be concluded that CHO-rhASA bears M6P residues.

Discussion

Cell culture experiments revealed that CHO-rhASA bears M6P residues and uses the M6P receptor-dependent pathway for cell entry (FIG. 7B). The BHK cells which were utilized in this in vitro assay do not express other receptors for lysosomal enzymes. It is therefore possible that other receptors such as the mannose receptor or the asialoglycoprotein receptor compete for the binding and endocytosis of substituted CHO-rhASA under in vivo conditions.

Example 6

Administration of Recombinant Human rhASA to Arylsulfatase A Deficient Mice

Materials and Methods

Human recombinant arylsulfatse A was produced as described in example 1. The batches of rhASA used for animal studies included G0301 (concentration was 4 mg/ml and the enzyme activity was 166 U/ml) and G0302 (concentration was 4.3 mg/ml and the enzyme activity was 242 U/ml). The rhASA was stored at −20° C. Before start of experiment the enzyme batches were thawed and pooled and the protein content and enzyme activity was analysed. The rhASA in this pool is diluted with TBS so the injection volume was 250-300 μl in all animal groups. The dilutions were made immediately before injection. The body weight and the dose volume were noted for each animal.

Treatment of the Mice

ASA knockout mice and wildtype controls with the mixed genetic background C57Bl/6J×129ola (Hess B, et al. (1996) Proc Natl Acad Sci USA. 93(25):14821-6) were kept under standard housing conditions in accordance with the current German law on the protection of animals. All experiments were approved by the local committee for animal welfare (Bezirksregierung Köln, reference number 50.203.2-BN 24, 18/04). Experiments were done with 8-12 mo old animals. Depending on the animal weight and the concentration of the CHO-rhASA stock, 200-300 μl enzyme solution (CHO-rhASA in 1×TBS pH 7.4) was administered by an intravenous bolus injection into the tail vein. Control animals were injected with 250 μl 1×TBS pH 7.4.

Analysis of Mice

During the treatment period blood was taken from the tail vein. For the final analysis mice were deeply anaesthetised using an intraperitoneal injection of tribromoethanol and transcardially perfused. For histological investigations mice were first perfused with PBS and then with 6% glutaraldehyde in 100 mM phosphate buffer pH 7.4. Tissues were then dissected and processed as described below. For biochemical analyses, mice were perfused with PBS alone. Kidneys, liver, brain, brachial plexus and sciatic nerves were dissected, weighed and frozen. Tissue samples were homogenized in 1×TBS pH 7.4. Aliquots of the homogenates were used for lipid extraction (see below), protein determination (BioRad Dc assay, BioRad, Hercules, USA) and measurements of ASA by ELISA (9).

Lipid Analysis

Aliquots of tissue homogenates (see above) were centrifuged at 100,000× g for 1 h and the pellet was first extracted with 5 ml chloroform/methanol (C/M) 2:1 (v/v) and then with 5 ml C/M 1:1 at 60° C. for 4 h in each case. Following evaporation of the solvent the dry lipids were redissolved in 5 ml MeOH. Alkaline methanolysis was started with 125 μl 4 N NaOH at 37° C. and stopped after 2 h with 20 μl 100% acetic acid. Lipids were dried and dissolved in 1 ml MeOH. For desalting by reverse phase chromatography Lichroprep RP-18 columns (Merck, Darmstadt, Germany) with a bed volume of 1 ml were equilibrated with C/M/0.1 M KCl 6:96:94. After adding 1 volume of 0.3 M ammonium acetate to the lipid solution the mixture was loaded onto the column. After washing with 6 ml $H_2O$, lipids were eluted with 1 ml MeOH and then with 6 ml C/M 1:1. Aliquots of the lipid extracts were sprayed onto silica gel 60 plates (Merck) using the Automatic TLC Sampler 4 from CAMAG (Muttenz, Switzerland). Loading volumes were normalized on the protein concentration of the crude homogenates used for lipid extraction. Different amounts (0.5-8 μg) of lipid standards (cholesterol, sphingomyelin, sulfatide, all standards from Sigma) were loaded on separate lanes. After thin-layer chromatography (TLC) with $C/M/H_2O$ 70:30:4 as a solvent system lipids were visualized according to Yao and Rastetter (33). The plates were scanned with a flat bed scanner (PowerLook III from UMAX Data Systems, Hsinchu, Taiwan) and the intensities of lipid bands were determined with the analysis software Aida 2.11 (Raytest, Straubenhardt, Germany). The amount of cholesterol, sphingomyelin and sulfatide are expressed as arbitrary units representing the intensities of the respective TLC band after background correction. Statistical analysis was performed using Student's t-test.

Histology

Kidneys, spinal cord and brain were dissected from perfusion-fixed mice. For the detection of sulfatides, tissue slices (100 μm thick) were prepared with a vibratome and incubated with alcian blue (Alcec Blue, Sigma-Aldrich, Taufkirchen, Germany) as described (Wittke, D. et al. *Acta Neuropathol. (Berl.)*., 108, 261-271). The histochemical conditions (pH 5.7, 300 mM $MgCl_2$) were such as to warrant specific staining of sulfatides (Scott, J. E. and Dorling, J. (1965), *Histochemie*, 5, 221-233). Paraffin sections from kidney blocks were prepared after pre-embedding incubation with alcian blue. Sciatic nerves and kidney samples were embedded in araldite according to routine methods for preparing semithin sections, either with or without pre-embedding incubation in alcian blue.

Results:

Pharmacokinetics and Biodistribution of CHO-rhASA after Single Dosing

ASA knockout mice were first treated by a single injection of CHO-rhASA into the tail vein. To determine the rate of rhASA clearance from the circulation, plasma levels of enzyme were analysed at different times after infusion of 20 or 40 mg enzyme per kg body weight (FIG. 9A). For both doses the plasma levels reached a maximum in the first minutes after injection and declined from then on. Irrespective of the administered dose, rhASA was cleared from plasma with a half time of approximately 40 min. To evaluate the kinetics of tissue uptake, mice were perfused at different times after infusion and several organs were analysed for rhASA concentrations. Immunoreactivity for rhASA could be detected already 10 min after a single treatment with 40 mg/kg in all tissues (FIGS. 9B and C). In liver which acquired the highest enzyme concentration (see below) the enzyme levels increased around 4-fold within the next five hours and dropped thereafter until day 14 to approximately 4% of the maximum level (FIG. 9B). The kinetics were similar for kidney, sciatic nerve and brain (FIG. 9C). Independent of the differences between the tissue-specific uptake rates, the enzyme was eliminated from all tissues within a comparable time course. Thus, the half life of immunologically detectable rhASA in liver, kidney, sciatic nerve and brain ranged around 4 days (FIGS. 9B and C). It is striking that the maximum concentration of rhASA differed by more than three orders of magnitude between liver and brain 5 h after infusion (FIGS. 9B and C). To analyse the biodistribution of rhASA in more detail, ASA knockout mice were infused with increasing doses of rhASA and tissues were analysed 8 days later by ELISA. A roughly linear, dose-dependent increase of the enzyme concentration could be detected in kidney and peripheral nerves (FIG. 10A). The majority of the infused enzyme was found, however, in liver (shown for 20 mg/kg in FIG. 10B). Compared to liver the rhASA concentrations were around 7% in kidney, <0.05% in brain and 12-15% in sciatic nerve and brachial plexus. Taking the different masses of these tissues into consideration it can be calculated that around 97% of the retrievable enzyme was found in liver, around 3% in kidneys and below 0.1% in the CNS and peripheral nerves.

Reduction of Sulfatide Levels after Single Dosing of CHO-rhASA

To evaluate the therapeutic potential of CHO-rhASA treatment, ASA knockout mice were intravenously infused with a single dose of 40 mg CHO-rhASA per kg body weight and lipids were extracted from kidney 8 days later. TLC of the lipid extracts revealed a prominent decline of sulfatide levels compared to mock-treated controls (FIG. 11A). The time dependence of sulfatide reduction was investigated in a second experiment. For that purpose sulfatide levels were determined in kidneys at different times after injection of 40 mg/kg (FIG. 11B). Significant clearance of sulfatide could be detected already 5 h after infusion and the extent of reduction increased until day 8. At that time around two thirds of the excess sulfatide were cleared from kidney. Six days later sulfatide reappeared and the residual mean sulfatide level rose by approximately 22%. To determine the dose-dependence of sulfatide reduction, mice were treated with different doses of CHO-rhASA and analysed 8 days later. Already 10 mg/kg resulted in a significant decline of sulfatide storage in kidney (FIG. 11C). The extent of sulfatide clearance increased with increasing doses and a roughly linear relation between dose and loss of sulfatide was detectable. To evaluate effects of enzyme replacement on the lipid catabolism of the nervous system, total brain, sciatic nerve and brachial plexus from the differently treated animals was also analysed. Compared to kidney, where sulfatide levels increased around 10-fold in aged ASA knockout mice (FIGS. 11B and C), the nervous system showed only a roughly 2-fold elevation of sulfatide levels (FIGS. 12A-C and FIGS. 13B-D). Single dosing with 40 mg/kg had no effect on sulfatide storage in the brain (FIG. 12A). A significant decline was, however, detectable in the sciatic nerve (FIG. 12B) and the brachial plexus (FIG. 12C) after administration of 40 mg/kg. Also enzyme levels of 10 and 20 mg/kg reduced the mean sulfatide storage in peripheral nerves, but the difference to control tissues was statistically not significant (FIGS. 12B and C).

Reduction of Sulfatide Storage after Repeated Dosing of CHO-rhASA

The unexpected high efficacy of single enzyme doses in reducing sulfatide levels in peripheral tissues provided the rationale to evaluate the therapeutic potential of repeated injections. We chose a treatment schedule based on up to four injections of 20 mg CHO-rhASA/kg once a week. Sulfatide levels were analysed 8 days after the last injection in kidney, peripheral nerves and brain of mice treated by one, two, three or four injections (FIG. 13).

TLC revealed that sulfatide declined progressively with an increasing number of infusions in all peripheral tissues. After the fourth treatment ~65% of excess sulfatide was cleared from kidney and brachial plexus (FIGS. 13A and D) and ~82% from the sciatic nerve (FIG. 13C), respectively. In brain no decline of sulfatide was detectable after the first, second and third treatment (FIG. 13B). After the fourth treatment, however, the sulfatide level was significantly reduced by 13% on average. This represents a clearance of 30% of excess sulfatide from brain.

To verify the sulfatide reduction in the central nervous system of mice treated by four injections, histological analysis of brain and spinal cord was performed. In the CNS white and gray matter of mock-treated knockout mice, the sulfatide storage pattern was identical to the pattern previously described for ASA knockout mice (Wittke, D. et al. *Acta Neuropathol. (Berl.)*., 108, 261-271) and two morphological types of storage material could be distinguished (FIG. 14). Large (>20 µm) deposits which are typical for phagocytes and neurons and small storage granules characteristic of oligodendroglia (FIGS. 14C and G). The phagocytes have been previously identified as activated microglial cells (Hess B, et al. (1996) Proc Natl Acad Sci USA. 93(25):14821-6). Storage in phagocytes and neurons can be distinguished by the less compact and more ring-shaped appearance of alcianophilic material in neurons (FIG. 14C inset). In the brain and spinal cord of rhASA-treated mice sulfatide was largely cleared from phagocytes both in the white and gray matter (FIGS. 14A to H) whereas staining of neurons and oligodendrocytes was unaltered and similar as in mock-treated mice (shown for brain in FIGS. 14D and H).

Apart from the nervous system, the kidney was also histologically analysed. Kidneys of mock-treated mice displayed the same sulfatide storage patterns as previously described (Lullmann-Rauch, R. et al. (2001), *Histochem. Cell Biol.*, 116, 161-169). Storage was intense in thin limbs and thick ascending limbs of Henle's loop and moderate in distal convoluted tubules and collecting ducts (FIG. 15). After four enzyme injections the storage material was almost completely cleared from the distal convoluted tubules (FIG. 15J)

and storage was clearly reduced in the upper portions of the thick ascending limbs (FIG. 15G). The storage in thin limbs and collecting ducts, however, persisted and resembled that of mock-treated mice (FIGS. 15B to E).

The analysis of the kidney also revealed a significant 1.4-fold increase of the kidney wet weight in 9-months-old ASA knockout mice compared to wildtype controls (data not shown). Interestingly, enzyme replacement reduced and partially normalized the increased kidney size. The extent of reduction was statistically significant after the third and after the fourth treatment (student's t-test, p<0.05) and the kidney weight declined to 1.2-fold of normal after four injections (not shown). In a second, independent experiment the mean kidney weight of 12-months-old knockout mice was 1.5-fold increased compared to wildtype mice (not shown). It declined significantly (student's t-test, p<0.05) to 1.1-fold of normal after 4 injections of enzyme (not shown). Liver and brain were weighed as controls and no significant differences were detectable between the experimental groups for these organs (not shown).

Discussion

Approximately 30% of the total amount of injected rhASA could be retrieved from dissected mouse organs 5 h after intravenous injection of 40 mg/kg (not shown). Among the retrievable fraction more than 90% was localized to liver while kidney and peripheral nerves shared the vast majority of the remaining enzyme (FIG. 10B). A comparison with previous data about ASA activities in wildtype mice (Matzner U, et al. (2000) Gene Ther. 7(14):1250-7) suggests that enzyme levels after rhASA treatment were on average~95 fold (liver), 1.2-fold (kidney), 0.6-fold (peripheral nerves) and 0.001-fold (brain) of normal.

Already one intravenous injection of rhASA led to a pronounced time- and dose-dependent decline of sulfatide storage in kidney and peripheral nerves (FIG. 11). This is the first proof that ERT using ASA is effective in reducing the sulfatide storage in vivo. Notably, already 5 h after injection of 40 mg/kg a significant decline of sulfatide storage in kidney was detectable (FIG. 11B). Eight days after treatment storage was diminished to a minimum and up to 70% of the excess sulfatide had vanished from kidney (FIG. 11B) and peripheral nerves (FIGS. 12B and C).

Compared to previous gene therapy experiments, in which TLC did not reveal a significant decline of the mean concentration of sulfatide in total kidney (Matzner U, et al. (2002) Gene Ther 9(1):53-63), both the velocity and the extent of storage reduction was surprising. The difference between the two studies is striking since the steady state level of hASA in kidney, which was achieved by transplantation was 1.3-fold of normal on average and thus virtually the same as the maximum level reached by a single injection of 40 mg CHO-rhASA/kg (see above). Thus, CHO-rhASA which was present in kidney only for a couple of days eliminated more than two thirds of excess sulfatide, while the same amount of enzyme did not reduce the mean storage when it was stably expressed from cells of the hematopoietic system for almost one year. The dependence of the therapeutic efficacy on the cell type which expresses the enzyme points to cell type-specific differences in the biosynthesis of human ASA. Cell culture studies suggested that human ASA is inefficiently phosphorylated by cells of the hematopoietic system, but efficiently phosphorylated by CHO and BHK cells (Muschol, N. et al. 2002, *Biochem. J.* 368, 845-853, and FIG. 7B). Phosphorylation appears, however, to be important for therapeutic efficacy in ASA knockout mice. A low phosphorylation of human ASA by hematopoietic cells and a high phosphorylation by CHO cells may thus explain the partial failure of bone marrow stem cell gene therapy and the success of Exyme Replacement Therapy in ASA knockout mice.

The single-dose experiments indicated that clearance of storage is only transient and sulfatide reaccumulated in the second week after treatment (FIG. 11B). The partial reaccumulation of storage can be explained by the limited half life of the internalized rhASA, which was in the range of only 4 days (9B and C). The reaccumulation of sulfatide necessitated a regimen based on repeated enzyme injections in order to maintain or even enhance storage reduction over the long range. Repeated treatment with 20 mg CHO-rhASA per kg resulted in a step-wise decline of sulfatide storage in peripheral tissues (FIGS. 13A, C and D). Up to 65% and 82% of excess sulfatide could be eliminated from kidney and peripheral nerves by four injections, respectively. The histological analysis of kidney revealed the most prominent decline of sulfatide storage in the cortex (FIG. 15). Here storage was abolished or greatly reduced in distal convoluted tubules and the upper portion of the thick ascending limbs of Henle's loop, respectively. Presently, it is unclear why these segments of the nephron respond more clearly to ERT than other segments. Possibly, the region specificity is determined by the expression pattern of the receptor(s) which endocytose rhASA.

Surprisingly, repeated dosing did not only reduce storage in peripheral tissues, but also in the CNS. This was first evidenced by TLC of brain lipids which showed a decline of sulfatide by 13% after the fourth treatment (FIG. 13B). Reduction of CNS storage was, however, more clearly seen in the morphological analysis. Histology of brain and spinal cord revealed a strikingly reduced frequency of the enlarged sulfatide-storing phagocytes throughout the CNS (shown for brain stem in FIG. 14). Thus, the reduction of sulfatide levels in the CNS appears to be mainly due to clearance of lipid from these phagocytes representing activated microglial cells (Hess B, et al. (1996) Proc Natl Acad Sci USA. 93(25):14821-6) rather than from neurons or oligodendroglia. It has been shown recently in animal models for Krabbe and Sandhoff disease that microglial activation plays a major role in the pathogenesis of these related sphingolipid storage diseases (Matsushima, G. K. et al. (1994), *Cell,* 78, 645-656., Wada, R. et al. *Proc. Natl. Acad. Sci. U.S.A.,* 97, 10954-10959). Microglial activation is also prominent in ASA knockout mice in the second year of life (Hess B, et al. (1996) Proc Natl Acad Sci USA. 93(25):14821-6). Reduction of sulfatide storage in microglial cells can therefore be expected to be beneficial even in the absence of detectable clearance of sulfatide from other glial cells and neurons.

Since the blood-brain barrier prevents transfer of rhASA from the circulation to the CNS, the brain did not acquire enzyme levels exceeding 0.1% of normal during the treatment period of 4 weeks (FIGS. 9C and 10B and not shown) due to the low concentrations, arylsulfatase A present in the CNS is unlikely to be responsible for all of the observed clearance of sulfatides from phagocytes. A second mechanism which may contribute to the clearance involves endocytosis of the enzyme into phagocytes prior to immigration into the CNS. However, the main part of the population of CNS phagocytes (i.e. microglia) are believed to represent an autonomous, self-renewing cell population derived from macrophage progenitors immigrated into the CNS early during life, and being distinct from the blood monocytes/macrophages present in non-neural tissues. A third contributory mechanism exists, involving the export of sulfatides from the brain cells to peripheral cells. The driving force for this export appears to be an increasing imbalance of the equilibrium between sulfatide storage in the CNS and peripheral tissues due to the ASA-catalyzed hydrolysis of sulfatide in the periphery.

Example 6

Studies on Neurologic Parameters—Rotarod Studies

ASA knockout mice develop nerve conduction impairments and a number of neurologic symptoms. To measure putative therapeutic effects on neurologic parameters the rotarod performance was examined.

Previous behavioral tests revealed progressive deficits of ASA knockout mice in balancing on a slowly rotating rod (D'Hooge, R. et al. *Brain Res.*, 907, 35-43, Matzner U, et al. (2002) Gene Ther 9(1):53-63). To determine effects of treatment on motor coordination, mice were tested before the first and after the third infusion of CHO-rhASA by rotarod experiments. In a first study mice at a mean age of about 9 months were analysed. In the test before treatment, wildtype mice were successful in 32 of 40 trials (80%), whereas the two groups of (yet untreated) ASA knockout mice were successful in 22 of 40 (55%) and 25 of 40 (63%) trials (not shown). Thus, the data confirmed that behavioral deficits of ASA knockout mice are already detectable, but still comparably mild at 9 months of age (D'Hooge, et al. *Brain Res.*, 907, 35-43). After treatment of one group of knockout mice with three weekly doses of 20 mg CHO-rhASA/kg the same three groups were reanalysed ~4 weeks later. Compared to the first test the mean success of rhASA-treated mice was improved by 27% and reached 82%. In contrast to this group the mean performance of wildtype and mock-treated controls was only improved by 10% and 5%, respectively (FIG. 16B). Thus, by a combination of treatment and training 9 months old ASA knockout mice acquired the ability to stay on the rod with a higher frequency than untrained wildtype mice of the same age.

To investigate effects on more advanced motor coordination disabilities, 12 months old mice (3 months older than the above) were analysed in a second experiment. Now the percentages of successful mice before treatment were 43% (wildtype controls), 18% (ASA knockouts destined for mock treatment) and 10% (ASA knockouts destined for treatment with rhASA) on average (not shown). After treatment 65% of wildtype controls and 13% of mock-treated ASA knockout mice were successful (FIG. 16C). The mean percentage of rhASA-treated knockout mice, however, increased to 31%. Thus, also in elder mice with progressed coordination impairments motor coordination could be substantially improved by three treatments with CHO-rhASA.

Example 7

Studies on Nerve Motor Conduction Velocity

To further measure putative therapeutic effects on neurologic parameters the compound motor action potential (CMAP) nerve conduction of sciatic nerves was studied under anaesthesia by established electrophysiological methods (Zielasek, J. et al. *Muscle Nerve*, 19, 946-952). In brief, the compound motor action potential (CMAP) was recorded with two needle electrodes in the foot muscles after distal stimulation of the tibial nerve at the ankle and proximal stimulation of the sciatic nerve at the sciatic notch. Statistical analysis was performed using Student's t-test.

Neurophysiological studies of the sciatic nerve were done 6 days after the fourth treatment of 12 months old mice. After distal stimulation, age-matched wildtype control animals showed a normal CMAP with an amplitude of $19.0 \pm 1.7$ mV (mean$\pm$SD, n=8), a latency of $0.84 \pm 0.11$ msec and a duration of $3.3 \pm 0.36$ msec (FIG. 16A and FIG. 17). Mock-treated ASA-deficient animals showed a less compact motor response with significantly reduced mean amplitude ($15.6 \pm 3.9$ mV, $p<0.05$) and increased duration ($4.1 \pm 0.31$ msec, $p<0.01$). The mean latency and the nerve conduction velocity was $0.81 \pm 0.09$ mesc and $45.4 \pm 8.8$ m/sec, respectively, and not significantly different from that of wildtype mice (FIG. 16A, FIG. 17 and not shown). Treatment with CHO-rhASA resulted in an increase of the amplitude to normal values ($20.4 \pm 5.9$ mV, $p<0.05$) and a significant decrease of the duration ($3.8 \pm 0.35$ msec, $p<0.05$). Thus the impaired conduction of the sciatic nerve was virtually normalized after treatment with rhASA. Similar data were obtained after proximal stimulation and the data were reproduced in an independent experiment using mice of another treatment series (not shown).

Determination of Electrophysiological Parameters

TABLE 8

| | | | Raw data | | | | | | |
|---|---|---|---|---|---|---|---|---|---|
| | distal mot lat | duration | ampl distal | f-wave | prox lat | dur prox | ampl prox | distance | nerve cond vel |
| | | | | wild-type number | | | | | |
| 43 | 0.84 | 3 | 19.7 | 4.88 | 1.48 | 2.9 | 17.9 | 24 | 37.50 |
| 44 | 1 | 3.6 | 21.6 | 5.72 | 1.6 | 2.9 | 19.7 | 24 | 40.00 |
| 40 | 0.96 | 2.9 | * | 5.48 | 1.52 | 3.2 | * | 26 | 46.43 |
| 37 | 0.88 | 3.7 | 17.4 | 6.04 | 1.6 | 3.2 | 15.8 | 26 | 36.11 |
| 45 | 0.68 | 2.9 | 19.8 | 5.2 | 1.36 | 3 | 16.5 | 26 | 38.24 |
| 39 | 0.76 | 3.2 | 19 | 5.68 | 1.44 | 3.2 | 15.9 | 25 | 36.76 |
| 38 | 0.76 | 3.8 | 16.3 | 6 | 1.4 | 3.3 | 13.8 | 25 | 39.06 |
| mean | 0.84 | 3.30 | 17.40 | 5.57 | 1.49 | 3.10 | 15.41 | 25.14 | 39.16 |
| SD | 0.11 | 0.36 | 4.15 | 0.39 | 0.09 | 0.15 | 3.37 | 0.83 | 3.21 |
| | | | | ko TBS number | | | | | |
| 6 | 0.76 | 3.9 | 10.3 | 5.68 | 1.36 | 3.1 | 6.9 | 25 | 41.67 |
| 4 | 0.84 | 4 | 11.3 | 5.64 | 1.44 | 3.3 | 11.7 | 24 | 40.00 |
| 2 | 1 | 4.3 | 12.4 | 5.32 | 1.4 | nd | 13.6 | 27 | 67.50 |
| 3 | 0.8 | 4.8 | 15.7 | 5.64 | 1.44 | 3.6 | 14.8 | 25 | 39.06 |
| 7 | 0.76 | 4 | 16.8 | 4.76 | 1.32 | nd | 11.7 | 25 | 44.64 |
| 1 | 0.84 | 4.2 | 17 | 5.48 | 1.36 | nd | 12.8 | 25 | 48.08 |

TABLE 8-continued

Raw data

| | distal mot lat | duration | ampl distal | f-wave | prox lat | dur prox | ampl prox | distance | nerve cond vel |
|---|---|---|---|---|---|---|---|---|---|
| 5 | 0.8 | 4 | 23 | 5.08 | 1.4 | nd | 18.1 | 26 | 43.33 |
| 8 | 0.68 | 3.7 | 18.1 | 5.04 | 1.32 | nd | 16.2 | 25 | 39.06 |
| mean | 0.81 | 4.11 | 15.58 | 5.33 | 1.38 | 3.33 | 13.23 | 25.25 | 45.42 |
| SD | 0.09 | 0.31 | 3.89 | 0.32 | 0.04 | 0.21 | 3.16 | 0.83 | 8.83 |
| ko rhASA number | | | | | | | | | |
| 26 | 0.76 | 4.3 | 28.5 | 5.2 | 1.36 | nd | 24 | 25 | 41.67 |
| 11 | 0.84 | 4.3 | 25.3 | 5.88 | 1.36 | nd | 22.6 | 24 | 46.15 |
| 27 | 0.68 | 4 | 12.7 | 5.08 | 1.36 | nd | 12.9 | 26 | 38.24 |
| 18 | 0.8 | 3.6 | 22.2 | 5.16 | 1.32 | nd | 17.2 | 25 | 48.08 |
| 14 | 0.72 | 3.4 | 17.7 | 4.88 | 1.32 | nd | 17.1 | 26 | 43.33 |
| 30 | 0.68 | 3.5 | 16.8 | 4.68 | 1.24 | nd | 14.3 | 25 | 44.64 |
| 24 | 0.76 | 3.6 | 12.7 | 5 | 1.32 | nd | 11.4 | 27 | 48.21 |
| 25 | 0.84 | 3.5 | 27.5 | 5 | 1.44 | nd | 11.9 | 24 | 40.00 |
| mean | 0.76 | 3.78 | 20.43 | 5.11 | 1.34 | nd | 16.43 | 25.25 | 43.79 |
| SD | 0.06 | 0.35 | 5.94 | 0.33 | 0.05 | nd | 4.46 | 0.97 | 3.43 |

* wildtype mouse #40 yielded low amplitudes due to technical problems (ampl dist = 8.0; ampl prox = 8.3); nd - duration after proximal stimulation not determinable

TABLE 9 statistical evaluation using Student's t-test
P values

| | dml | duration | ampl distal | f-wave | prox lat | dur prox | ampl prox | distance | NLG |
|---|---|---|---|---|---|---|---|---|---|
| wildtype untreated vs knockout mock-treated | 0.2930 | 0.0004 | 0.0449 | 0.1203 | 0.0073 | nd | 0.0258 | nd | 0.0611 |
| knockout mock-treated vs knockout rhASA-treated | 0.1149 | 0.0375 | 0.0461 | 0.1121 | 0.0745 | nd | 0.0720 | nd | 0.3282 | grey - statistically significant difference (P < 0.05)

Results the following changes in the electrophysiological pattern of knockout mice are statistically significant (wildtype vs mock-treated knockouts):
  duration (of amplitude after distal stimulation) is increased
  amplitude (height) after distal stimulation is decreased
  latency after proximal stimulation is decreased
  amplitude (height) after proximal stimulation is decreased
treatment results in the following statistically significant changes of the pattern (mock-treated knockouts vs rhASA-treated knockouts)
  duration (of amplitude after distal stimulation) is decreased towards normal values
  amplitude (height) after distal stimulation is increased towards normal values (1) The amplitude is the result (sum) of individual axon potentials. If all axon potentials pass the recording electrode at the same time point the amplitude would be short and high. If the potentials pass it at different time points (because some axons conduct fast and others slow) the amplitude would be broad and low. Compared to wildtype mice the amplitude of ASA knockout mice is more flattened and extended.

(2) For the determination of the nerve conductance velocity the time between stimulation and begin of the amplitude is measured. This time is virtually the same for knockout and wildtype mice. It can be concluded that the knockout mice possess nerve fibers with normal conductance velocity.

From (1) and (2) it can be concluded that knockout mice have fast conducting fibers (normal nerve conductance velocity), but also a substantial fraction of fibers which conductance velocity is more or less reduced (flattened and extended amplitude).

Treatment results in a significant improvement of the duration and height of the amplitude. Recordings of the CMAP in the sciatic nerve of untreated ASA knockout mice suggested an impaired conduction of a subset of axonal fibers. This was indicated by a significantly lower and broader amplitude in the presence of a normal nerve conduction velocity (FIG. 16A and FIG. 17). Treatment decreased the duration and increased the height of the flattened amplitude demonstrating the abrogation of inhibitory effects. This corrective effect might be associated with the critical role of sulfatide in the organisation of paranodal axoglial junctions and the correct clustering of voltage-gated $Na^+$ and $K^+$ channels along the axolemma. The possibility to reverse changes of the CMAP by a comparably short exposure to recombinant enzyme might have great implications for the treatment of MLD. Since PNS symptoms prevail before the end stage of MLD, ERT might substantially retard the disease progression and improve the quality of life. This notion is supported by the rotarod data in mice indicating

REFERENCES

Baum, H., Dodgson, K. S. and Spencer, B. (1959) The assay of arylsulphatases A and B in human urine. *Clin. Chim. Acta.*, 4, 453-455.

Coenen, R., Gieselmann, V. and Lullmann-Rauch, R. (2001) Morphological alterations in the inner ear of the arylsulfatase A-deficient mouse. *Acta Neuropathol. (Berl.).*, 101, 491-498.

Dafang, W and Paradrige W. M. Neuroprotection with non-invasive neurotrophin delivery to the brain. Proc. Natl. Acad. Sci. 1999, 96, 254-259

Demeule M, Poirier J, Jodoin J, Bertrand Y, Desrosiers R R, Dagenais C, Nguyen T, Lanthier J, Gabathuler R, Kennard M, Jefferies W A, Karkan D, Tsai S, Fenart L, Cecchelli R, Beliveau R. High transcytosis of melanotransferrin (P97) across the blood-brain barrier. High transcytosis of melanotransferrin (P97) across the blood-brain barrier. J Neurochem 2002, 83, 924-33

D'Hooge, R., Van Dam, D., Franck, F., Gieselmann, V. and De Deyn, P P. (2001) Hyperactivity, neuromotor defects, and impaired learning and memory in a mouse model for metachromatic leukodystrophy. *Brain Res.*, 907, 35-43.

Dierks T, Schmidt B, von Figura K. 1997. Conversion of cysteine to formylglycine: a protein modification in the endoplasmic reticulum. *Proc Natl Acad Sci USA* 94(22): 11963-11968.

Dunican D J, Doherty P. Designing cell-permeant phosphopeptides to modulate intracellular signaling pathways. Biopolymers. 2001; 60(1):45-60.

Gieselmann, V., Matzner, U., Hess, B., Lullmann-Rauch, R., Coenen, R., Hartmann, D., D'Hooge, R., DeDeyn, P. and Nagels, G. (1989) Metachromatic leukodystrophy: molecular genetics and an animal model. *J. Inherit. Metab. Dis.*, 21, 564-574.

Gieselmann, V., Franken, S., Klein, D., Månsson, J. E., Sandhoff, R., Lullmann-Rauch, R., Hartmann, D., Saravanan, V. P., De Deyn, P. P., D'Hooge, R., et al. (2003) Metachromatic leukodystrophy: consequences of sulphatide accumulation. *Acta Paediatr. Suppl.*, 92, 74-79.

Gieselmann, V., Schmidt, B. and von Figura K. (1992) In vitro mutagenesis of potential N-glycosylation sites of arylsulfatase A. Effects on glycosylation, phosphorylation, and intracellular sorting. *J. Biol. Chem.*, 267, 13262-13266.

Hess B, Saftig P, Hartmann D, Coenen R, Lullmann-Rauch R, Goebel H H, Evers M, von Figura K, D'Hooge R, Nagels G, De Deyn P, Peters C, Gieselmann V. (1996) Proc Natl Acad Sci USA. 93(25):14821-6.

Ho A, Schwarze S R, Mermelstein S J, Waksman G, Dowdy S F. Synthetic protein transduction domains: enhanced transduction potential in vitro and in vivo. Cancer Res. 2001 Jan. 15; 61(2):474-7.

Kakkis, E (2003) 9th International Congress of Inborn errors of Metabolism, September 3rd, Brisbane, Australia.

Kudoh T, Wenger D. A. Diagnosis of metachromatic leukodystrophy, Krabbe disease, and Farber disease after uptake of fatty acid-labeled cerebroside sulfate into cultured skin fibroblasts. J Clin Invest. 1982 July; 70(1):89-97.

Lindgren M, Hallbrink M, Prochiantz A, Langel U. Cell-penetrating peptides. Trends Pharmacol Sci. 2000 March; 21(3):99-103.

Lukatela G, Krauss N, Theis K, Selmer T, Gieselmann V, von Figura K, Saengen W. Crystal structure of human arylsulfatase A: the aldehyde function and the metal ion at the active site suggest a novel mechanism for sulfate ester hydrolysis. Biochemistry. 1998 Mar. 17; 37(11):3654-64.

Lullmann-Rauch, R., Matzner, U., Franken, S., Hartmann, D. and Gieselmann, V. (2001) Lysosomal sulfoglycolipid storage in the kidneys of mice deficient for arylsulfatase A (ASA) and of double-knockout mice deficient for ASA and galactosylceramide synthase. *Histochem. Cell Biol.*, 116, 161-169.

Matsushima, G. K., Taniike, M., Glimcher, L. H., Grusby, M. J., Frelinger, J. A., Suzuki, K. and Ting, J. P. (1994) Absence of MHC class II molecules reduces CNS demyelination, microglial/macrophage infiltration, and twitching in murine globoid cell leukodystrophy. *Cell*, 78, 645-656.

Matzner U, Hartmann D, Lullmann-Rauch R, Coenen R, Rothert F, Mansson J E, Fredman P, D'Hooge R, De Deyn P P, Gieselmann V. (2002) Gene Ther 9(1):53-63

Matzner U, Harzer K, Learish R D, Barranger J A, Gieselmann V. (2000b) Gene Ther. 7(14): 1250-7

Matzner, U., Habetha, M. and Gieselmann, V. (2000) Retrovirally expressed human arylsulfatase A corrects the metabolic defect of arylsulfatase A-deficient mouse cells. *Gene Ther.*, 7, 805-812.

Muschol, N., Matzner, U., Tiede, S., Gieselmann, V., Ullrich, K. and Braulke, T. (2002) Secretion of phosphomannosyl-deficient arylsulphatase A and cathepsin D from isolated human macrophages. *Biochem. J.*, 368, 845-853.

Pan W, Kastin A J. TNF-alpha transport across the blood-brain barrier is abolished in receptor knockout mice. Exp Neurol. 2002 April; 174(2):193-200

Pan W, Kastin A J. Upregulation of the transport system for TNFalpha at the blood-brain barrier. Arch Physiol Biochem. 2001 October; 109(4):350-3.

Remington's Pharmaceutical Sciences 16th edition, Osol, A. Ed. (1980)

Rodman T C, Lutton J D, Jiang S, Al-Kouatly H B, Winston R. Circulating natural IgM antibodies and their corresponding human cord blood cell-derived Mabs specifically combat the Tat protein of HIV. Exp Hematol. 2001 August; 29(8):1004-9.

Rothenberger S, Food M R, Gabathuler R, Kennard M L, Yamada T, Yasuhara O, McGeer P L, Jefferies W A. Coincident expression and distribution of melanotransferrin and transferrin receptor in human brain capillary endothelium. Brain Res. 1996, 712, 117-21

Sandhoff R, Hepbildikler S T, Jennemann R, Geyer R, Gieselmann V, Proia R L, Wiegandt H, Grone H J J (2002) Biol Chem 277(23):20386-98

Schmidt, B, Selmer, T, Ingendoh, A, von Figura, K. A novel amino acid modification in sulfatases that is defective in multiple sulfatase deficiency. Cell. 1995 Jul. 28; 82(2): 271-8

Schwarze S R, Hruska K A, Dowdy S F. Protein transduction: unrestricted delivery into all cells? Trends Cell Biol. 2000 July; 10(7):290-5.

Scott, J. E. and Dorling, J. (1965) Differential staining of acid glycosaminoglycans (mucopolysaccharides) by alcian blue in salt solutions. *Histochemie*, 5, 221-233.

Selmer T, Hallmann A, Schmidt B, Sumper M, von Figura K. 1996. The evolutionary conservation of a novel protein modification, the conversion of cysteine to serine semialdehyde in arylsulfatase from *Volvox carteri*. *Eur J Biochem* 238:341-345.

Sommerlade, H J., Hille-Rehfeld, A., von Figura, Gisselmann, K. Four monoclonal antibodies inhibit the recognition of aryl sulfatase A by the lysosomal enzyme phosphotransferase. Biochem. J. 1994 Jan. 1; 297 (Pt 1):123-30.

Wada, R., Tifft, C. J. and Proia, R. L. (2000) Microglial activation precedes acute neurodegeneration in Sandhoff disease and is suppressed by bone marrow transplantation. *Proc. Natl. Acad. Sci. U.S.A.*, 97, 10954-10959.

Wittke, D., Hartmann, D., Gieselmann, V. and Lullmann-Rauch, R. (2004) Lysosomal sulfatide storage in the brain of arylsulfatase A-deficient mice: cellular alterations and topographic distribution. *Acta Neuropathol. (Berl.).*, 108, 261-271.

Yao, J. K. and Rastetter, G. M. (1985) Microanalysis of complex tissue lipids by high-performance thin-layer chromatography. *Anal. Biochem.*, 150, 111-116.

Zielasek, J., Martini, R. and Toyka, K. V. (1996) Functional abnormalities in P0-deficient mice resemble human hereditary neuropathies linked to P0 gene mutations. *Muscle Nerve*, 19, 946-952.

The invention claimed is:

1. A process for production of a purified recombinant mature polypeptide with arylsulfatase A (ASA) activity in a continuous cell culture system, the process comprising:
   i) continuously culturing a mammalian cell capable of secreting said mature polypeptide into a liquid culture medium; and
   ii) purifying the mature polypeptide by a purification process comprising one or more steps of affinity chromatography and/or ion exchange chromatography,
   wherein the process of (ii) comprises a polishing step including a passive step, wherein the mature polypeptide with arylsulfatase A activity passes through a cation exchange chromatography resin or membrane and/or affinity chromatography resin without binding thereto and an active step, wherein the mature polypeptide with arylsulfatase A activity is detained within and subsequently eluted from an anion exchange membrane or resin, and wherein the cation exchange chromatography resin or membrane and the anion exchange resin or membrane are coupled or connected in a series,
   wherein said mammalian cell comprises a nucleotide sequence which encodes a polypeptide comprising (a) SEQ ID NOs:2 or 4 or (b) a mutant sequence at least 95% identical to SEQ ID NOs:2 or 4, and wherein said mature polypeptide is a post-translationally modified product thereof that is produced and secreted by said cell, and has arylsulfatase A activity, and wherein the continuous culturing is for a period of at least one week.

2. The process according to claim 1, wherein the mammalian cells are of human or primate origin.

3. The process according to claim 1, wherein the process of ii) comprises one or more steps of Expanded Bed Chromatography.

4. The process according to claim 1, wherein the process of ii) comprises the following steps:
   introducing a supernatant containing said mature polypeptide into a first equilibrated chromatography column and eluting one or more fraction(s) containing said mature polypeptide;
   loading the fraction(s) from the first equilibrated chromatography column on a second equilibrated chromatography column and eluting one or more fraction(s) containing said mature polypeptide;
   buffer exchange of said mature polypeptide present in the fraction(s) from the second equilibrated chromatography column by tangential flow filtration;
   polishing the preparation of said mature polypeptide from the buffer exchange step in one or two or more successive steps, each step comprising loading the preparation on an equilibrated chromatography columns and eluting one or more fraction(s) containing said mature polypeptide, wherein said polishing comprises a passive step, in which said mature polypeptide passes through a cation chromatography resin or membrane and/or affinity chromatography resin without binding thereto, and an active step, wherein said polypeptide is detained within and subsequently eluted from an anion exchange membrane or resin; and
   passing the fraction(s) from the polishing step through a viral reduction filter and/or inactivating virus in said fraction(s) with a virus inactivating agent.

5. The process according to claim 4, further comprising concentrating the mature polypeptide by tangential filtration prior to introducing the supernatant into the first equilibrated chromatography column.

6. The process according to claim 4, wherein the first chromatography column is an anion exchange column.

7. The process according to claim 6, wherein said anion exchange column is a DEAE Sepharose column or a DEAE Streamline column.

8. The process according to claim 4, wherein the second chromatography column is a hydrophobic interaction column.

9. The process according to claim 4, wherein the inactivating agent is a detergent.

10. The process of claim 1, wherein the mature polypeptide has a specific arylsulfatase A activity of at least 20 units/mg.

11. The process of claim 1, wherein the mutant sequence is at least 96% identical to SEQ ID NO:2 or 4.

12. The process of claim 1, wherein the mutant sequence is at least 97% identical to SEQ ID NO:2 or 4.

13. The process of claim 1, wherein the mutant sequence is at least 98% identical to SEQ ID NO:2 or 4.

14. The process of claim 1, wherein the mutant sequence is at least 99% identical to SEQ ID NO:2 or 4.

15. The process of claim 1, wherein the polypeptide comprises SEQ ID NOs:2 or 4.

16. The process of claim 1, wherein the produced arylsulfatase A consists of SEQ ID NO:3.

17. The process of claim 1, wherein the encoded polypeptide, when aligned by sequence alignment software to SEQ ID NO:2 or 4, has a cysteine in the position aligned with Cys-69 in SEQ ID NO:2 or Cys-51 in SEQ ID NO:4.

18. The process of claim 17, wherein a linear sequence of five amino acids within said polypeptide, and including said cysteine, is identical to the aligned sequence of five amino acids in SEQ ID NO:2 or SEQ ID NO:4.

19. The process of claim 17, wherein a linear sequence of nine amino acids within said polypeptide, and including said cysteine, is identical to the aligned sequence of nine amino acids in SEQ ID NO:2 or SEQ ID NO:4.

20. The process of claim 17, wherein a linear sequence of twenty amino acids within said polypeptide, and including said cysteine, is at least 95% identical to the aligned sequence of twenty amino acids in SEQ ID NO:2 or SEQ ID NO:4.

21. The process of claim 17, wherein a linear sequence of twenty amino acids within said polypeptide, and including said cysteine, is identical to the aligned sequence of twenty amino acids in SEQ ID NO:2 or SEQ ID NO:4.

22. The process of claim 17, wherein the encoded polypeptide comprises at least one putative N-glycosylation site.

23. The process of claim 22, wherein the at least one putative N-glycosylation site is phosphorylable.

24. The process of claim 17, wherein the encoded polypeptide, when aligned by sequence alignment software to SEQ ID NO:2 or 4, has asparagine in the positions aligned with Asn-158 and Asn-350 in SEQ ID NO:2 or Asn-140 and Asn-332 in SEQ ID NO:4.

25. The process of claim 24, wherein the encoded polypeptide, when aligned by sequence alignment software to SEQ ID NO:2 or 4, has asparagine in the position aligned with Asn-184 in SEQ ID NO:2 or Asn-166 in SEQ ID NO:4.

26. The process of claim 1, wherein said continuous culturing is for a period of at least two weeks.

27. The process of claim 1, wherein said continuous culturing is for a period of at least three weeks.

28. The process of claim 1, wherein said continuous culturing is for a period of at least four weeks.

29. The process of claim 1, wherein said continuous culturing is carried out in a cell culture system comprising one or more bioreactors, said cells being in said bioreactor(s), said system comprising means for collecting medium comprising said polypeptide, and a cell retention device for retaining cells in said bioreactor(s) when said medium is collected, and said system comprising means for adding fresh medium.

30. The process of claim 29, wherein said cell retention device is at least 95% efficient.

31. The process of claim 29, wherein medium comprising said polypeptide is collected, while retaining cells in said bioreactor(s), at least once prior to the conclusion of said culturing.

32. The process of claim 31, in which medium comprising said polypeptide is collected at least daily.

33. A process of preparing a pharmaceutically acceptable formulation comprising a polypeptide with ASA activity, said process comprising producing said polypeptide by the process of claim 1, and formulating a pharmaceutically acceptable formulation comprising said polypeptide.

34. The process of claim 4, further comprising formulating the fraction(s) from the viral reduction and/or inactivation step in order to obtain a preparation of said polypeptide in a suitable formulation buffer.

35. The process of claim 34, further comprising filling the formulated preparation of said polypeptide into a suitable container and freeze-drying the sample.

* * * * *

UNITED STATES PATENT AND TRADEMARK OFFICE
CERTIFICATE OF CORRECTION

PATENT NO.        : 8,536,315 B2
APPLICATION NO. : 10/588082
DATED             : September 17, 2013
INVENTOR(S)       : Fogh et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 476 days.

Signed and Sealed this
Fifteenth Day of September, 2015

Michelle K. Lee
*Director of the United States Patent and Trademark Office*